United States Patent
Pratt et al.

(10) Patent No.: US 10,105,472 B2
(45) Date of Patent: *Oct. 23, 2018

(54) DISPOSABLE REDUCED-PRESSURE THERAPY SYSTEM WITH MECHANICAL FEEDBACK

(71) Applicant: KCI Licensing, Inc., San Antonio, TX (US)

(72) Inventors: Benjamin Andrew Pratt, Poole (GB); Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 791 days.

This patent is subject to a terminal disclaimer.

(21) Appl. No.: 14/503,615

(22) Filed: Oct. 1, 2014

(65) Prior Publication Data

US 2015/0094674 A1    Apr. 2, 2015

Related U.S. Application Data

(60) Provisional application No. 61/885,781, filed on Oct. 2, 2013.

(51) Int. Cl.
*A61M 1/00* (2006.01)
*A61F 13/00* (2006.01)

(52) U.S. Cl.
CPC ..... *A61M 1/0025* (2014.02); *A61F 13/00068* (2013.01); *A61M 1/0027* (2014.02);
(Continued)

(58) Field of Classification Search
CPC ............. A61M 1/0025; A61M 1/0027; A61M 1/0035; A61M 1/0031; A61M 1/0088; A61F 13/00068

See application file for complete search history.

(56) References Cited

U.S. PATENT DOCUMENTS 1,355,846 A    10/1920   Rannells
2,547,758 A     4/1951   Keeling
(Continued)

FOREIGN PATENT DOCUMENTS

AU    550575 A1    3/1986
AU    745271       4/1999
(Continued)

OTHER PUBLICATIONS

Chinese First Office Action corresponding to Application No. 2014800596338, dated May 27, 2017.
(Continued)

*Primary Examiner* — Tatyana Zalukaeva
*Assistant Examiner* — Kai Weng

(57) ABSTRACT

Systems, methods, and apparatuses for providing feedback for reduced-pressure treatment of a tissue site are described. A regulator may include a supply chamber fluidly coupled to the dressing, a control chamber fluidly coupled to the dressing, a charging chamber fluidly coupled to the supply chamber through a port, and a regulator valve operable to control fluid communication through the port based on a pressure differential between the control chamber and a therapy pressure. The feedback system may include one or more mechanical feedback interfaces fluidly coupled to the regulator to provide a signal of at least one of an application of reduced-pressure therapy, a leak condition, a blockage condition, and a canister full condition.

78 Claims, 23 Drawing Sheets

(52) U.S. Cl.
CPC ........ *A61M 1/0031* (2013.01); *A61M 1/0035* (2014.02); *A61M 1/0088* (2013.01); *A61M 2205/15* (2013.01); *A61M 2205/183* (2013.01); *A61M 2205/581* (2013.01); *A61M 2205/582* (2013.01); *A61M 2205/583* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2008/0271804 A1* | 11/2008 | Biggie ................ A61M 1/0088 138/137 |
| 2009/0157016 A1 | 6/2009 | Adahan |
| 2010/0185048 A1* | 7/2010 | Lonky ................ A61M 1/0031 600/37 |
| 2011/0224633 A1 | 9/2011 | Robinson et al. |
| 2013/0053797 A1 | 2/2013 | Locke et al. |
| 2014/0200535 A1 | 7/2014 | Locke et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2007030598 A2 | 3/2007 |
| WO | 2009135171 A2 | 11/2009 |
| WO | 2013/078214 A1 | 5/2013 |

(56) References Cited

FOREIGN PATENT DOCUMENTS

| WO | 2014043225 A2 | 3/2014 |
|---|---|---|
| WO | 2014113504 A1 | 7/2014 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for PCT/US2014/058667 dated May 29, 2015.
Extended European Search Report for corresponding Application No. 171921547, dated May 11, 2018.

* cited by examiner

DISPOSABLE REDUCED-PRESSURE THERAPY SYSTEM WITH MECHANICAL FEEDBACK

RELATED APPLICATION

The present invention claims the benefit, under 35 USC § 119(e), of the filing of U.S. Provisional Patent Application Ser. No. 61/885,781, entitled "DISPOSABLE REDUCED-PRESSURE THERAPY SYSTEM WITH MECHANICAL FEEDBACK," filed Oct. 2, 2013, which is incorporated herein by reference for all purposes.

TECHNICAL FIELD

The subject matter described herein relates generally to monitoring reduced-pressure therapy and, more particularly, but not by way of limitation, to mechanical feedback of reduced-pressure therapy supplied by a wall-suction source.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

Illustrative embodiments of systems, methods, and apparatuses for regulating pressure are described below. One such illustrative embodiment may be described as a reduced-pressure system. The reduced-pressure system may include a dressing, and a regulator. The regulator may include a supply chamber adapted to be fluidly coupled to the dressing and a control chamber adapted to be fluidly coupled to the dressing. The regulator may also include a charging chamber fluidly coupled to the supply chamber through a port. A regulator valve may be coupled to the control chamber and operable to reciprocate at least partially within the control chamber to control fluid communication through the port based on a differential between a control pressure in the control chamber and a therapy pressure. The reduced-pressure system may also include a feedback interface fluidly coupled to the regulator and adapted to signal an operating state of the reduced-pressure therapy system in response to a pressure received through the fluid coupling.

Another illustrative embodiment relates to a method for regulating pressure in a reduced-pressure therapy system. The method reduces a charging pressure in a charging chamber below a therapy pressure. The method regulates fluid communication between a supply chamber and the charging chamber based on a differential between a control pressure in a control chamber and the therapy pressure. The method fluidly couples a feedback interface between at least two of the control chamber, the charging chamber, a dressing, and a reduced-pressure source. The method signals an operating state of the reduced-pressure therapy system with the feedback interface in response to a pressure received through the fluid coupling.

Yet another illustrative embodiment relates to a feedback system for monitoring the application of reduced pressure therapy. The feedback system includes at least one feedback interface adapted be fluidly coupled between a reduced-pressure source and a dressing. The feedback interface indicates an operating state of a reduced-pressure system in response to at least one of a leak condition, an overpressure condition, a blockage condition, a container full condition, and an application of reduced-pressure therapy.

In still another embodiment, a reduced-pressure system is described. The system may include a dressing and a regulator. The regulator may include a supply chamber adapted to be fluidly coupled to the dressing and a charging chamber fluidly coupled to the supply chamber through a port. The regulator may have a regulator valve coupled to the charging chamber and operable to reciprocate to control fluid communication through the port based on a differential between an ambient pressure and a therapy pressure. The system may also include a feedback interface fluidly coupled to the regulator and adapted to signal an operating state of the reduced-pressure therapy system in response to a pressure received through the fluid coupling.

Other features and advantages will become apparent with reference to the drawings and detailed description that follow.

DETAILED DESCRIPTION

New and useful systems, methods, and apparatuses associated with monitoring pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
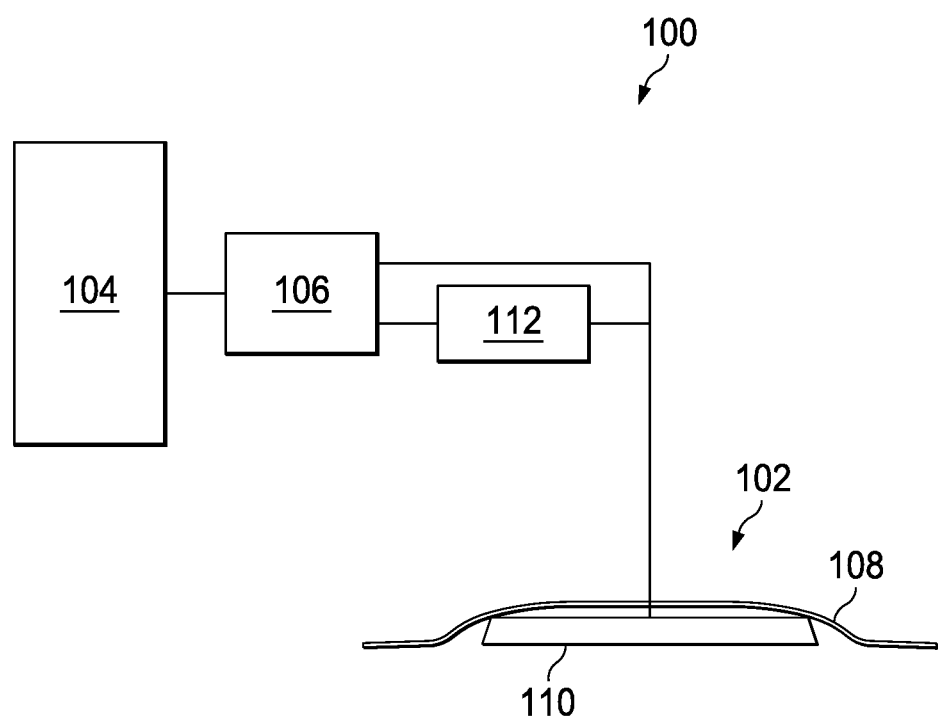
FIG. 1 is a functional block diagram of an example embodiment of a reduced-pressure therapy system that can regulate therapeutic pressure in accordance with this specification.

FIG. 1 is a simplified functional block diagram of an example embodiment of a reduced-pressure therapy system 100 that can regulate therapeutic pressure in accordance with this specification. As shown in the illustrative embodiment of FIG. 1, the reduced-pressure therapy system 100 may include a dressing 102 fluidly coupled to a reduced-pressure source 104. A regulator or controller, such as a regulator 106, may also be fluidly coupled to the dressing 102 and the reduced-pressure source 104. The dressing 102 generally includes a drape, such as a drape 108, and a tissue interface, such as a manifold 110. The reduced-pressure therapy system 100 may also include a fluid container, such as a container 112, coupled to the dressing 102 and the reduced-pressure source 104.

In general, components of the reduced-pressure therapy system 100 may be coupled directly or indirectly. For example, the reduced-pressure source 104 may be directly coupled to the regulator 106 and indirectly coupled to the dressing 102 through the regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the manifold 110, may be placed within, over, on, against, or otherwise adjacent to a tissue site. For example, the manifold 110 may be placed against a tissue site, and the drape 108 may be placed over the manifold 110 and sealed to tissue proximate to the tissue site. Tissue proximate to a tissue site is often undamaged epidermis peripheral to the tissue site. Thus, the dressing 102 can provide a sealed therapeutic environment proximate to the tissue site. The sealed therapeutic environment may be substantially isolated from the external environment, and the reduced-pressure source 104 can reduce the pressure in the sealed therapeutic environment. Reduced pressure applied uniformly through the tissue interface in the sealed therapeutic environment can induce macrostrain and microstrain in the tissue site, as well as remove exudates and other fluids from the tissue site. The removed exudates and other fluids can be collected in the container 112 and disposed of properly.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, in the context of reduced-pressure therapy, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, a fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by the dressing 102. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 104, may be a reservoir of air at a reduced pressure, or may be a manual or electrically-powered device that can reduce the pressure in a sealed volume, such as a vacuum pump, a suction pump, a wall-suction port available at many healthcare facilities, or a micro-pump, for example. A reduced-pressure source may be housed within or used in conjunction with other components, such as sensors, processing units, alarm indicators, memory, databases, software, display devices, or operator interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the manifold 110, can generally be adapted to contact a tissue site or other layers of a dressing, such as the dressing 102. A tissue interface may be partially or fully in contact with a tissue site. If a tissue site is a wound, for example, a tissue interface may partially or completely fill the wound, or may be placed over the wound. A tissue interface may take many forms, and may be many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids from a tissue site. A manifold may include flow channels or pathways that can distribute fluids provided to and removed from a tissue site. In one illustrative embodiment, the flow channels or pathways may be interconnected to improve distribution of fluids provided to or removed from a tissue site. For example, a manifold may be an open-cell foam, porous tissue collection, and other porous material such as gauze or felted mat that generally includes structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam material may be either hydrophobic or hydrophilic. In one non-limiting example, the manifold 110 may be reticulated polyurethane foam such as GranuFoam® dressing available from Kinetic Concepts, Inc. of San Antonio, Tex.

In some embodiments, such as embodiments in which the manifold 110 may be made from a hydrophilic material, the manifold 110 may also wick fluid away from a tissue site while continuing to distribute reduced pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. White-Foam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface may further promote granulation at a tissue site if pressure within a sealed therapeutic environment is reduced. For example, any or all of the surfaces of the manifold 110 may have an uneven, coarse, or jagged profile that can induce microstrains and stresses at a tissue site if reduced pressure is applied through the manifold 110.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two environments or components, such as between a therapeutic environment and a local external environment. The sealing member may be, for example, an impermeable or semi-permeable, elastomeric film or barrier that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

A "container," such as the container 112 in FIG. 1, broadly includes a canister, pouch, bottle, vial, or other fluid collection apparatus. The container 112, for example, can be used to manage exudates and other fluids withdrawn from a tissue site. In many environments, a rigid container may be preferred or required for collecting, storing, and disposing of fluids. In other environments, fluids may be properly disposed of without rigid container storage, and a reusable container could reduce waste and costs associated with reduced-pressure therapy.

In general, reduced-pressure therapy can be beneficial for wounds of all severity, but the cost and complexity of reduced-pressure therapy systems often limit the application of reduced-pressure therapy to large, highly-exudating wounds present on patients undergoing acute or chronic care, as well as other severe wounds that are not readily susceptible to healing without application of reduced pressure. Many developing regions may not have access to dedicated, electrically-operated reduced-pressure sources for reduced-pressure therapy. Instead, these regions may rely on wall-suction sources for the supply of reduced pressure. These wall-suction sources may be seen as a practical, suitable, and lower cost alternative to a dedicated therapy unit with electronic controls.

Wall-suction sources are capable of providing continuous, or nearly continuous, supplies of reduced pressure. However, wall-suction sources may provide a broad range of reduced pressures and may require an operator to select an appropriate reduced pressure to be supplied. If the reduced pressure is set too low at the wall-suction source, removal of exudates and other wound fluids from the tissue site will not occur. If the reduced pressure is too high, the reduced-pressure therapy may cause internal bleeding and further damage to a tissue site. For at least these reasons, treatment of a tissue site with reduced pressure provided by a wall-suction source should be regulated for reduced-pressure therapy.

The reduced-pressure therapy system 100 may overcome these shortcomings and others by providing feedback and mechanical regulation of therapeutic pressure. In some embodiments, for example, a regulator can regulate fluid communication between a supply chamber and a charging chamber, and one or more feedback interfaces can provide feedback to alert operators of an operating state of reduced-pressure therapy during the provision of reduced-pressure therapy. For example, the feedback interfaces may provide an operator with an operating state of one or more of the following: a control pressure, a supply pressure, a differential between the control pressure and the supply pressure, a leak condition, a blockage condition, a canister full condition, and an overpressure condition. In some embodiments, the reduced-pressure therapy system 100 may provide a highly configurable system that is low cost, disposable, single-patient use, or reusable.

Regulators

Figure 2A:
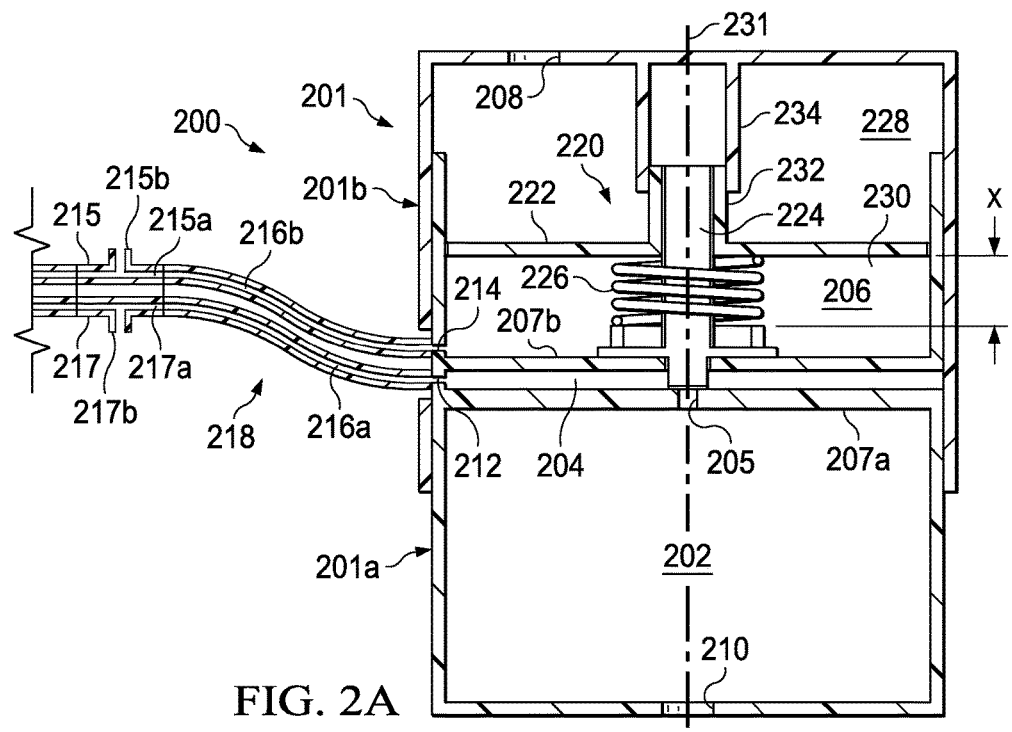
FIGS. 2A-2B are schematic cross-sections of an example embodiment of a regulator in the reduced-pressure therapy system.
Figure 2B:
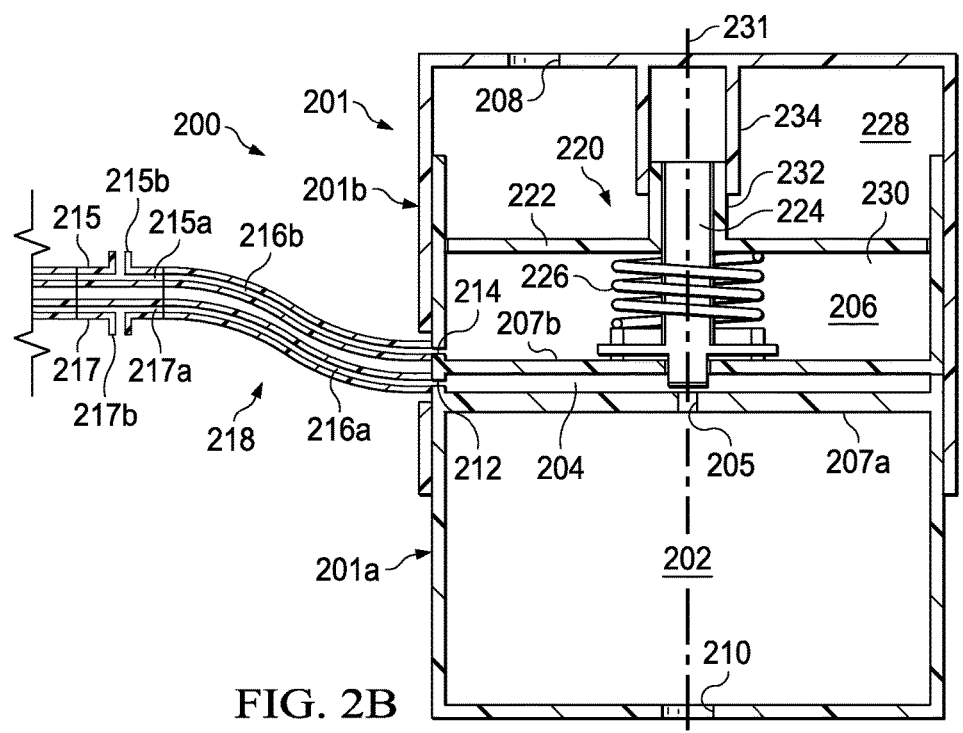

FIGS. 2A-2B are simplified schematic cross-sections illustrating details of an example embodiment of a regulator 200. The regulator 200 is an example embodiment of the regulator 106 in FIG. 1. As illustrated, the regulator 200 can include a housing 201 having a charging chamber 202, a supply chamber 204, and a control chamber 206. The charging chamber 202 may be fluidly coupled to the supply chamber 204 through a conduit, passage, or port, such as a charging port 205. A port 208 can provide fluid communication between the control chamber 206 and a source of ambient pressure. The charging chamber 202 may also include a port, such as a port 210, which can be fluidly coupled to a source of reduced pressure, such as the reduced-pressure source 104. The charging chamber 202 may be adapted to receive reduced pressure from a device that can be manually-actuated, or alternatively that can be powered by electrical or other means.

A supply port 212 may fluidly couple the supply chamber 204 to a dressing, such as the dressing 102 in FIG. 1. A control port 214 may fluidly couple the control chamber 206 to the dressing 102. For example, in one embodiment, a first lumen such as a supply lumen 216a, may fluidly connect the supply port 212 and the supply chamber 204 to a dressing. A second lumen, such as a feedback lumen 216b, may fluidly couple the control port 214 and the control chamber 206 to the dressing 102. In some embodiments, the supply lumen 216a and the feedback lumen 216b may be disposed within a single multi-lumen tube, such as a tube 218. In other embodiments, more than one tube may be used to couple a dressing to the supply port 212 and the control port 214.

A tee-fitting 215 may be coupled to the feedback lumen 216b. The tee-fitting 215 may have a first passage 215a and a second passage 215b. The first passage 215a and the second passage 215b may be perpendicular to and in fluid communication with one another. The first passage 215a may be fluidly coupled inline between the control chamber 206 and a dressing. For example, the first passage 215a may be fluidly coupled to the feedback lumen 216b. The second passage 215b may be fluidly coupled to another device, such as a pressure sensor, fluid source, or sampling device, for example. In some embodiments, a pressure sensor may be fluidly coupled to the second passage 215b and be in fluid communication with a control pressure in the control chamber 206.

A tee-fitting 217 may be coupled to the supply lumen 216a. The tee-fitting 215 may have a first passage 217a and a second passage 217b. The first passage 217a and the second passage 217b may be perpendicular to and in fluid communication with each other. At least one of the passages may be fluidly coupled inline between the supply chamber 204 and a dressing. For example, the first passage 217a may be fluidly coupled to the supply lumen 216a. The second passage 217b may be fluidly coupled to another device, such as a pressure sensor, fluid source, or sampling device, for example. In some embodiments, a pressure sensor may be fluidly coupled to the second passage 217b and be in fluid communication with a supply pressure in the supply chamber 204.

A regulator valve 220 can be operably associated with the charging port 205 to regulate fluid communication between the charging chamber 202 and the supply chamber 204. In some embodiments, the regulator valve 220 may include an actuator, a valve body, and an elastic member. An actuator can be a flexible or movable barrier, such as a piston 222. A valve body can be, for example, a generally rigid structure having a first end coupled to, adjoining, abutting, or otherwise engaging the piston 222, and movable with the piston 222, such as a stem 224. A second end of the valve body can be generally sized and shaped to engage and/or seal the charging port 205. In some embodiments, the stem 224 may extend through a partition into the supply chamber 204. An elastic member can be a spring, a rubber, or other elastic structure, such as a regulator spring 226, for example. The regulator spring 226 may be generally disposed between the piston 222 and the charging port 205. The regulator spring 226 can be disposed within the control chamber 206, but may be disposed in the supply chamber 204 in other embodiments. The regulator spring 226 in this embodiment may be a coil spring that is coaxial with the stem 224. The regulator spring 226 may bias the piston 222 against an ambient pressure 228 in the control chamber 206.

In some embodiments, the housing 201 may be formed from two components. For example, the housing 201 may be formed from a lower housing 201a and an upper housing 201b, as shown in the illustrative embodiment of FIGS. 2A-2B. In this example, the lower housing 201a and the upper housing 201b each include an end wall, a side wall adjoining the end wall, and an open end opposite the end wall. Either the lower housing 201a or the upper housing 201b may have an outside dimension less than an inside dimension of the other so that one may be inserted into the other to form a structure that provides a substantially closed interior. In some embodiments, the lower housing 201a and the upper housing 201b may be engaged to allow relative movement between them. In more particular embodiments, the lower housing 201a and the upper housing 201b may each have cylindrical side walls and rounded end walls.

The charging chamber 202 may be generally defined by adjoining walls of the housing 201, such as an end wall of the housing 201, a side wall or walls of the housing 201, and a partition within the housing 201, such as the chamber wall 207a. The supply chamber 204 may also be generally defined by adjoining walls within the housing 201. For example, the supply chamber 204 in FIGS. 2A-2B can be generally defined by the chamber wall 207a, a side wall or walls of the housing 201, and another partition, such as the chamber wall 207b. The control chamber 206 may be similarly described, for example, as a chamber defined by the chamber wall 207b, the side wall or walls of the housing 201, and another end wall of the housing 201. In this example embodiment, the charging chamber 202 and the supply chamber 204 may have a common wall, such as the chamber wall 207a, for example. The supply chamber 204 and the control chamber 206 may also have a common wall, such as the chamber wall 207b, for example. The charging chamber 202 and the supply chamber 204 may be fluidly isolated from each other except through the charging port 205. The charging chamber 202 and the supply chamber 204 may be fluidly isolated from the ambient environment. And the control chamber 206 may be fluidly isolated from the charging chamber 202 and the supply chamber 204.

The regulator valve 220 in this example can be disposed partially within the control chamber 206 and partially within the supply chamber 204, with circumferential edges of the piston 222 abutting or engaging the side wall or walls of the control chamber 206. The interface between the piston 222 and the walls of the control chamber 206 may also provide a fluid seal, dividing the control chamber 206 into a region of the ambient pressure 228 and a region of control pressure 230. However, the regulator valve 220 may also reciprocate within the control chamber 206 while maintaining the fluid seal. For example, the regulator valve 220 may additionally include flexible o-rings disposed between the piston 222 and the side wall of the control chamber 206, and the o-rings may be lubricated so that the regulator valve 220 can reciprocate within the control chamber 206.

In operation, pressure in the supply chamber 204 can be distributed to a remote chamber, environment, or other location through the supply port 212. For example, pressure in the supply chamber 204 may be distributed to a controlled environment, such as a sealed therapeutic environment associated with the reduced-pressure therapy system 100. The control pressure 230 in the control chamber 206 can be equalized with the pressure in the remote location through the control port 214. In reduced-pressure therapy applications, the control pressure 230 should be less than the ambient pressure 228, resulting in a pressure differential across the regulator valve 220. To simplify further description, the force on the regulator valve 220 resulting from the pressure differential on opposing sides of the piston 222 may be referred to as a "differential force." The regulator spring 226 also generally exerts a force on the regulator valve 220. In expected operating ranges, the force of the regulator spring 226 is directly proportional to a displacement of the ends of the regulator spring 226 from a relaxed position. Thus, if the control pressure 230 is less than the ambient pressure 228, the differential force on the piston 222 tends to compress the regulator spring 226 and, consequently, the force of the regulator spring 226 opposes the differential force. The differential force and the force of the regulator spring 226 can be combined to determine a net force acting on the regulator valve 220. The net force can cause the regulator valve 220 to move reciprocally within the control chamber 206, such as along a central axis 231 aligned with the charging port 205.

The regulator spring 226 may be selected, adjusted, modified, tuned, or otherwise calibrated so that the control pressure 230 must drop below a threshold value (such as a target pressure) before the net force can move the regulator valve 220 into a position that closes the charging port 205. In some embodiments, for example, the piston 222 may rotate within the housing 201 to adjust the compression of the regulator spring 226. In the illustrative embodiment of FIGS. 2A-2B, the piston 222 includes a boss 232 that can be rigidly mated with a sleeve 234 of the upper housing 201b, and the stem 224 may be threaded or have a threaded portion engaged to the boss 232. The stem 224 may be locked radially with the housing 201 with a keyed feature. In such embodiments, the piston 222 and the sleeve 234 are generally locked radially, and compression of the regulator spring 226 may be adjusted by rotating the upper housing 201b, which can cause the piston 222 to rotate relative to the stem 224. The change in compression of the regulator spring 226 results in a change to the force of the regulator spring 226 acting on the regulator valve 220, and thus, a change in the threshold value of the control pressure 230 needed to actuate the regulator valve 220. In many applications, this threshold value of the control pressure 230 should generally correlate to a target pressure prescribed for reduced-pressure therapy, and may be referred to herein as the "therapy pressure" or "therapeutic pressure." Thus, in some embodiments, the therapy pressure may be adjusted by rotating the upper housing 201b. In yet more particular embodiments, the upper housing 201b may be calibrated to indicate various levels of the therapy pressure.

Thus, the charging chamber 202 may be charged to reduce the pressure in the charging chamber 202, and the pressure in the therapeutic environment may be regulated based on a differential between the therapy pressure and the control pressure 230. For example, the pressure may be regulated by balancing the force of the regulator spring 226 and a differential force. A differential force on the piston 222 may be produced by a pressure differential across the piston 222, such as the differential between the control pressure 230 on one side of the piston 222 and ambient pressure 228 on an opposing side of the piston 222, for example. For reduced-pressure therapy applications, the charging chamber 202 may be charged to a pressure lower than the therapy pressure. In some embodiments, for example, the desired therapy pressure may be about −125 mm Hg and pressure in the charging chamber 202 may be reduced to a pressure of about −150 mm Hg.

If the regulator valve 220 is calibrated to a particular therapy pressure and the control pressure 230 is higher than the therapy pressure, the force of the regulator spring 226 should exceed the differential force, and the net force should actuate the regulator valve 220, moving the regulator valve 220 into an open position (see FIG. 2B) in which the stem 224 disengages from the charging port 205. Disengagement of the stem 224 from the charging port 205 may also be referred to as opening the charging port 205. Pressure between the charging chamber 202 and the supply chamber 204 can equalize through the open charging port 205. As the pressure in the charging chamber 202 and the supply chamber 204 continues to equalize, the pressure in the supply chamber 204 continues to decrease. Unless there is a complete blockage in the fluid path between the supply chamber 204 and the therapeutic environment, pressure in the therapeutic environment also decreases and equalizes with the pressure in the supply chamber 204 through the supply lumen 216a. And unless there is a complete obstruction in the fluid path between the therapeutic environment and the control chamber 206, the control pressure 230 also decreases and equalizes with the pressure in the therapeutic environment through the feedback lumen 216b. As the control pressure 230 decreases and approaches the therapy pressure, the differential force increases until it exceeds the force of the regulator spring 226, causing the stem 224 to engage the charging port 205. Engagement of the stem 224 with the charging port 205 can substantially reduce or prevent fluid communication between the charging chamber 202 and the supply chamber 204 through the charging port 205, as shown in the illustrative embodiment of FIG. 2A. The engagement of the stem 224 with the charging port 205 may also be referred to as closing the charging port 205. The charging port 205 generally remains open until the control pressure 230 is less than or substantially equal to the therapy pressure. Advantageously, the regulator valve 220 can keep the charging port 205 open to compensate for pressure drops and partial blockages, particularly in the fluid path between the supply chamber 204 and a controlled environment, because pressure in the controlled environment can be directly measured by feedback lumen 216b.

Figure 3A:
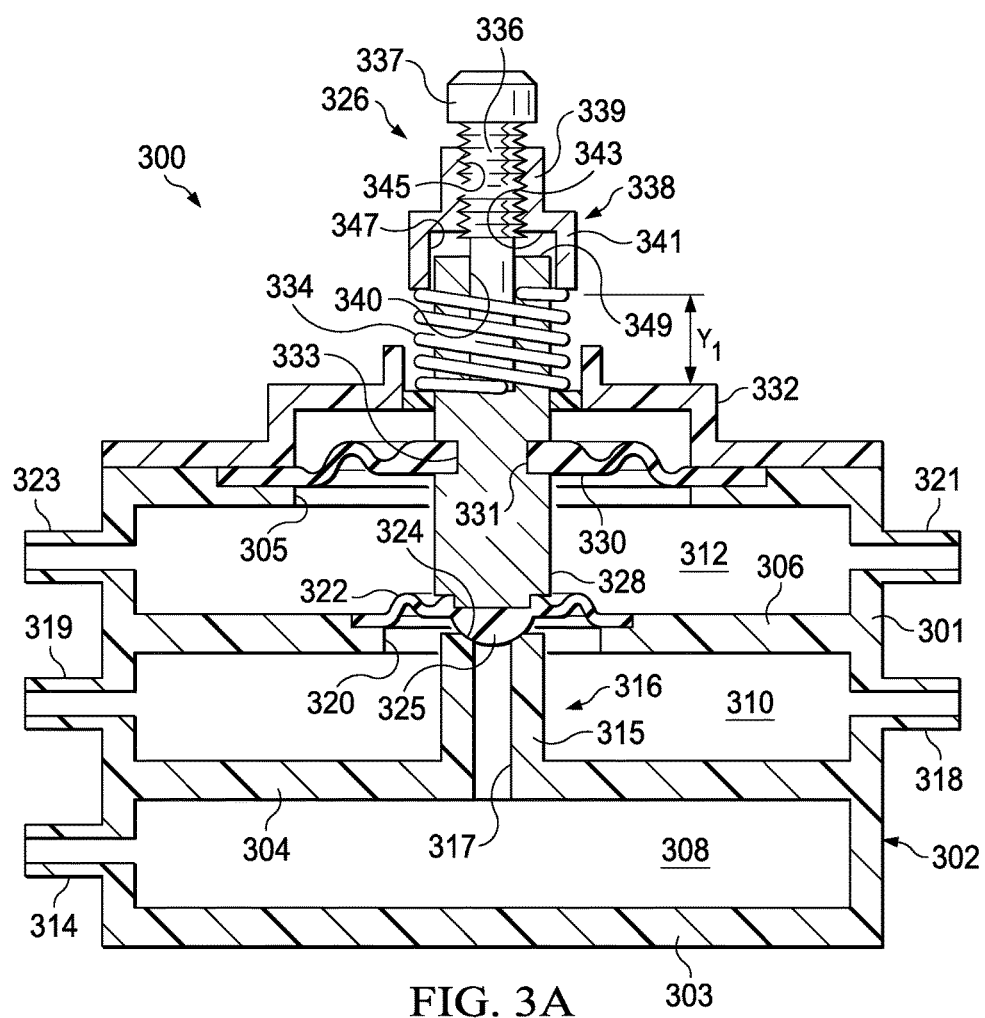
FIG. 3A is a schematic cross-section of another embodiment of a regulator for use with a reduced-pressure therapy system.

FIG. 3A is a cross-sectional view illustrating a regulator 300 that may be associated with some embodiments of the reduced-pressure therapy system 100. The regulator 300 is another example embodiment of the regulator 106. The regulator 300 may be similar to the regulator 200 of FIGS. 2A-2B in many respects, and may include a housing 302 and a regulator valve 326. The housing 302 may have an end wall 303, one or more side walls 301, and an open end 305 opposite the end wall 303. The side walls 301 may be coupled to peripheral portions of and generally perpendicular to the end wall 303.

The housing 302 may be partitioned by a first wall 304 and a second wall 306 to form a charging chamber 308, a supply chamber 310, and a control chamber 312. In some embodiments, the charging chamber 308 may adjoin the supply chamber 310, disposed between the end wall 303, the first wall 304, and the side walls 301. The supply chamber 310 may be disposed between the charging chamber 308 and the control chamber 312. For example, in FIG. 3A, the first wall 304 separates the charging chamber 308 and the supply chamber 310. The supply chamber 310 may be bounded by the first wall 304, the side walls 301, and the second wall 306. The control chamber 312 may adjoin the supply chamber 310, as shown in the illustrative embodiment of FIG. 3A. For example, the second wall 306 may separate the supply chamber 310 and the control chamber 312. The supply chamber 310 may be bounded by the second wall 306, the side walls 301, and the open end 305 of the housing 302. The first wall 304 and the second wall 306 may be coupled to the side walls 301 of the housing 302 at peripheral portions of the first wall 304 and the second wall 306. In some embodiments, no fluid communication may occur between the charging chamber 308, the supply chamber 310, and the control chamber 312 at the locations where the first wall 304 and the second wall 306 couple to the housing 302.

The housing 302, the first wall 304, and the second wall 306 may be formed of a material having a sufficient strength to resist collapse if a reduced pressure is supplied to the charging chamber 308, the supply chamber 310, and the control chamber 312, such as metals, hard plastics, or other suitable materials. For example, the housing 302, the first wall 304, and the second wall 306 may resist collapse if a reduced pressure of about 150 mm Hg (−150 mm Hg gauge pressure) is supplied to the charging chamber 308, the supply chamber 310, or the control chamber 312. In other exemplary embodiments, the housing 302, the first wall 304, and the second wall 306 may resist collapse if a reduced pressure of about 600 mm Hg (−600 mm Hg gauge pressure)

is supplied to the charging chamber 308, the supply chamber 310, or the control chamber 312.

The charging chamber 308 may include a source port 314 and a charging port 316. The source port 314 may be disposed in one of the side walls 301 of the charging chamber 308 and may be fluidly coupled to the charging chamber 308. In some embodiments, the source port 314 may be configured to be fluidly coupled to a supply of reduced pressure, such as an electric pump, a manual pump, or wall-suction source, for example. In some embodiments, the source port 314 may be fluidly coupled to a wall-suction source by a conduit or tube. A one-way valve may be disposed in the source port 314 and oriented to prevent fluid flow into the charging chamber 308 through the source port 314 and permit fluid flow out of the charging chamber 308 through the source port 314.

In some embodiments, the charging port 316 may be disposed in the first wall 304, as shown in the illustrative embodiment of FIG. 3A. The charging port 316 may fluidly couple the charging chamber 308 and the supply chamber 310. In some embodiments, the charging port 316 may have a cylindrical wall 315 and a central passage 317 that extends between the charging chamber 308 and the supply chamber 310. The cylindrical wall 315 may include a portion extending into the supply chamber 310 from the first wall 304 so that the charging port 316 terminates near a center portion of the second wall 306. In some embodiments, the charging port 316 may be disposed in other locations of the first wall 304.

The supply chamber 310 may include a supply port 318 and a monitor port 319. In some embodiments, the supply port 318 may be fluidly coupled to the supply chamber 310 and provide an interface to the supply chamber 310. For example, the supply port 318 may be configured to be coupled to a tube, which can be coupled to a dressing or other upstream component. A one-way valve may be disposed in the supply port 318 and oriented to permit fluid flow into the supply chamber 310 through the supply port 318 and prevent fluid flow out of the supply chamber 310 through the supply port 318.

The monitor port 319 may also be fluidly coupled to the supply chamber 310, providing a second interface to the supply chamber 310. In some embodiments, for example, the monitor port 319 may be disposed in one of the side walls 301, opposite the supply port 318. In other embodiments, the monitor port 319 may be proximate to or adjacent to the supply port 318. The monitor port 319 may be fluidly coupled to a monitoring device, such as a sensor, feedback interface, or overpressure valve, for example. In some embodiments, the monitor port 319 may be capped so that no fluid communication may occur through the monitor port 319.

The control chamber 312 may include a control port 321 and a monitor port 323. In some embodiments, the control port 321 may be fluidly coupled to the control chamber 312 and provide an interface to the control chamber 312. In some embodiments, the control port 321 may be disposed on a same side of the regulator 300 as the supply port 318. In still other embodiments, the control port 321 may be vertically aligned with the supply port 318. In the illustrative embodiment of FIG. 3A, the control port 321 may be configured to be coupled to a tube, which can be coupled to a dressing or other upstream component. A one-way valve may be disposed in the control port 321 and oriented to prevent fluid flow into the control chamber 312 through the control port 321 and permit fluid flow out of the control chamber 312 through the control port 321.

The monitor port 323 may also be fluidly coupled to the control chamber 312. In some embodiments, the monitor port 323 may be opposite the control port 321. In other embodiments, the monitor port 323 may be disposed on a same side of the regulator 300 as the control port 321. In other embodiments, the monitor port 323 may be vertically aligned with the monitor port 319. The monitor port 323 may be fluidly coupled to a monitoring device, such as a sensor, a feedback interface, or an overpressure valve, for example. In some embodiments, the monitor port 323 may be capped so that no fluid communication may occur through the monitor port 323.

The second wall 306 may include an opening 320 in a center portion proximate to the distal end of the charging port 316. As illustrated in FIG. 3A, the opening 320 may be axially aligned with the central passage 317. The opening 320 may be larger than the distal end of charging port 316, providing a gap between a peripheral portion of the opening 320 and the distal end of the charging port 316. The gap provides a fluid path between the charging port 316 and the supply chamber 310. In some embodiments, the gap between the peripheral portion of the opening 320 and the distal end of the charging port 316 may be about 0.5 mm. In other embodiments, the gap between the peripheral portion of the opening 320 and the distal end of the charging port 316 may be less than 0.5 mm. In yet other alternative or additional embodiments, the distal end of the charging port 316 may be vertically separated from the second wall 306. For example, the distal end of the charging port 316 may be vertically separated from a lower surface of the second wall 306 a distance of about 0.5 mm. In other embodiments, the distance separating the distal end of the charging port 316 and the lower surface of the second wall 306 may be greater than 0.5 mm.

The regulator valve 326 can be operably associated with the charging port 316 to regulate fluid communication between the charging chamber 308 and the supply chamber 310. The regulator valve 326 can be biased to either open or close the charging port 316. In some embodiments, the regulator valve 326 may be coupled to the open end 305 of the housing 302, as illustrated in FIG. 3A. The regulator valve 326 may be coupled to ends of the side walls 301 of the housing 302, opposite the end wall 303 of the housing 302. In some embodiments, the regulator valve 326 may substantially limit or prevent fluid communication through the open end 305 of the housing 302. The regulator valve 326 may include a valve member 322, a valve body, such as a stem 328, and an actuator 330. The regulator valve 326 may also include a regulator cap 332, a regulator spring 334, an adjustment shaft 336, and a tension adjuster, such as a push button, a lever, or a dial 338.

Figure 3B:
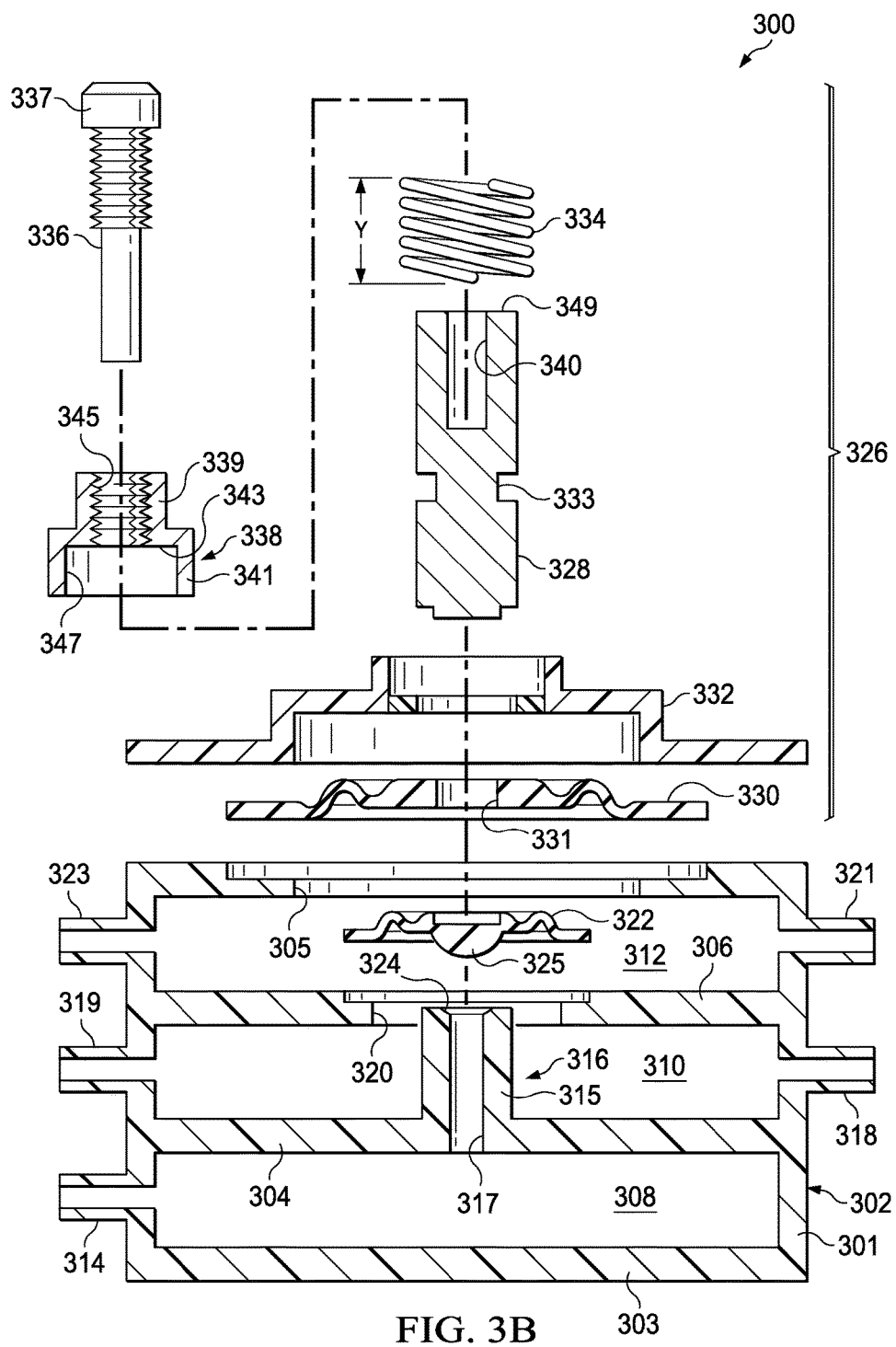
FIG. 3B is a sectional exploded view of the regulator of FIG. 3A.

FIG. 3B is a schematic sectional assembly view of the regulator 300 illustrating additional details that may be associated with some embodiments. In some embodiments, the valve member 322 may be a flexible membrane, such as a diaphragm. In some embodiments, the valve member 322 may have a generally disc-like shape with a diameter larger than the diameter of the opening 320 in the second wall 306. In other embodiments, the valve member 322 may have a shape matched to a shape of the opening 320, for example, square, rectangular, ovoid, triangular, or amorphous shapes. The valve member 322 may have peripheral portions coupled to the second wall 306, and the valve member 322 may extend across the opening 320. If the valve member 322 is coupled to the second wall 306, the valve member 322 may fluidly isolate the control chamber 312 from the supply chamber 310. For example, a difference in the pressures in the supply chamber 310 and the control chamber 312 may cause deflection of the valve member 322. In some embodiments, the valve member 322 may be formed from a silicone material. In some embodiments, the valve member 322 may have a hardness rating between about 30 Shore A and about 50 Shore A.

As illustrated in FIG. 3B, some embodiments of the charging port 316 may have a valve seat 324 on the distal end. The valve seat 324 may provide a tapered or beveled edge proximate to the central passage 317 of the charging port 316. In some embodiments, the valve member 322 may include an enlarged portion 325 configured to engage the valve seat 324. For example, the valve member 322 may be positioned so that the enlarged portion 325 of the valve member 322 may engage a beveled edge of the valve seat 324 of the charging port 316 in a closed position. If engaged in such a manner, can substantially prevent fluid communication through the central passage 317 of the charging port 316.

The stem 328 may be cylindrical and have an end coupled to the valve member 322. In some embodiments, a first end of the stem 328 may be coupled to the enlarged portion 325 of the valve member 322. The stem 328 is elongated so that the stem 328 may extend through the open end 305 if the end of the stem 328 is coupled to the valve member 322. A second end of the stem 328 may include a cavity 340. The cavity 340 may be a recess into the stem 328 from the second end of the stem 328. The cavity 340 may have a diameter less than a diameter of the stem 328 so that a shoulder 349 may be formed at the end of the stem 328 adjacent to an opening of the cavity 340. The shoulder 349 may face away from the housing 302. The stem 328 may also have a recess 333 disposed between ends of the stem 328. In some embodiments, the recess 333 is annular and may be disposed proximate to a center of a length of the stem 328.

The actuator 330 may be coupled to the housing 302 so that the actuator 330 covers the open end 305. In some embodiments, the actuator 330 extends across the open end 305 to fluidly isolate the control chamber 312 from the ambient environment. In some embodiments, the actuator 330 may be a diaphragm having peripheral portions coupled to the ends of the side walls 301 of the housing 302. The actuator 330 may have an elasticity permitting a center portion of the actuator 330 to deflect from an equilibrium position while the peripheral portions of the actuator 330 remain affixed to the housing 302. In some embodiments, the actuator 330 may be formed of an elastomeric material. For example, the actuator 330 may be formed of a silicone. In some embodiments, the actuator 330 may be formed from a material having a hardness rating between about 30 Shore A and about 50 Shore A.

The actuator 330 may have an opening 331 proximate to a center portion of the actuator 330. The opening 331 may receive the stem 328 so that the stem 328 extends through the actuator 330. In some embodiments, the actuator 330 may be coupled or otherwise sealed to the stem 328. For example, the actuator 330 may be welded to the stem 328 at the opening 331. For example, at least a portion of the actuator 330 adjacent the opening 331 may be inserted into the recess 333 to couple the actuator 330 to the stem 328. In some embodiments, movement of the stem 328 along an axis of the stem 328 causes movement of the center portion of the actuator 330, and movement of the actuator 330 along an axis of the stem 328 may cause movement of the stem 328.

If assembled, as shown in FIG. 3A, the regulator cap 332 may be coupled to the housing 302 so that the regulator cap 332 is adjacent to the control chamber 312 and the open end 305. In some embodiments, the regulator cap 332 covers the open end 305 of the housing 302 and includes a raised portion extending away from the control chamber 312 near a center of the regulator cap 332. In some embodiments, the raised portion may be coextensive with the open end 305 so that the regulator cap 332 may be separated from the actuator 330 near the open end 305. The stem 328 may extend through the raised portion of the regulator cap 332. The regulator cap 332 may be sealed to the stem 328. In some embodiments, the stem 328 may move relative to the regulator cap 332 while remaining sealed to the regulator cap 332. In other embodiments, the stem 328 may not be fluidly sealed to the regulator cap 332 so that an ambient pressure adjacent an exterior of the regulator cap 332 may be substantially equivalent to a pressure in the area between the raised portion of the regulator cap 332 and the actuator 330.

The regulator spring 334 may be disposed on the stem 328 so that the regulator spring 334 circumscribes the stem 328. The regulator spring 334 may have a first end adjacent to the regulator cap 332. In some embodiments, the first end of the regulator spring 334 may contact the regulator cap 332 so that the regulator spring 334 may be compressed against the regulator cap 332. A second end of the regulator spring 334 may be adjacent to the end of the stem 328 that has the cavity 340 disposed therein. The regulator spring 334 may have a length Y in a relaxed position, as shown in FIG. 3B. In the relaxed position, the regulator spring 334 may be neither extended nor compressed so that the regulator spring 334 does not exert a spring force. In some embodiments, a length Y1 may be the length of the regulator spring 334 in a compressed position, as shown in FIG. 3A, for example if the regulator valve 326 blocks fluid communication through the charging port 316.

The adjustment shaft 336 may have an end disposed within the cavity 340 and may be coupled to the stem 328 so that the adjustment shaft 336 and the stem 328 can move as integral members. The adjustment shaft 336 may be cylindrical and have an enlarged distal end forming an adjustment cap 337 of the adjustment shaft 336. A portion of the adjustment shaft 336 may be threaded between the adjustment cap 337 and the end disposed within the cavity 340. In some embodiments, the adjustment shaft 336 may be threaded between the adjustment cap 337 and an opening of the cavity 340 of the stem 328.

The dial 338 may be a tubular body having a first portion 339 and a second portion 341. The first portion 339 may have a cavity 345, and the cavity 345 has a width or diameter substantially equal to the outer diameter of the threaded portion of the adjustment shaft 336. The second portion 341 may also have a cavity 347, the width or diameter of the cavity 347 may be substantially equal to the outer diameter of the stem 328. The first portion 339 and the second portion 341 are preferably joined, in the illustrative embodiment of FIG. 3A, forming a shoulder 343 between the cavity 345 and the cavity 347. The dial 338 can be disposed on the stem 328 so that the shoulder 343 faces the cavity 340. As shown in the illustrative embodiment of FIG. 3A, the shoulder 343 may have an annular width substantially equal to the width of a shoulder 349 of the stem 328 formed by the cavity 340. The dial 338 may be moveably coupled to the adjustment shaft 336 proximate to the adjustment cap 337 of the adjustment shaft 336. In some embodiments, the first portion 339 of the dial 338 is adjacent to the adjustment cap 337 of the adjustment shaft 336. In some embodiments, the surface of the cavity 345 of the first portion 339 may be threaded. The dial 338 may be threaded to the adjustment shaft 336, allowing the dial 338 to be rotated about the adjustment shaft 336. Rotation of the dial 338 about the adjustment shaft 336 may cause the dial 338 to move parallel to an axis of the adjustment shaft 336. In this manner, the dial 338 may be moved along the adjustment shaft 336.

Figure 3C:
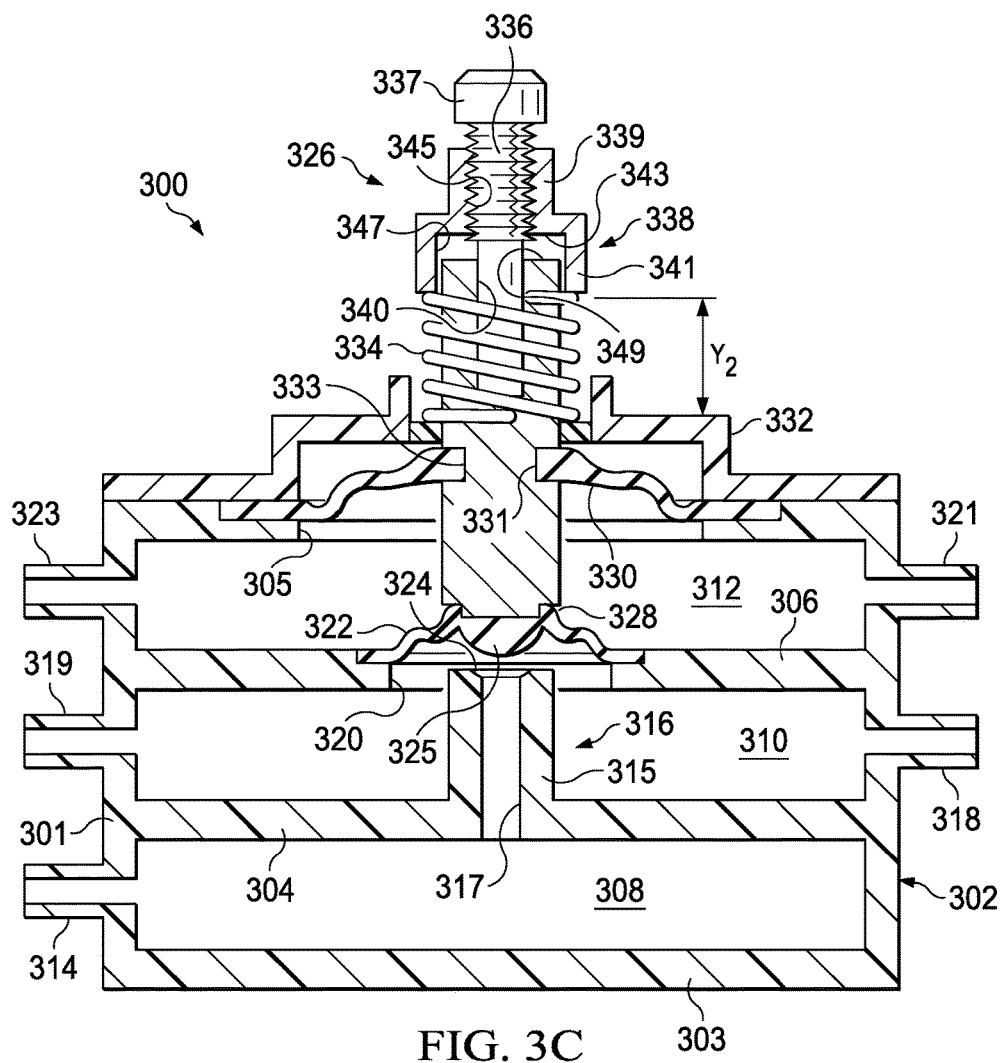
FIG. 3C is a schematic cross-section of the regulator of FIG. 3A having a regulator valve in an open position.

FIG. 3C is a schematic sectional view of the regulator 300 illustrating additional details that may be associated with some embodiments of the regulator 300 in an open position. The dial 338 may be positioned on the adjustment shaft 336 so that an end of the second portion 341 of the dial 338 contacts the distal end of the regulator spring 334. For example, the dial 338 may be threaded onto the adjustment shaft 336, and additional rotation of the dial 338 relative to the adjustment shaft 336 may move the dial 338 axially closer to the regulator cap 332 to compress the regulator spring 334. Compression of the regulator spring 334 by the dial 338 shortens the length of the regulator spring 334. This compression may cause the regulator spring 334 to exert a force on the dial 338 urging the dial 338 away from the regulator cap 332. In some embodiments, the regulator spring 334 may have a length Y2 if the regulator spring 334 is compressed by the dial 338. The force exerted by the regulator spring 334 is directly proportional to the displacement of the regulator spring 334 from the relaxed position. The force exerted by the regulator spring 334 on the dial 338 similarly urges the adjustment shaft 336, the coupled stem 328, and the coupled valve member 322 upward. In some embodiments, the force also urges the valve member 322 away from the charging port 316 into an open position. In the open position, fluid communication may occur through the charging port 316.

A differential force may also operate on the actuator 330. The differential force may be a force generated by a difference in pressures between the control chamber 312 and the ambient environment of the regulator 300. The pressure in the control chamber 312 may also be referred to as a control pressure. If the control pressure in the control chamber 312 and the pressure in the ambient environment are substantially equal, the differential force may be approximately zero. If the control pressure in the control chamber 312 is less than the ambient pressure, for example, if the regulator 300 is being used to provide reduced-pressure therapy, the differential force may act to urge the actuator 330, the coupled stem 328, and the valve member 322 toward the distal end of the charging port 316.

If the differential force is greater than the force of the regulator spring 334 acting on the stem 328, the valve member 322 may be urged into contact with the distal end of the charging port 316 to prevent fluid communication through the charging port 316 in a closed position, as shown in FIG. 3A. If the differential force is less than the force on the regulator spring 334, the valve member 322 may be urged away from the distal end of the charging port 316 to permit fluid communication through the charging port 316 in the open position, shown in FIG. 3C. The dial 338 can be threaded down the adjustment shaft 336 to control the compression of the regulator spring 334 from the relaxed position Y. Thus, the compression of the regulator spring 334 can be controlled to select a prescribed therapy, so that the force of the regulator spring 334 may be overcome if the therapy pressure is reached in the control chamber 312.

In other embodiments, a differential force may act on the valve member 322. For example, the supply pressure in the supply chamber 310 may exert a force on the valve member 322, and the control pressure in the control chamber 312 may exert a force on the valve member 322. The sum of the forces acting on the valve member 322 may be referred to as a valve force. The valve force may urge the valve member 322 into or out of contact with the charging port 316. In some embodiments, the valve force may act in opposition to the differential force acting on the actuator 330. The relative dimensions of the valve member 322 and the actuator 330 may be selected so that the actuator 330 is several times larger than the valve member 322. For example, the actuator 330 may have a major dimension that is greater than a corresponding dimension of the valve member 322. In some embodiments, the actuator 330 may have a diameter that is greater than a diameter of the valve member 322. A large difference in size between the actuator 330 and the valve member 322 correlates to a similarly large difference in the surface areas of the actuator 330 and the valve member 322. The larger surface area of the actuator 330 allows the differential force acting on the actuator 330 to act over a larger area than the valve force acting on the valve member 322. As a result, the differential force acting on the actuator 330 may overcome other forces acting on other components of the regulator 300, such as the valve member 322, allowing the actuator 330 to control the movement of the stem 328. In some embodiments, the opening 320 may be made smaller than depicted, and the charging port 316 may be further separated from the lower surface of the second wall 306. In such an embodiment, the valve member 322 may be made relatively smaller so that the valve force acts on a smaller surface area than the differential force.

Figure 3D:
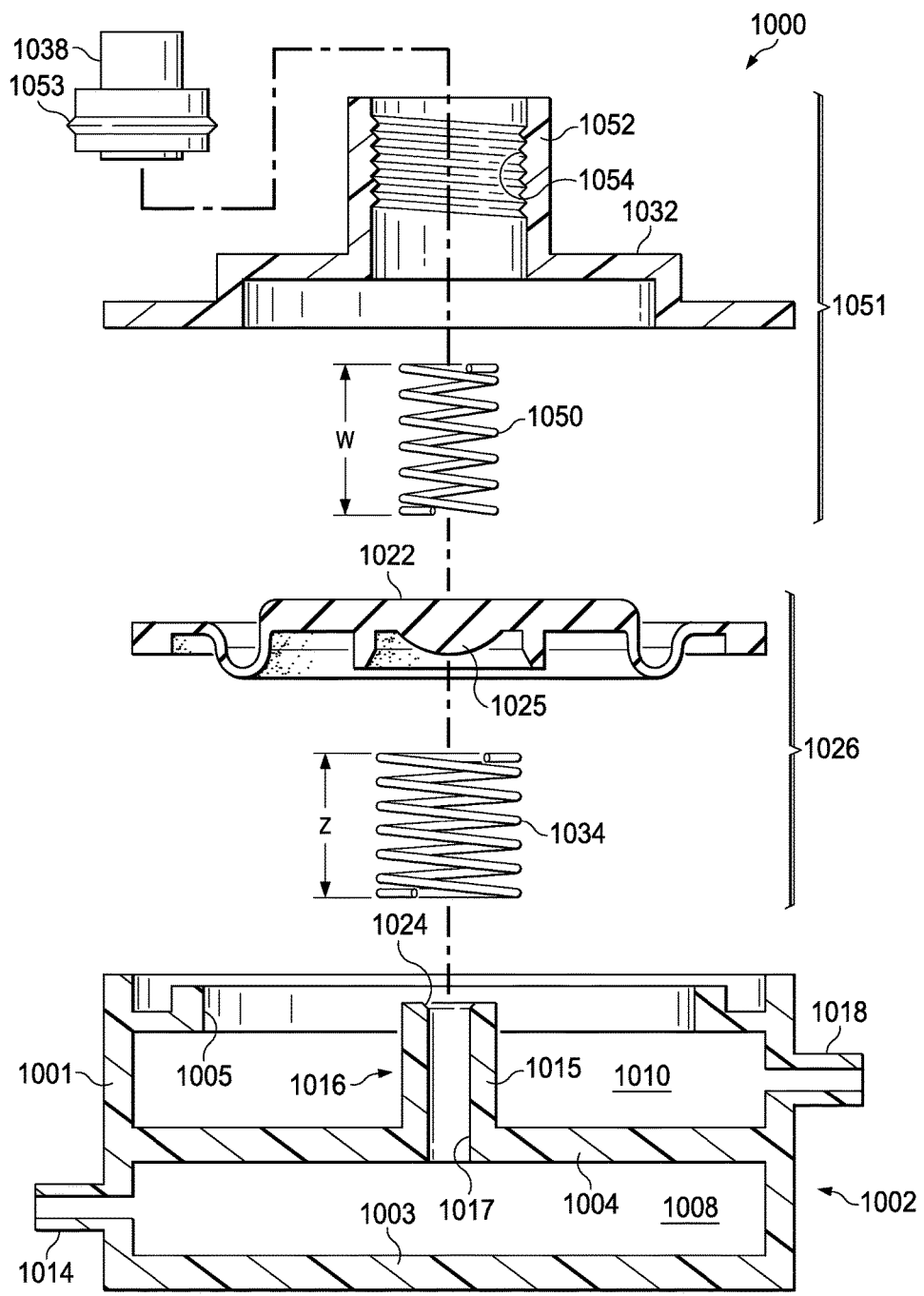
FIG. 3D is a sectional exploded view of another embodiment of a regulator for use with a reduced-pressure therapy system.

FIG. 3D is a cross-sectional exploded view, illustrating a regulator 1000 that may be associated with some embodiments of the reduced-pressure therapy system 100. The regulator 1000 is another example embodiment of the regulator 106. The regulator 1000 may be similar to the regulator 200 of FIGS. 2A-2B and the regulator 300 of FIGS. 3A-3C in many respects, and may include a housing 1002, a regulator valve 1026, and a valve calibrator 1051. The housing 1002 may have an end wall 1003, one or more side walls 1001, and an open end 1005 opposite the end wall 1003. The side walls 1001 may be coupled to peripheral portions of and generally perpendicular to the end wall 1003.

The housing 1002 may be partitioned by a wall 1004 to form a charging chamber 1008 and a supply chamber 1010. In some embodiments, the charging chamber 1008 may adjoin the supply chamber 1010, being disposed between the end wall 1003, the wall 1004, and the side walls 1001. The supply chamber 1010 may be disposed between the charging chamber 1008 and the open end 1005. For example, in FIG. 3D, the wall 1004 separates the charging chamber 1008 and the supply chamber 1010. The supply chamber 1010 may be bounded by the wall 1004, the side walls 1001, and the open end 1005. The wall 1004 may be coupled to the side walls 1001 of the housing 1002 at peripheral portions of the wall 1004. In some embodiments, no fluid communication may occur between the charging chamber 1008, and the supply chamber 1010 at the locations where the wall 1004 couples to the housing 1002.

The housing 1002 and the wall 1004 may be formed of a material having a sufficient strength to resist collapse if a reduced pressure is supplied to the charging chamber 1008 and the supply chamber 1010, such as metals, hard plastics, or other suitable materials. For example, the housing 1002 and the wall 1004 may resist collapse if a reduced pressure of about 150 mm Hg (−150 mm Hg gauge pressure) is supplied to the charging chamber 1008 and the supply chamber 1010. In other exemplary embodiments, the housing 1002 and the wall 1004 may resist collapse if a reduced pressure of about 600 mm Hg (−600 mm Hg gauge pressure) is supplied to the charging chamber 1008 and the supply chamber 1010.

The charging chamber 1008 may include a source port 1014 and a charging port 1016. The source port 1014 may be disposed in one of the side walls 1001 of the charging chamber 1008 and may be fluidly coupled to the charging chamber 1008. In some embodiments, the source port 1014 may be configured to be fluidly coupled to a supply of reduced pressure, such as an electric pump, a manual pump, or wall-suction source, for example. In some embodiments, the source port 1014 may be fluidly coupled to a wall-suction source by a conduit or tube. A one-way valve may be disposed in the source port 1014 and oriented to prevent fluid flow into the charging chamber 1008 through the source port 1014 and permit fluid flow out of the charging chamber 1008 through the source port 1014.

In some embodiments, the charging port 1016 may be disposed in the wall 1004, as shown in the illustrative embodiment of FIG. 3D. The charging port 1016 may fluidly couple the charging chamber 1008 and the supply chamber 1010. In some embodiments, the charging port 1016 may have a cylindrical wall 1015 and a central passage 1017 that extends between the charging chamber 1008 and the supply chamber 1010. The cylindrical wall 1015 may include a portion extending into the supply chamber 1010 from the wall 1004 so that the charging port 1016 terminates near a center portion of the open end 1005. In some embodiments, the charging port 1016 may be disposed in other locations of the wall 1004. In some embodiments, the charging port 1016 may have a valve seat 1024 on the distal end. The valve seat 1024 may provide a tapered or beveled edge proximate to the central passage 1017 of the charging port 1016.

The supply chamber 1010 may include a supply port 1018. In some embodiments, the supply port 1018 may be fluidly coupled to the supply chamber 1010 and provide an interface to the supply chamber 1010. For example, the supply port 1018 may be configured to be coupled to a tube, which can be coupled to a dressing or other upstream component. A one-way valve may be disposed in the supply port 1018 and oriented to permit fluid flow into the supply chamber 1010 through the supply port 1018 and prevent fluid flow out of the supply chamber 1010 through the supply port 1018.

In some embodiments, the open end 1005 may provide a fluid path between the charging port 1016 and the supply chamber 1010, which may be controlled by the regulator valve 1026. The regulator valve 1026 may include a valve member 1022 and a regulator spring 1034. The regulator valve 1026 can be coupled to the open end 1005 and operably associated with the charging port 1016 to regulate fluid communication between the charging chamber 1008 and the supply chamber 1010. The regulator valve 1026 can be biased to either open or close the charging port 1016. The regulator valve 1026 may be coupled to ends of the side walls 1001 of the housing 1002, opposite the end wall 1003 of the housing 1002. In some embodiments, the regulator valve 1026 may substantially limit or prevent fluid communication through the open end 1005 of the housing 1002.

In some embodiments, the valve member 1022 may be a flexible membrane, such as a diaphragm. In some embodiments, the valve member 1022 may have a generally disc-like shape with a diameter larger than the diameter of the open end 1005. In other embodiments, the valve member 1022 may have a shape matched to a shape of the open end 1005, for example, square, rectangular, ovoid, triangular, or amorphous shapes. The valve member 1022 may have peripheral portions coupled to the side walls 1001, and the valve member 1022 may extend across the open end 1005. If the valve member 1022 is coupled to the side walls 1001, the valve member 1022 may fluidly isolate the supply chamber 1010 from the ambient environment surrounding the regulator 1000. For example, a difference in the pressures in the supply chamber 1010 and the ambient environment may cause deflection of the valve member 1022. In some embodiments, the valve member 1022 may be formed from a silicone material. In some embodiments, the valve member 1022 may have a hardness rating between about 100 Shore A and about 50 Shore A.

In some embodiments, the valve member 1022 may include an enlarged portion 1025 configured to engage the valve seat 1024. The valve member 1022 may be positioned so that the enlarged portion 1025 of the valve member 1022 may engage a beveled edge of the valve seat 1024 of the charging port 1016 in a closed position. If engaged in such a manner, the valve member 1022 can substantially prevent fluid communication through the central passage 1017 of the charging port 1016.

The regulator spring 1034 may be disposed on the charging port 1016 so that the regulator spring 1034 circumscribes the charging port 1016. The regulator spring 1034 may have a first end adjacent to the wall 1004. In some embodiments, the first end of the regulator spring 1034 may contact the wall 1004 so that the regulator spring 1034 may be compressed against the wall 1004. A second end of the regulator spring 1034 may be adjacent to the distal end of the charging port 1016. The regulator spring 1034 may have a length Z if in a relaxed position. In the relaxed position, the regulator spring 1034 may be longer than the charging port 1016.

The valve calibrator 1051 may include a regulator cap 1032, a calibration spring 1050, and a knob 1038. The regulator cap 1032 may be coupled to the housing 1002 so that the regulator cap 1032 is adjacent to the supply chamber 1010 and the open end 1005. In some embodiments, the regulator cap 1032 covers the open end 1005 of the housing 1002 and includes a raised portion extending away from the supply chamber 1010 near a center of the regulator cap 1032. In some embodiments, the raised portion may be coextensive with the open end 1005 so that the regulator cap 1032 may be separated from the valve member 1022 near the open end 1005.

In some embodiments, the regulator cap 1032 may include a calibrator mount 1052. The calibrator mount 1052 may be a tubular portion coupled to the raised portion of the regulator cap 1032 and extending away from the supply chamber 1010. In some embodiments, the calibrator mount 1052 may be positioned on the regulator cap 1032 so that the calibrator mount 1052 is coaxial with the central passage 1017 of the charging port 1016. In other embodiments, the calibrator mount 1052 may not be coaxial with the central passage 1017 of the charging port 1016. The calibrator mount 1052 may have a thread 1054 formed on the inner surface of the calibrator mount 1052.

In some embodiments, the calibration spring 1050 may be disposed in the calibrator mount 1052. The calibration spring 1050 may have a diameter less than an inner diameter of the calibrator mount 1052 so that the calibration spring 1050 may move axially through the calibrator mount 1052. In some embodiments, an end of the calibration spring 1050 may contact the valve member 1022 on an opposite side of the valve member 1022 from the regulator spring 1034. The calibration spring 1050 may have a first end adjacent to the valve member 1022. In some embodiments, the first end of the calibration spring 1050 may contact the valve member 1022 on an opposite side of the valve member 1022 from the enlarged portion 1025, allowing the calibration spring 1050 to be compressed against the valve member 1022 opposite the regulator spring 1034. A second end of the calibration spring 1050 may extend into the calibrator mount 1052 and terminate adjacent to the thread 1054. The calibration spring 1050 may have a length W if in a relaxed position.

The knob 1038 may be a generally cylindrical body having a length and a diameter. In some embodiments, the diameter of the knob 1038 may be substantially equal to the inner diameter of the calibrator mount 1052. A thread 1053 may be formed on the outer surface of the knob 1038. The thread 1053 of the knob 1038 may be a mating thread to the thread 1054, allowing the knob 1038 to be threaded into the calibrator mount 1052. In some embodiments, the knob 1038 may be positioned with an end of the knob 1038 adjacent to or in contact with an end of the calibration spring 1050.

Figure 3E:
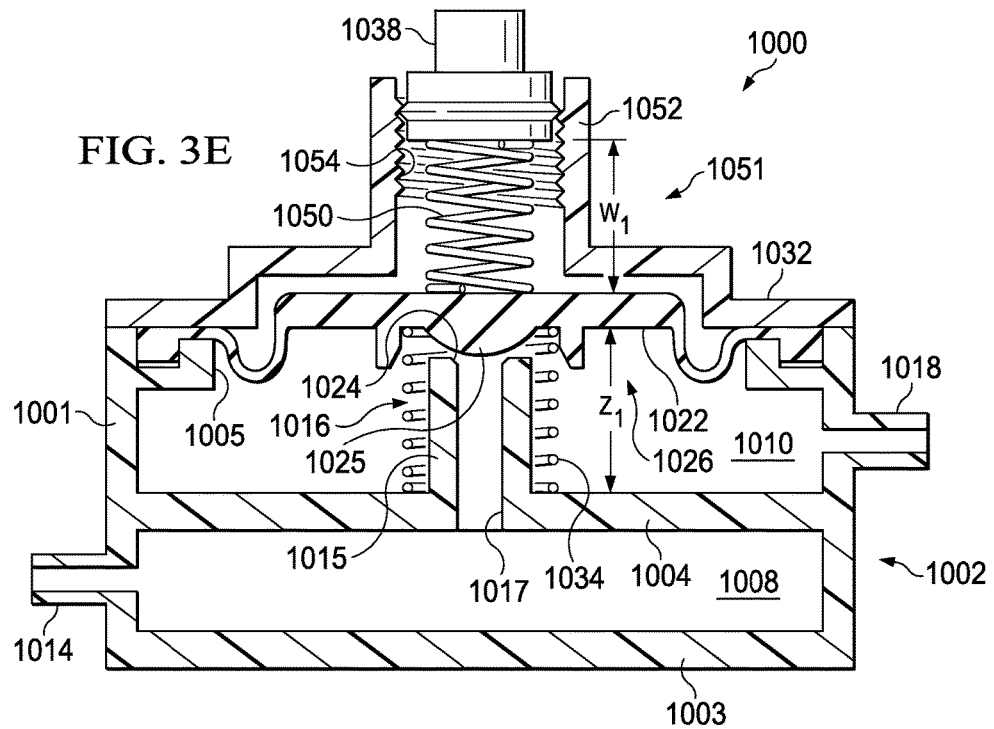
FIG. 3E is a schematic cross-section of the regulator of FIG. 3D having a regulator valve in an open position.

FIG. 3E is a schematic sectional view, illustrating additional details that may be associated with some embodiments of the regulator 1000 in an open position. In some embodiments, a differential force may operate on the valve member 1022. The differential force may be a force generated by a difference in pressures between the supply chamber 1010 and the ambient environment of the regulator 1000. The pressure in the supply chamber 1010 may also be referred to as a supply pressure or the manifold pressure. If the supply pressure in the supply chamber 1010 and the pressure in the ambient environment are substantially equal, the differential force may be approximately zero. If the supply pressure in the supply chamber 1010 is less than the ambient pressure, for example, if the regulator 1000 is being used to provide reduced-pressure therapy, the differential force may act to urge the valve member 1022 toward the distal end of the charging port 1016.

In some embodiments, the regulator spring 1034 may exert a force in response to movement of the regulator spring 1034 from the relaxed position. If the regulator spring 1034 is disposed in the supply chamber 1010, the regulator spring 1034 may be moved from the relaxed position so that the regulator spring 1034 has a length $Z_1$. If the regulator spring 1034 is compressed to the length $Z_1$, the regulator spring 1034 may exert a regulator force urging the valve member 1022 away from the valve seat 1024 of the charging port 1016. Generally, the regulator force exerted on the valve member 1022 may be proportional to a distance the regulator spring is moved from the relaxed position. Generally, the regulator spring 1034 may be selected so that the differential force may overcome the regulator force if the supply pressure is about the therapy pressure. If the differential force overcomes the regulator force, the valve member 1022 may contact the charging port 1016 and prevent fluid communication through the charging port 1016.

In some embodiments, the calibration spring 1050 may exert a force in response to movement of the calibration spring 1050 from the relaxed position. If the calibration spring 1050 is disposed in the calibrator mount 1052, the calibration spring 1050 may be moved from the relaxed position so that the calibration spring 1050 may have a length $W_1$. If the calibration spring 1050 is compressed to the length $W_1$, the calibration spring 1050 may exert a calibration force urging the valve member 1022 toward the valve seat 1024 of the charging port 1016. Generally, the force exerted on the valve member 1022 may be proportional to a distance the calibration spring 1050 is moved from the relaxed position. In some embodiments, the force of the regulator spring 1034 and the force of the calibration spring 1050 may urge the valve member 1022 in opposite directions.

In some embodiments, the calibration spring 1050 may exert a force that assists the differential force in urging the valve member 1022 into contact with the valve seat 1024 of the charging port 1016. The force exerted by the calibration spring 1050 may be used to calibrate the regulator 1000 to the desired therapy pressure. For example, the regulator 1000 may be tested to determine if the regulator 1000 supplies reduced pressure at a desired therapy pressure with no calibration force. If the regulator 1000 fails to provide the therapy pressure, the knob 1038 may be threaded further into the calibrator mount 1052 to increase the calibration force applied by the calibration spring 1050. In other embodiments, if the regulator 1000 has already been calibrated, the regulator 1000 may be tested to determine if the regulator 1000 supplies reduced pressure at a desired therapy pressure. If the regulator 1000 provides insufficient reduced pressure, the knob 1038 may be threaded out of the calibrator mount 1052 to decrease the calibration force applied by the calibration spring 1050, thereby increasing the required differential force to overcome the regulator force.

Figure 3F:
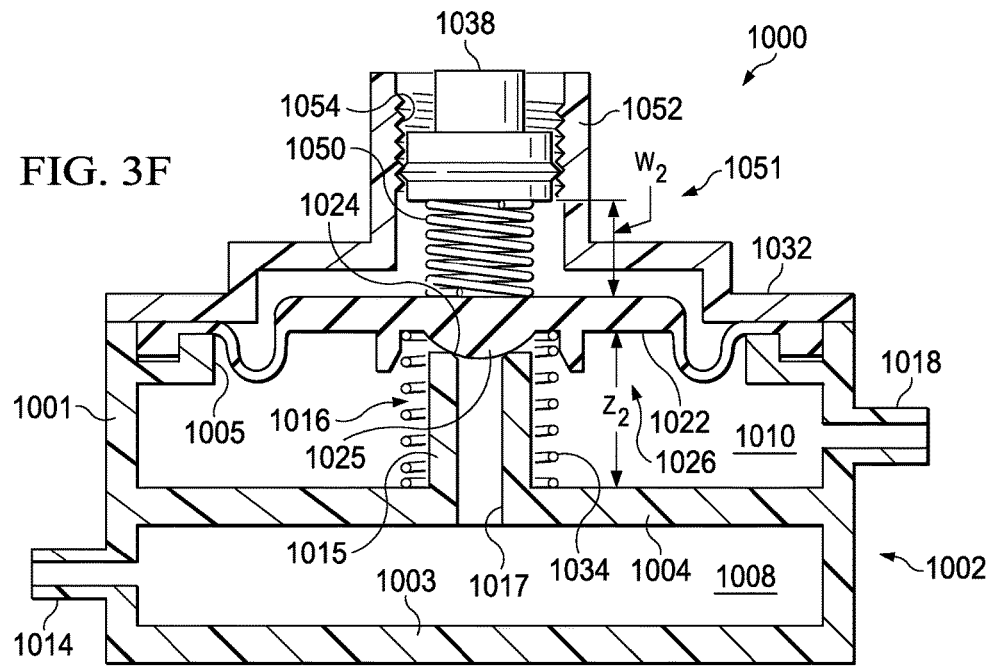
FIG. 3F is a schematic cross-section of the regulator of FIG. 3D having a regulator valve in a closed position.

FIG. 3F is a schematic sectional view, illustrating additional details of the regulator 1000 in a closed position. If the differential force plus the calibration force is greater than the force of the regulator spring 1034 acting on the valve member 1022, the valve member 1022 may be urged into contact with the distal end of the charging port 1016 to prevent fluid communication through the charging port 1016 in a closed position. In response, the regulator spring 1034 may be compressed to a length $Z_2$. If the differential force plus the calibration force is less than the force of the regulator spring 1034, the valve member 1022 may be urged away from the distal end of the charging port 1016 to permit fluid communication through the charging port 1016 in the open position, shown in FIG. 3E. The knob 1038 can be threaded down the thread 1054 to control the differential force required to overcome the regulator spring 1034. For example, if less reduced pressure is required, the knob 1038 may be threaded into the calibration mount 1052 so that the calibration spring 1050 has a length $W_2$. Thus, the displacement of the calibration spring 1050 can be controlled to calibrate the differential pressure, so that the force of the regulator spring 1034 may be overcome if the therapy pressure is reached in the supply chamber 1010.

Reduced-Pressure Therapy System

Figures 4A, 4B:
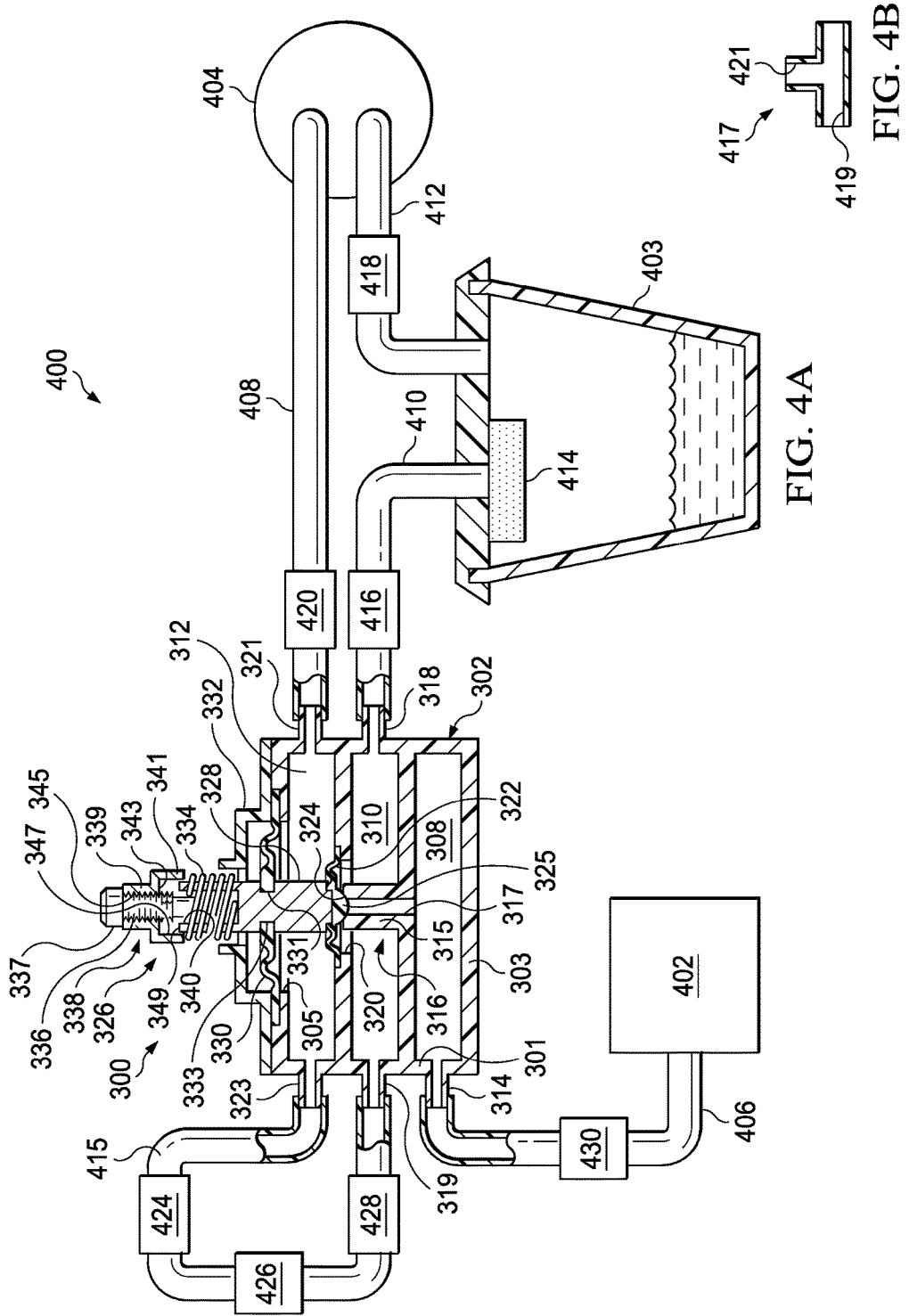
FIG. 4A is a schematic cross-section of an example embodiment of a reduced-pressure therapy system using the regulator of FIG. 3A.
FIG. 4B is a schematic cross-section of an example embodiment of an audible flow indicator that may be used with the reduced-pressure therapy system of FIG. 4A.

FIG. 4A is a schematic illustration of a reduced-pressure system 400 illustrating additional details that may be associated with the operation of the regulator 300. The reduced-pressure system 400 is an example embodiment of the reduced-pressure therapy system 100. The reduced-pressure system 400 includes a reduced-pressure source 402, a container 403, and a dressing 404. The reduced-pressure source 402 may be a wall-suction source, a manual pump, or an electric pump, for example. In some embodiments, the reduced-pressure source 402 may be a wall-suction source, and may be fluidly coupled to the source port 314. For example, a tube 406 may fluidly couple the reduced-pressure source 402 to the source port 314, as shown in the illustrative embodiment of FIG. 4A. The container 403 is an example embodiment of the container 112, and may be fluidly coupled to the supply port 318. In some embodiments, for example, a tube 410 may fluidly couple the container 403 to the supply port 318. The container 403 may include a filter, such as a hydrophobic filter 414 adjacent to an end of the tube 410. The dressing 404 is an example embodiment of the dressing 102, and may be fluidly coupled to the container 403. For example, a tube 412 may fluidly couple the dressing 404 to the container 403. The dressing 404 may have a pressure that may also be referred to as a manifold pressure. In some embodiments, the tube 410 and the tube 412 may each have at least one lumen. The at least one lumen in the tube 410 and the tube 412 may collectively be referred to as a supply lumen. In other embodiments, the container 403 may be omitted, and the tube 410 may be coupled directly to the dressing 404. In these embodiments, the at least one lumen in the tube 410 may be considered a supply lumen. The dressing 404 may also be fluidly coupled to the control port 321. For example, a tube 408 may fluidly couple the dressing 404 to the control port 321. In some embodiments, the tube 408 may have at least one lumen. The at least one lumen of the tube 408 may also be referred to as a feedback lumen.

The dressing 404 may be fluidly coupled to the supply port 318 and the control port 321 so that fluid communication may occur between the supply chamber 310 and the dressing 404 through the container 403, and between the dressing 404 and the control chamber 312. Fluid communication between the dressing 404, the supply chamber 310 and the control chamber 312 may equalize the pressures in the supply chamber 310, the dressing 404, and the control chamber 312. For example, fluid communication between the dressing 404, the supply chamber 310, and the control chamber 312 may equalize the supply pressure in the supply chamber 310, the manifold pressure in the dressing 404, and the control pressure in the control chamber 312. If the source port 314 is not coupled to the reduced-pressure source 402, the charging port 316 may remain open and the ambient pressure may equalize between the charging chamber 308, the supply chamber 310, the dressing 404, and the control chamber 312.

In some embodiments, the monitor port 323 and the monitor port 319 may be fluidly coupled. For example, a tube, such as a tube 415 may fluidly couple the monitor port 319 to the monitor port 323. In some embodiments, the tube 415 may provide a fluid path between the monitor port 323 and the monitor port 319. In other embodiments, the tube 415 may provide fluid communication between the monitor port 323 and the monitor port 319. In still other embodiments, the tube 415 may provide both fluid communication and a fluid path between the monitor port 323 and the monitor port 319.

The reduced-pressure source 402 may be coupled to the source port 314, providing a reduced pressure to the charging chamber 308. If the regulator valve 326 is in the open position, the charging port 316 provides a fluid path between the charging chamber 308 and the supply chamber 310. As the supply of reduced pressure reduces the pressure within the charging chamber 308, the pressure in the supply chamber 310 may similarly drop. The pressure in the supply chamber 310 may also be referred to as a supply pressure. Fluid communication through the supply port 318 will similarly lower the pressure in the dressing 404, and fluid communication through the control port 321 may similarly begin to lower the pressure in the control chamber 312. As the control pressure in the control chamber 312 drops, the differential force, acting in opposition to the force of the regulator spring 334 will increase, eventually overcoming the force of the regulator spring 334, causing the stem 328 to move downward and forcing the regulator valve 326 into the closed position in which the valve member 322 is seated in the charging port 316. In the closed position, the valve member 322 may block fluid communication through the charging port 316. Decreases in reduced pressure at the dressing 404 may decrease the differential force, so that the biasing force of the regulator spring 334 overcomes the differential force to open the regulator valve 326. In the open position, fluid communication through the charging port 316 may resume until the pressure at the dressing 404, and in turn the control chamber 312, drops sufficiently to overcome the regulator spring 334, again closing the regulator valve 326. Repeated opening and closing of the regulator valve 326 may occur while reduced-pressure therapy is provided.

In some embodiments, the central passage 317 may be calibrated to provide a leak indicator in the system 400. For example, a known diameter of the central passage 317 may be correlated to a rate at which reduced pressure falls if there is a leak in the system 400. By controlling the diameter of the central passage 317, a pressure indicator coupled to the system 400 may be calibrated to trigger at a reduced pressure associated with the rate at which reduced pressure falls if there is a leak. In some embodiments, the known diameter of the central passage 317 may be about 0.45 mm. In some embodiments, the central passage 317 may control the rate at which reduced pressure falls if there is a leak in the system coupled to the regulator 300. In some embodiments, the height of the charging port 316 may also be used.

Figure 4C:
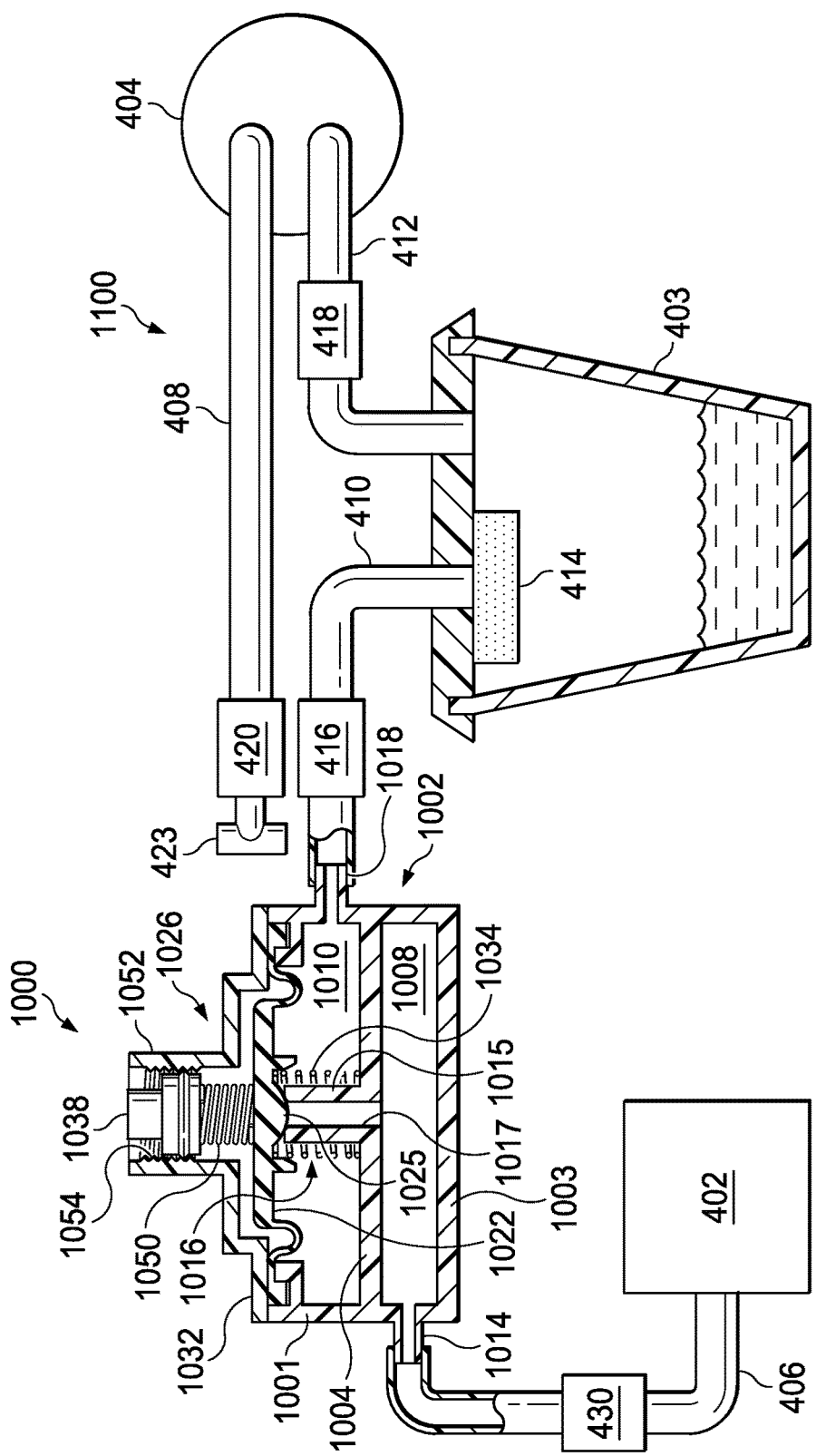
FIG. 4C is a schematic cross-section of an example embodiment of a reduced-pressure therapy system using the regulator of FIG. 3D.

FIG. 4C is a schematic illustration of a reduced-pressure system 1100 illustrating additional details that may be associated with the operation of some embodiments of the regulator 1000. The reduced-pressure system 1100 is an example embodiment of the reduced-pressure therapy system 100 and may be similar to or analogous to the reduced-pressure system 400 in many respects. For example, the reduced-pressure system 1100 may include the reduced-pressure source 402, the container 403, and the dressing 404. The tube 406 may fluidly couple the reduced-pressure source 402 to the source port 1014, as shown in the illustrative embodiment of FIG. 4C. The container 403 may be fluidly coupled to the supply port 1018. In some embodiments, the tube 410 may fluidly couple the container 403 to the supply port 1018. The tube 412 may fluidly couple the dressing 404 to the container 403. In some embodiments, the dressing 404 may include a fluid connection that permits a pressure at the dressing 404 to be measured. For example, the tube 408 may be fluidly coupled to the dressing 404. In some embodiments, the tube 408 may have a cap 423 on an opposite end of the tube 408 from the dressing 404. The cap 423 may prevent fluid communication through the end of the tube 408.

The dressing 404 may be fluidly coupled to the supply port 1018 so that fluid communication may occur between the supply chamber 1010 and the dressing 404 through the container 403. Fluid communication between the dressing 404 and the supply chamber 1010 may equalize the pressures in the supply chamber 1010 and the dressing 404. If the source port 1014 is not coupled to the reduced-pressure source 402, the charging port 1016 may remain open and the ambient pressure may equalize between the charging chamber 1008, the supply chamber 1010, and the dressing 404.

The reduced-pressure source 402 may be coupled to the source port 1014, providing a reduced pressure to the charging chamber 1008. If the regulator valve 1026 is in the open position, the charging port 1016 provides a fluid path between the charging chamber 1008 and the supply chamber 1010. As the supply of reduced pressure reduces the pressure within the charging chamber 1008, the pressure in the supply chamber 1010 may similarly drop. Fluid communication through the supply port 1018 will similarly lower the pressure in the dressing 404. As the supply pressure in the supply chamber 1010 drops, the differential force, acting in concert with the force of the calibration spring 1050 and in opposition to the force of the regulator spring 1034 can increase. The differential force can overcome the force of the regulator spring 1034, causing the valve member 1022 to move downward and into the closed position. In the closed position, the valve member 1022 may be seated in the charging port 1016. In the closed position, the valve member 1022 may block fluid communication through the charging port 1016. Decreases in reduced pressure at the dressing 404 may decrease the differential force, so that the biasing force of the regulator spring 1034 overcomes the differential force and the calibration force of the calibration spring 1050 to open the regulator valve 1026. In the open position, fluid communication through the charging port 1016 may resume until the pressure at the dressing 404 drops sufficiently to overcome the regulator spring 1034, again closing the regulator valve 1026. Repeated opening and closing of the regulator valve 1026 may occur while reduced-pressure therapy is provided.

Feedback Interfaces

The reduced-pressure system 400 or the reduced-pressure system 1100 may also provide feedback to an operator. For example, the reduced-pressure system 400 or the reduced-pressure system 1100 may include one or more feedback interfaces to signal that reduced pressure is being applied within a prescribed range. A feedback interface may also indicate other conditions, such as an over-pressure condition, a leak condition, or a blockage condition. In some embodiments, the feedback may include audible feedback, visual feedback, tactile feedback, or any combination thereof. A feedback interface may include an indicator, gauge, or signal, for example.

A feedback interface may be coupled to or otherwise disposed in the reduced-pressure system 400 or the reduced-pressure system 1100, or combinations of feedback interfaces may be distributed in various locations throughout the reduced-pressure system 400 or the reduced-pressure system 1100. In some embodiments, a feedback interface may be coupled inline to a tube or other fluid path in the reduced-pressure system 400 or the reduced-pressure system 1100. For example, the reduced-pressure system 400 or the reduced-pressure system 1100 may include a feedback interface coupled to a tube 410 at a location 416, which is between the supply port 318 or the supply port 1018 and the container 403. Additionally or alternatively, a feedback interface may be coupled to a tube 412 at a location 418 between the container 403 and the dressing 404. A feedback interface may also be coupled to a tube 408 at a location 420 between the dressing 404 and the control port 321. In the embodiment of FIG. 4C, the location 420 may correspond with a fluid coupling to the dressing 404 independent of the regulator 1000. In some embodiments, a feedback interface may be coupled to the reduced-pressure system 400 at a location 430 between the reduced-pressure source 402 and the source port 314 or between the reduced-pressure source 402 and the source port 1014.

A feedback interface may also be coupled to more than one fluid path in some embodiments. For example, a feedback interface at location 416 may be fluidly coupled to a tee-fitting that may in turn be fluidly coupled to at least two of the supply port 318, the tube 410, and the container 403. In still other embodiments, the tube 410 may be spliced so that a feedback interface at location 416 may be fluidly coupled to the tube 410. Similarly, a feedback interface at location 418 may be fluidly coupled inline between the dressing 404 and the container 403. A feedback interface at location 420 may be fluidly coupled inline between the dressing 404 and the control port 321 of the regulator 300, and the feedback interface at location 430 may be fluidly coupled inline between the reduced-pressure source 402 and the source port 314 of the regulator 300 or the source port 1014 of the regulator 1000.

In some embodiments, the reduced-pressure system 400 may further include a feedback interface at location 424, location 426, location 428, or various combinations thereof. A feedback interface may be positioned at location 426, for example, between the monitor port 319 and the monitor port 323. A feedback interface may also be positioned at location 424 between the monitor port 323 and a feedback interface at location 426. A feedback interface may be positioned at location 428 between a feedback interface at location 426 and the monitor port 319. A feedback interface at location 426 may be fluidly coupled to feedback interfaces at location 424 and location 428 in a manner similar to that described above with respect to a feedback interface at location 416.

A flow indicator is an example embodiment of a feedback interface that can be used in the illustrative embodiments of the reduced-pressure system 400 or the reduced-pressure system 1100. For example, a flow indicator may be deployed at location 416, location 418, location 420, location 424, location 426, location 428, or location 430. In some embodiments, a flow indicator is a mechanical flow indicator that can provide audible, visual, or tactile feedback of fluid movement. FIG. 4B is a schematic sectional view of an example embodiment of an audible flow indicator 417. In the illustrated embodiment, the audible flow indicator 417 is a tee-fitting having a first fluid passage 419 extending through the tee-fitting and a second fluid passage 421 intersecting the first fluid passage 419. Fluid flow through the first fluid passage 419 may induce a fluid flow through the second fluid passage 421. The second fluid passage 421 may be sized so that if the fluid flow through the first fluid passage 419 exceeds a predetermined flow rate, the induced fluid flow through the second fluid passage 421 may produce an audible tone. In some embodiments, the first fluid passage 419 and the second fluid passage 421 are sized so that the audible tone is produced if a leak in the reduced-pressure system 400 or the reduced-pressure system 1100 causes airflow through the audible flow indicator 417 to exceed a threshold flow rate. The audible flow indicator 417 can be calibrated so that the threshold flow rate corresponds to leaks that interfere or prevent therapeutic application of reduced-pressure. For example, a leak at the dressing 404 may cause the regulator 300 to provide an increased flow of reduced pressure. If the flow indicator at location 420 is an audible flow indicator 417, the increased flow through the location 420 can induce an audible tone, such as a whistle, alerting an operator of a leak condition that may require remedial action.

A pressure gauge is another example embodiment of a feedback interface that may be used in the illustrative embodiment of the reduced-pressure system 400 or the reduced-pressure system 1100. For example, a mechanical pressure gauge may be disposed at location 416, location 418, location 420, location 424, location 426, location 428, or location 430. In general, a pressure gauge is a device configured to determine and display a pressure in fluid communication with the pressure gauge. Thus, a mechanical pressure gauge can provide visual feedback for the operating state of the reduced-pressure system 400 or the reduced-pressure system 1100.

In some embodiments, the regulator 300 may also be a feedback interface. For example, a leak condition generally causes the regulator valve 326 to reciprocate between an open and closed position as it attempts to compensate for the leak. The frequency of the reciprocation is generally proportional to the severity of the leak condition. At higher frequencies, the reciprocation can provide tactile feedback. The actuator 330 can also provide audible feedback at higher frequencies. Thus, the regulator 300 can provide a proportional leak alarm.

Figure 5A:
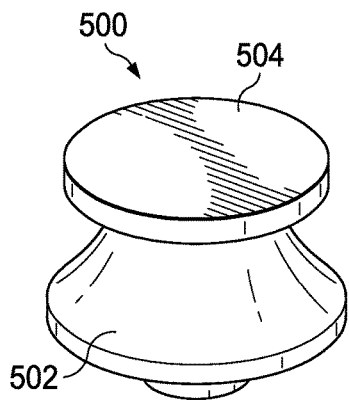
FIG. 5A is a perspective view of a feedback interface that may be used with some embodiments of the reduced-pressure therapy system of FIG. 4A or FIG. 4C.

FIG. 5A is a perspective view of an example embodiment of a pressure indicator 500. The pressure indicator 500 is another example embodiment of a feedback interface that can be used to provide visual feedback of pressure in the illustrative embodiment of the reduced-pressure system 400 or the reduced-pressure system 1100. In some embodiments, the pressure indicator 500 may be disposed at of any one or more of location 416, location 418, location 420, or location 424. As illustrated in FIG. 5A, some embodiments of the pressure indicator 500 may be formed with a side wall 502 and a head 504. The side wall 502 may be a collapsible wall that has a first end coupled to the head 504 and a second end opposite the head 504. The head 504 may round, as illustrated in FIG. 5A, or may have other shapes, such as square, triangular, or amorphous shapes, for example.

Figure 5B:
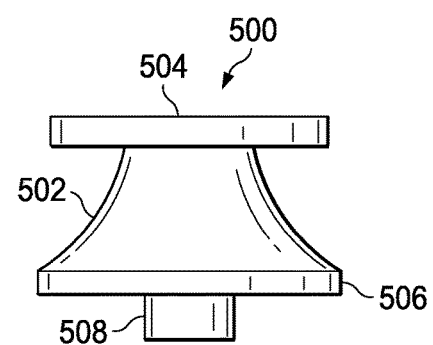
FIG. 5B is a side view of the feedback interface of FIG. 5A.

FIG. 5B is a side view of the pressure indicator 500, illustrating additional details that may be associated with some embodiments. For example, the pressure indicator 500 may have an end wall 506 coupled to the side wall 502 opposite the head 504. If the end wall 506 is coupled to the side wall 502 opposite the head 504, the end wall 506, the head 504 and the side wall 502 may collectively form the pressure indicator 500. The pressure indicator 500 may also include a port 508 in some embodiments. The port 508 may be disposed in the end wall 506 near a center of the end wall 506. The port 508 may be configured to fluidly couple the pressure indicator 500 to other devices, such as the tube 410, the tube 412, or the monitor port 323, for example.

Figure 5C:
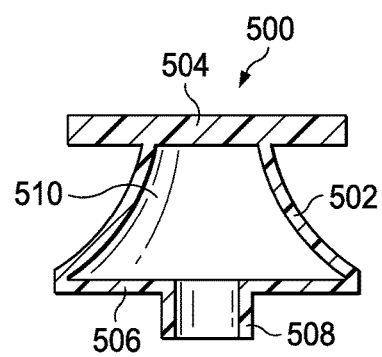
FIG. 5C is a sectional view of the feedback interface of FIG. 5A.

FIG. 5C is a sectional view of the pressure indicator 500, illustrating additional details that may be associated with some embodiments. As illustrated, the head 504, the side wall 502, and the end wall 506 may be coupled to form a chamber 510 within the pressure indicator 500. In some embodiments, the port 508 may provide a fluid path to the chamber 510. The side wall 502 may have a convex interior surface and may include baffles or other features.

The pressure indicator 500, including the side wall 502, the head 504 and the end wall 506, may be formed from a medical-grade, soft polymer or other pliable material. As non-limiting examples, the pressure indicator 500 may be formed from polyurethane, polyethylene, polyvinyl chloride (PVC), fluorosilicone, ethylene-propylene, etc. In some embodiments, the pressure indicator 500 may be molded from bis(2-ethylhexyl) phthalate (DEHP)-free PVC. The pressure indicator 500 may be molded, casted, or extruded, and may be formed as an integral unit.

Figure 5D:
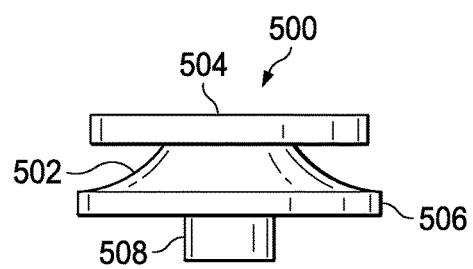
FIG. 5D is a side view of the feedback interface of FIG. 5A in a first position.

FIG. 5D is a side view of the pressure indicator 500, illustrating additional details that may be associated with some embodiments. In operation, reduced pressure through the port 508 may collapse the side wall 502 if the reduced pressure in the chamber 510 exceeds a threshold pressure. The thickness, stiffness, and geometry of the side wall 502 are variables that may impact the threshold pressure at which the side wall 502 collapses. While the wall thickness of the side wall 502 may be determined using finite element analysis, it may be necessary to empirically determine the wall thickness to achieve movement at the threshold pressure.

In some embodiments, the side wall 502 may be designed so that the side wall 502 collapses as pressure in the chamber 510 falls below the threshold pressure. If the side wall 502 collapses, the head 504 may move from a first position, also referred to as an extended position, as shown in FIG. 5B, to a second position, also referred to as a retracted position, as shown in FIG. 5D. The side wall 502 of the pressure indicator 500 may be sized and shaped to collapse or move the head 504 to be adjacent the end wall 506 if the threshold pressure is achieved. If pressure in the chamber 510 stays or rises above the threshold pressure, the side wall 502 may return to the extended position of FIG. 5B. For example, the pressure indicator 500 can be calibrated so that the threshold pressure is less than or equal to a therapy pressure. Thus, the pressure indicator 500 can provide binary, visual feedback for the state of therapeutic pressure in a reduced-pressure system such as reduced-pressure system 400 or the reduced-pressure system 1100.

In some embodiments, the pressure indicator 500 may be coupled to the tube 410 at location 416, between the supply port 318 and the container 403. For example, the pressure indicator 500 at location 416 may indicate by proxy that the therapy pressure has been reached at the supply chamber 310 and the container 403. Similarly, the pressure indicator 500 may be disposed at location 418 to indicate that the therapy pressure has been reached at the supply chamber 310, the container 403, and the dressing 404. If the pressure indicator 500 is disposed at location 420, collapse of the pressure indicator 500 may indicate that the therapy pressure has been reached at the supply chamber 310, the container 403, the dressing 404, and the control chamber 312. If the pressure indicator 500 is disposed at location 428, collapse of the pressure indicator 500 may indicate that the therapy pressure has been reached at the supply chamber 310.

Pressure indicators may also be used to indicate a blockage condition. For example, a first pressure indicator 500 may be fluidly coupled to location 416 and a second pressure indicator 500 may be coupled to location 418. A blockage condition in the container 403, the tube 410, or the tube 412 can be indicated if the first pressure indicator 500 is collapsed but the second pressure indicator 500 is extended. Pressure indicators can be used to indicate leaks, as well. For example, a first pressure indicator 500 may be fluidly coupled to location 418 and a second pressure indicator 500 may be coupled to location 420. A leak condition, such as a leak in the dressing 404, can be indicated if the first pressure indicator 500 is collapsed but the second pressure indicator 500 is extended.

Figure 6A:
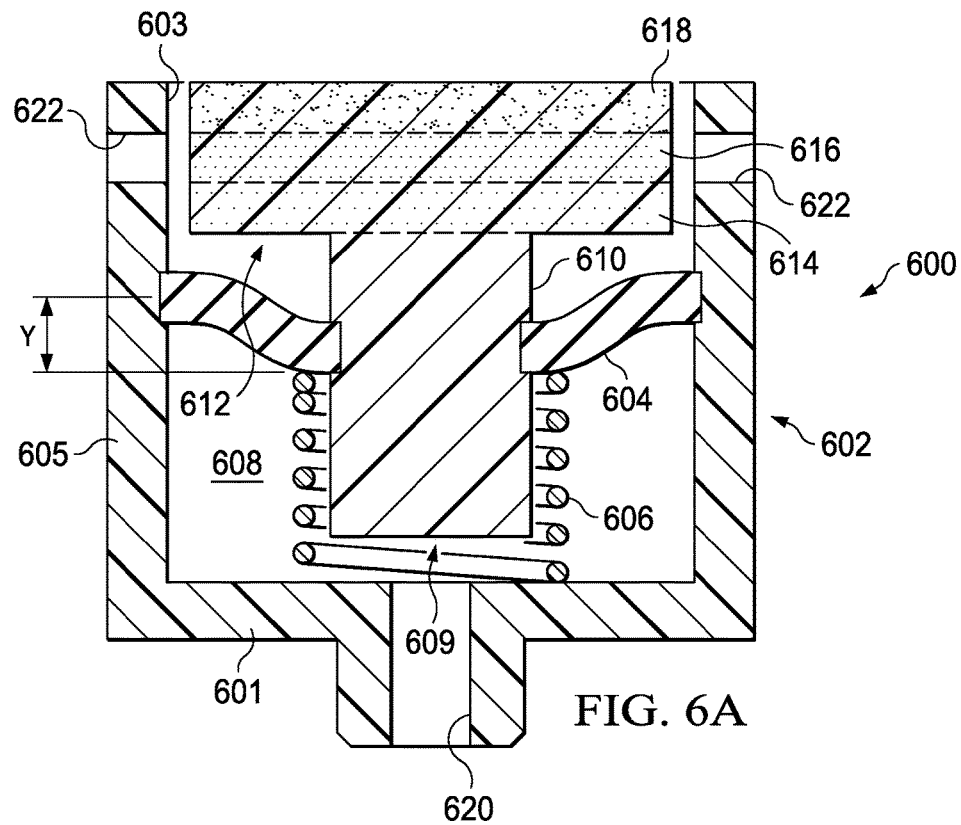
FIG. 6A is a schematic sectional view of a feedback interface that may be used with some embodiments of the reduced-pressure therapy system of FIG. 4A or FIG. 4C.
Figure 6B:
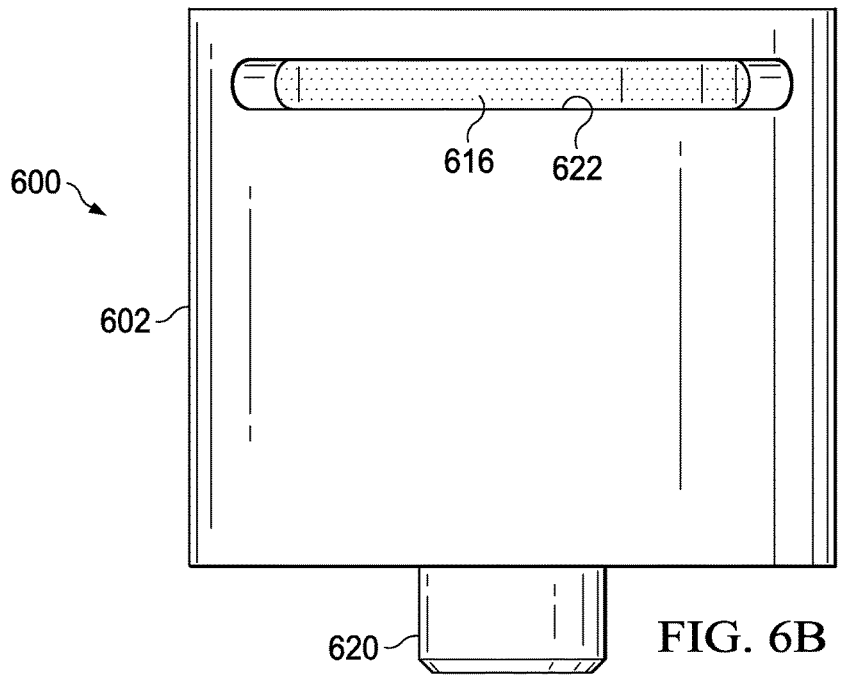
FIG. 6B is a side view of the feedback interface of FIG. 6A.

FIG. 6A is a schematic sectional view of a pressure indicator 600 that may be used with some embodiments of the reduced-pressure system 400 or the reduced-pressure system 1100. FIG. 6B is a schematic side view of the pressure indicator 600, illustrating additional details that may be associated with some embodiments. The pressure indicator 600 is another example embodiment of a feedback interface that can be used to provide visual feedback of pressure in the illustrative embodiment of the reduced-pressure system 400 or the reduced-pressure system 1100. In some embodiments, the pressure indicator 600 may be disposed at of any one or more of location 416, location 420, location 424, location 428, or location 430. As illustrated in FIG. 6A and FIG. 6B, the pressure indicator 600 may have a housing 602. The housing 602 may be tubular and have an end wall 601. Peripheral portions of the end wall 601 may be coupled to an end of a side wall 605. The housing 602 may have an open end 603 opposite the end wall 601. The housing 602 may further have a chamber 608, a port 620 formed in the end wall 601 of the housing 602, and a window 622 formed in the side wall 605 proximate to the open end 603 of the housing 602. In some embodiments shown in FIG. 6A, the chamber 608 is generally defined by and formed within the end wall 601 and the side wall 605. The port 620 may be configured to fluidly couple the pressure indicator 600 to other devices, such as the tube 410 or the monitor port 319, for example. In some embodiments, the port 620 may provide a fluid path to the chamber 608.

The pressure indicator 600 may also have a diaphragm 604 disposed within the chamber 608. The diaphragm 604 may have peripheral portions sealingly engaged to the housing 602. For example, peripheral portions of the diaphragm 604 may be anchored to the side wall 605. In some embodiments, a center portion of the diaphragm 604 may be configured to move relative to the peripheral portions of the diaphragm 604. The movement may be parallel to the side wall 605, for example. The diaphragm 604 may substantially prevent fluid transfer across the diaphragm 604 to fluidly seal at least a portion of the chamber 608. The diaphragm 604 may be formed of a material having an elasticity to allow for elastic deformation of the diaphragm 604. In some embodiments, the diaphragm 604 may be formed of a silicone, for example. In some embodiments, the diaphragm 604 may have a hardness between about 30 Shore A and about 50 Shore A.

The pressure indicator 600 may also include a plunger 609 disposed within the housing 602. Some embodiments of the plunger 609 may include a stem 610 and a cap 612, for example. The stem 610 may be cylindrical in some embodiments. The stem 610 may pass through an aperture in the diaphragm 604. In some embodiments, the stem 610 may be coupled to the diaphragm 604. In some embodiments, for example, the stem 610 may be coupled to a center portion of the diaphragm 604 and may be fluidly sealed to the diaphragm 604. In some embodiments, movement of the center portion of the diaphragm 604 may also cause the stem 610 to move in a same direction.

The cap 612 may be coupled to an end of the stem 610. The cap 612 may be cylindrical in some embodiments, and may have a major dimension greater than a corresponding dimension of the stem 610. In other embodiments, the major dimension of the cap 612 may be the same as the dimension of the stem 610. The plunger 609 may also have indicator rings in some embodiments. For example, the cap 612 may include a first ring 614, a second ring 616, and a third ring 618, as illustrated in FIG. 6A. In some embodiments, the first ring 614 may be positioned adjacent to an end of the stem 610, the second ring 616 may be positioned adjacent to the first ring 614, and the third ring 618 may be positioned adjacent to the second ring 616. In some embodiments, the first ring 614, the second ring 616, and the third ring 618 are stacked parallel to the side wall 605. In some embodiments, the first ring 614, the second ring 616, and the third ring 618 may be integral to the stem 610 or coaxial with the stem 610. In some embodiments, the first ring 614, the second ring 616, and the third ring 618 may be marked with different colors. For example, the first ring 614 may be red, the second ring 616 may be green, and the third ring 618 may be black. In some embodiments, the cap 612 may be disposed within the housing 602 so that at least a portion of the cap 612 is visible through the window 622. Preferably, at least one of the first ring 614, the second ring 616, or the third ring 618 is also visible through the window 622.

The pressure indicator 600 may also have a biasing member, such as a spring 606, disposed in the chamber 608. In some embodiments, the spring 606 may be disposed in the chamber 608 between the end wall 601 of the housing 602 and the diaphragm 604. In some embodiments, the spring 606 may have a first end engaged or otherwise coupled to the diaphragm 604 and a second end engaged or otherwise coupled to the end wall 601 adjacent to the port 620. The spring 606 may be positioned so that the spring 606 can be compressed against the end wall 601 of the housing 602 by the diaphragm 604. In some embodiments, a portion of the stem 610 between the diaphragm 604 and the end wall 601 of the housing 602 may be at least partially circumscribed by the spring 606.

In operation, the port 620 may be fluidly coupled to a source of reduced pressure, exposing the port 620 and the chamber 608 to a reduced pressure. Pressure in the chamber 608 may decrease in response to the application of the reduced pressure until the pressure in the chamber 608 is in equilibrium with the reduced pressure fluidly coupled to the port 620. The pressure in the chamber 608 may exert a force on a first side of the diaphragm 604 facing the chamber 608. Similarly, an ambient pressure may exert a force on an opposite side of the diaphragm 604 through the open end 603 of the housing 602. The sum total of the forces acting on the diaphragm 604 due to the differential pressures on opposite sides of the diaphragm 604 may be referred to as a differential force. Generally, if a reduced pressure is supplied to the chamber 608, the differential force urges the diaphragm 604 toward the port 620. The differential force may be countered by a spring force exerted on the diaphragm 604 by the spring 606. The spring force may be proportional to a spring constant of the spring 606 and a distance the spring 606 may be compressed by the diaphragm 604.

Thus, changes in pressure within the chamber 608 may actuate the diaphragm 604, which in turn, can cause the plunger 609 to slide or otherwise move within the housing 602. As the plunger 609 moves within the housing 602, portions of the plunger 609 that are visible within the window 622 may change to indicate various operating states of a reduced-pressure system. For example, the spring force of the spring 606 may be selected so that a prescribed pressure urges the diaphragm 604 toward the end wall 601, compressing the spring 606 a first distance Y. The movement of the diaphragm 604 toward the end wall 601 may also move the stem 610 and the cap 612 toward the end wall 601. In some embodiments, the second ring 616 and the window 622 may be sized so that the second ring 616 is aligned with the window 622 if the spring 606 is compressed the distance Y, as shown in FIG. 6a and FIG. 6B, to indicate that the prescribed pressure is being applied.

Figure 7A:
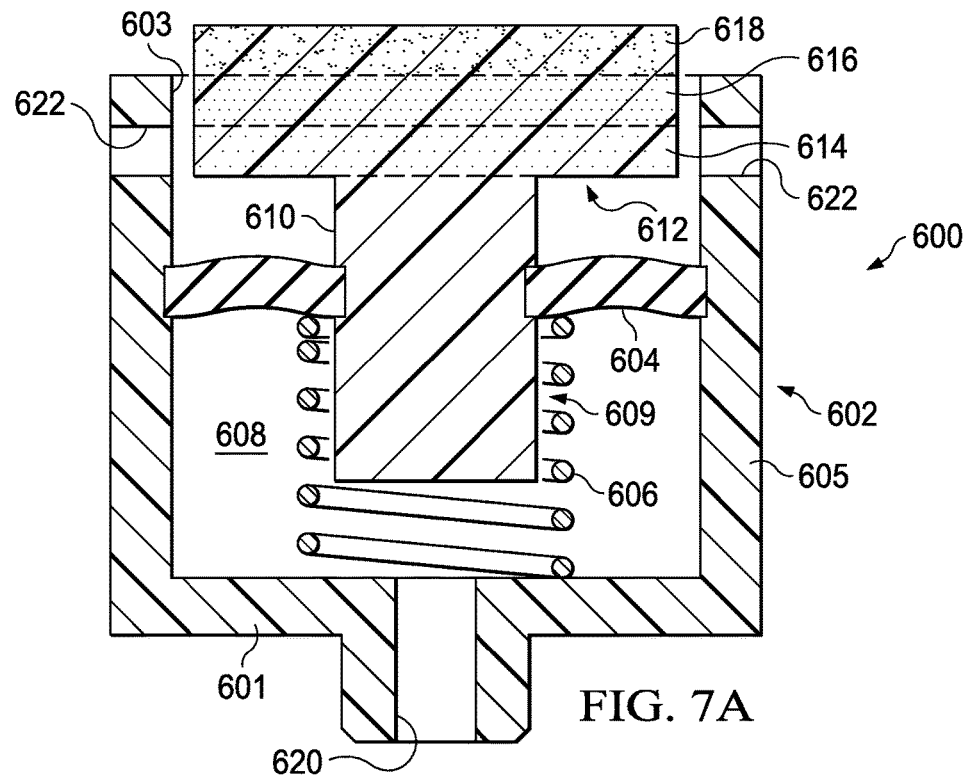
FIG. 7A is a schematic sectional view illustrating additional details that may be associated with one example state of the feedback interface of FIG. 6A.
Figure 7B:
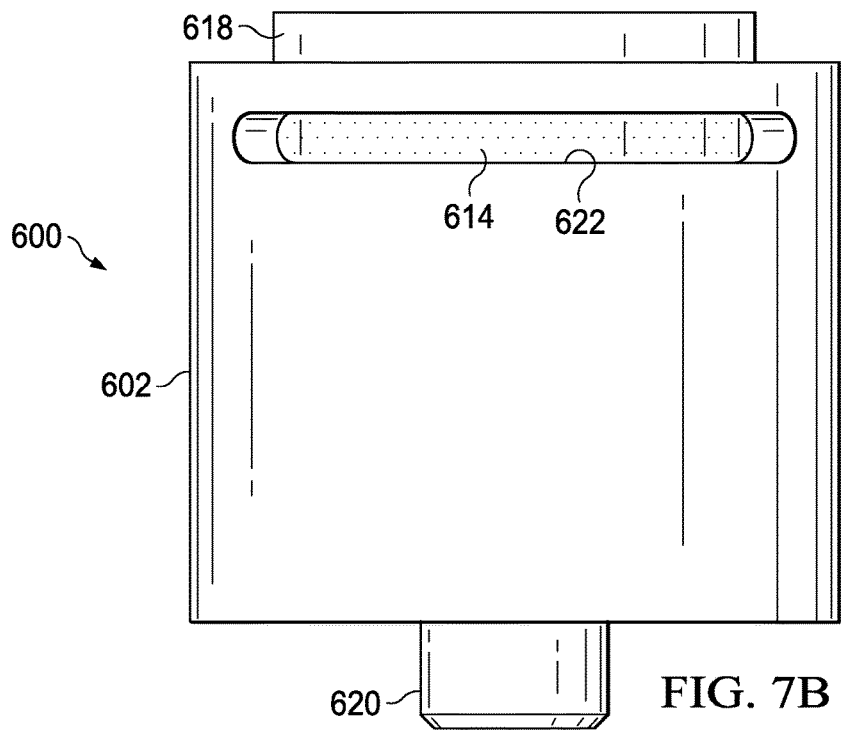
FIG. 7B is a side view of the feedback interface of FIG. 7A.

FIG. 7A is a schematic sectional view illustrating additional details that may be associated with some embodiments of the pressure indicator 600. FIG. 7B is a schematic side view of the pressure indicator 600 in FIG. 7A. If the port 620 is exposed to a reduced pressure that is less than the therapy pressure, the differential force acting on the diaphragm 604 may be less than the spring force acting on the diaphragm 604, allowing the spring 606 to be at an equilibrium position and uncompressed. The plunger 609 may be configured so that the first ring 614 is visible through the window 622 if the spring 606 is in the equilibrium position, as shown in FIG. 7B. In some embodiments, for example, the first ring 614 may be red to signal an under-pressure or a leak condition if visible through the window 622.

Figure 8A:
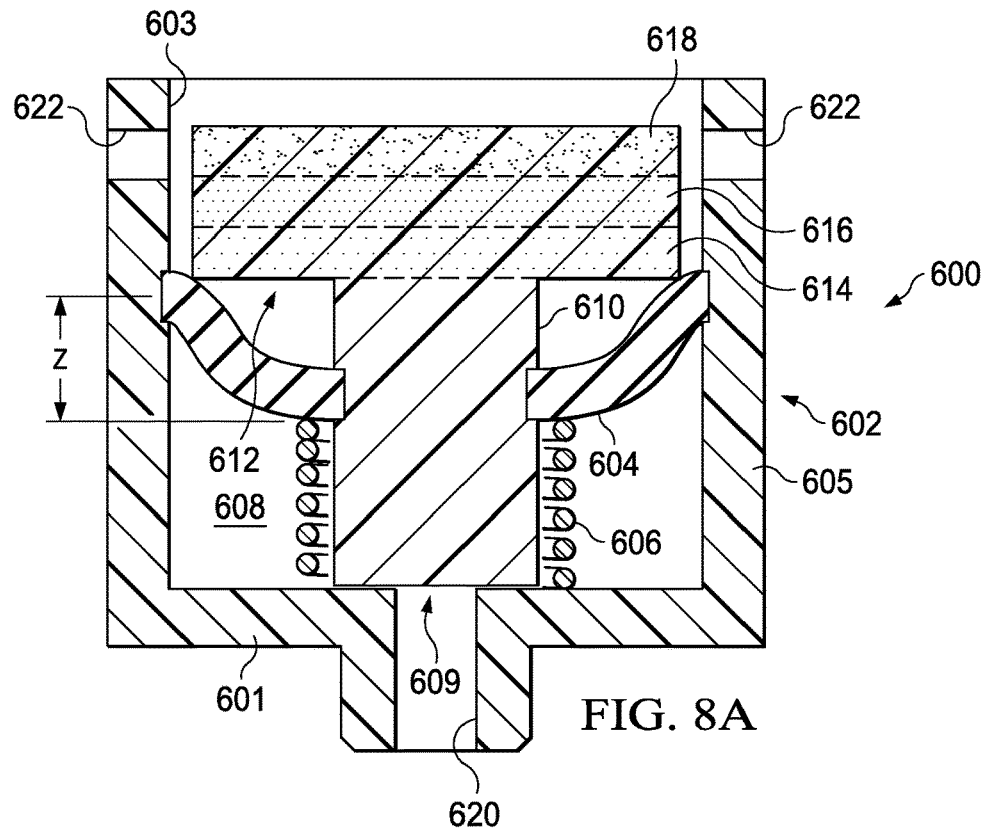
FIG. 8A is a schematic sectional view illustrating additional details that may be associated with another example state of the feedback interface of FIG. 6A.
Figure 8B:
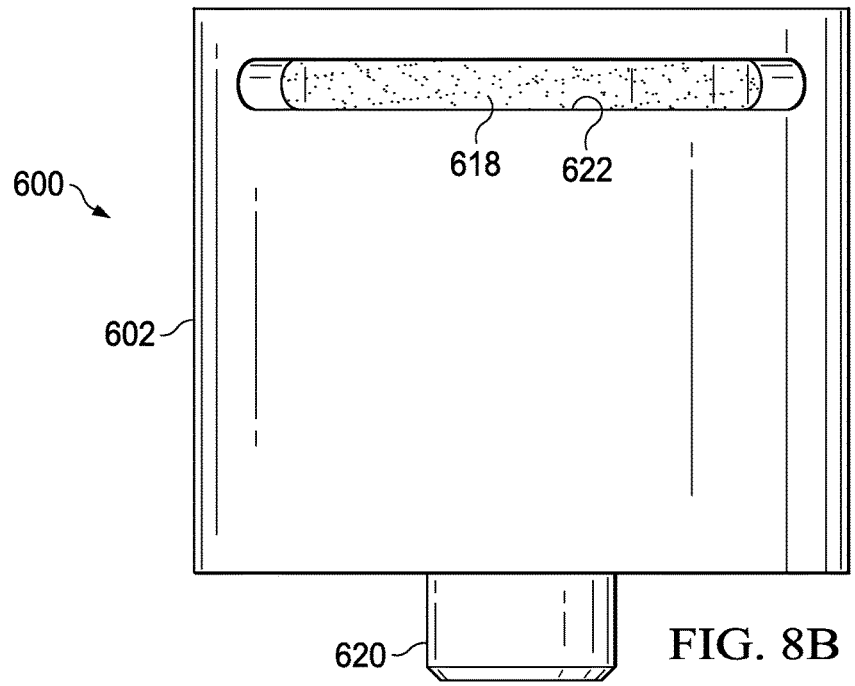
FIG. 8B is a side view of the feedback interface of FIG. 8A.

FIG. 8A is a schematic sectional view illustrating additional details that may be associated with some embodiments of the pressure indicator 600. FIG. 8B is a schematic side view of the pressure indicator 600 of FIG. 8A. If the port 620 is exposed to a reduced pressure that exceeds the therapy pressure, the differential force acting on the diaphragm 604 may urge the diaphragm 604 toward the end wall 601, compressing the spring 606 a second distance Z.

The second distance Z may be greater than the first distance Y. The movement of the diaphragm 604 may also move the stem 610 and the cap 612 toward the end wall 601. The plunger 609 may be configured so that the third ring 618 is visible through the window 622 if the spring is compressed the second distance Z, as shown in FIG. 8B. In some embodiments, for example, the third ring 618 may be black to signal an overpressure condition.

The size of the window 622 and the dimensions of the first ring 614, the second ring 616, and the third ring 618 may also be configured so that only the second ring 616 is visible within the window 622 if the reduced pressure is within an acceptable range or tolerance of the prescribed therapy pressure. In some embodiments, for example, the window 622 may be thinner than the second ring 616 so that the plunger 609 may move within the housing 602 some distance before the first ring 614 or the third ring 618 is also visible within the window 622. For example, a therapy pressure of −120 mm Hg may be prescribed, but pressure 10 mm Hg above or below the therapy pressure may be beneficial or otherwise acceptable under given treatment conditions. Thus, in some embodiments, the window 622 may be sized so that only the second ring 616 is visible if pressure in the chamber 608 is within the therapeutic range of −130 mm Hg to −110 mm Hg.

The pressure indicator 600 may be used in some embodiment of the reduced-pressure system 400 or the reduced-pressure system 1100 to provide a signal regarding the operating state of the reduced-pressure system 400 or the reduced-pressure system 1100. For example, if the pressure indicator 600 is disposed in location 416, the pressure indicator 600 may signal the operating state of the reduced-pressure system 400 between the supply chamber 310 and the container 403. Some embodiments of the reduced-pressure system 400 or the reduced-pressure system 1100 may have more than one pressure indicator 600 to signal different operating states of the reduced-pressure system 400 or the reduced-pressure system 1100. For example, in some embodiments, a first pressure indicator 600 may be disposed at location 416 and a second pressure indicator 600 may be disposed at location 418. If the first pressure indicator 600 signals an overpressure condition and the second pressure indicator 600 signals a leak condition, the container 403 may be full or there may be a blockage condition between location 416 and location 418.

Figure 9A:
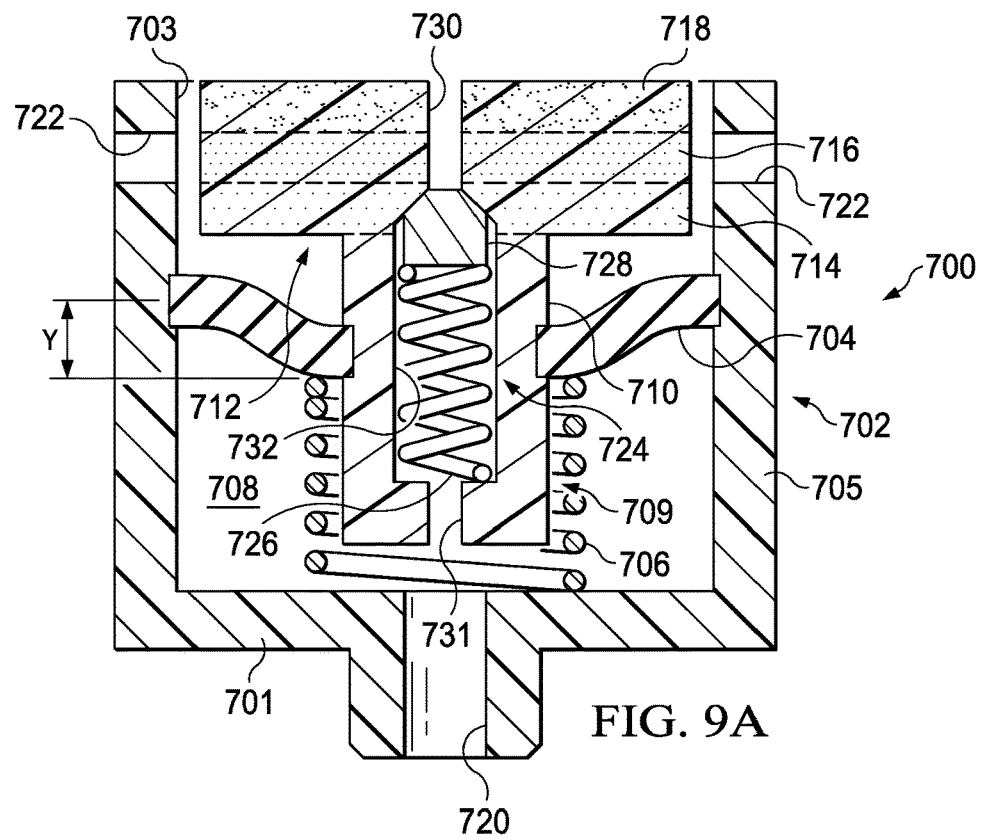
FIG. 9A is a schematic sectional view of another feedback interface that may be used with some embodiments of the reduced-pressure therapy system of FIG. 4A or FIG. 4C.
Figure 9B:
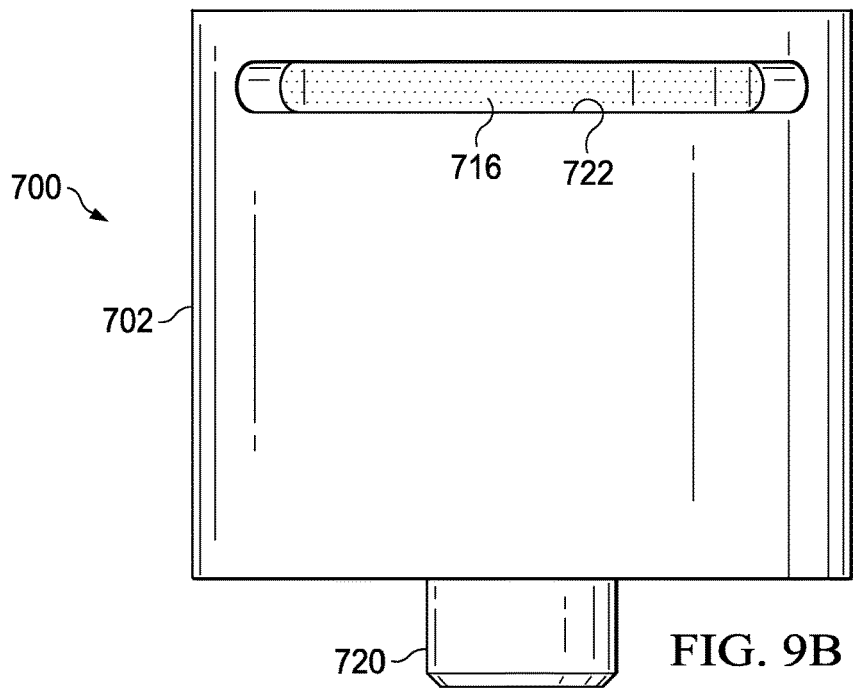
FIG. 9B is a side view of the feedback interface of FIG. 9A.

FIG. 9A is a schematic sectional view of a pressure indicator 700 that may be used with some embodiments of the reduced-pressure system 400 or the reduced-pressure system 1100. FIG. 9B is a schematic side view of the pressure indicator 700. The pressure indicator 700 is another example embodiment of a feedback interface that can be used to provide visual feedback of pressure in the illustrative embodiment of the reduced-pressure system 400 or the reduced-pressure system 1100. In some embodiments, the pressure indicator 700 may be disposed in any one or more of location 416, location 420, location 424, location 428, and location 430. In some embodiments, the pressure indicator 700 may have a housing 702 and a valve 724, as shown in FIG. 9A. The pressure indicator 700 may be similar to and operate in the manner described above with respect to the pressure indicator 600 of FIGS. 6A-8B.

In some embodiments, the valve 724 may be an overpressure valve disposed within a plunger 709. The plunger 709 may include a stem 710 and a cap 712, and the stem 710 may include a cavity 732. The cavity 732 may be cylindrical and extend a length of the stem 710. In some embodiments, the cavity 732 may be in fluid communication with the chamber 708 through a passage 731. The passage 731 may be formed in an end of the stem 710 that is opposite the cap 712. The cavity 732 may also be in fluid communication with the ambient atmosphere through a passage 730. The passage 730 may extend from the cavity 732 through the cap 712. The valve 724 may further include a valve spring 726 and a valve member 728. The valve spring 726 may be positioned in the cavity 732. In some embodiments, the valve spring 726 may have a first end positioned adjacent to the passage 731. The valve spring 726 may have a second end proximate to the cap 712. The valve spring 726 may be configured to be compressed against the end of the cavity 732. The valve member 728 may be disposed within the cavity 732 and positioned between an end of the valve spring 726 and the cap 712. In some embodiments, the valve member 728 may be sized to block the passage 730 if the valve member 728 is positioned adjacent to the passage 730. In some embodiments, the valve member 728 may be sized to permit fluid communication around the valve member 728 if the valve member 728 is separated from the passage 730.

Figure 10A:
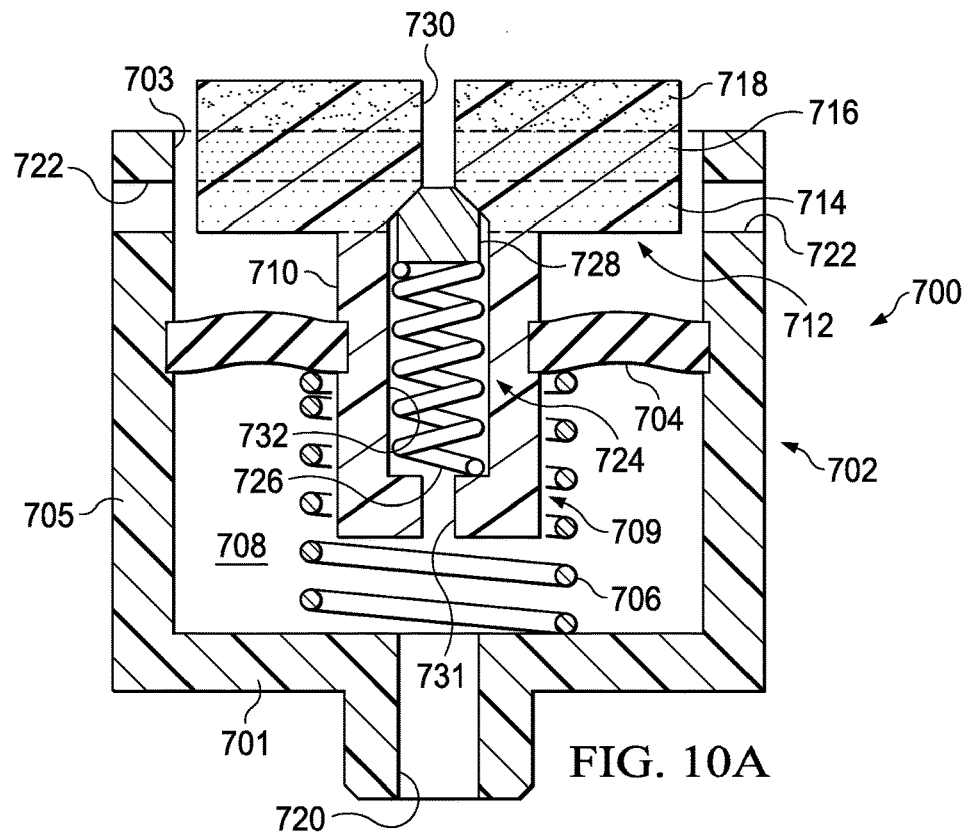
FIG. 10A is a schematic sectional view illustrating additional details that may be associated with one example state of the feedback interface of FIG. 9A.
Figure 10B:
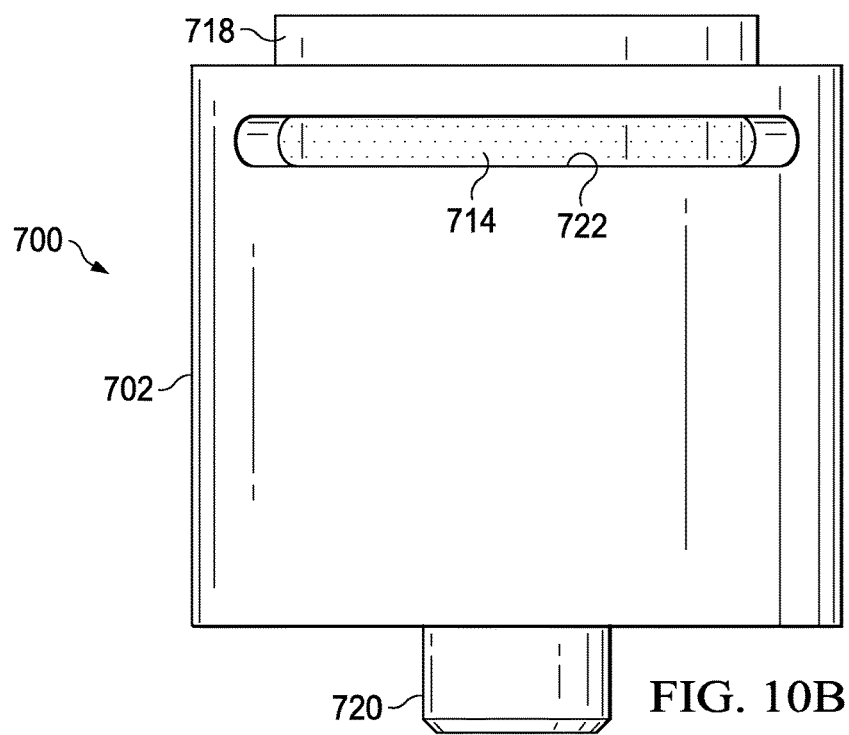
FIG. 10B is a side view of the feedback interface of FIG. 10A.

Generally, the pressure indicator 700 may operate as described above with respect to the pressure indicator 600 of FIGS. 6A-8B to indicate one or more operating states of a reduced-pressure system. For example, the pressure indicator 700 may indicate application of a prescribed therapy pressure, as shown in FIG. 9A and FIG. 9B; a leak condition, as shown in FIG. 10A and FIG. 10B; a blockage condition, a canister full condition, or an overpressure condition, as shown in FIG. 11A and FIG. 11B.

In addition, the pressure indicator 700 may provide pressure relief through the valve 724. The pressure in the chamber 708 may exert a force on a side of the valve member 728 facing the cavity 732. An ambient pressure may exert a force on a side of the valve member 728 through the passage 730. The valve spring 726 may also exert a spring force on the valve member 728. The spring force may be proportional to a spring constant of the valve spring 726 and a distance the valve spring 726 is compressed from an equilibrium position. Thus, changes in pressure within the chamber 708 can cause the valve member 728 to slide or otherwise move within the cavity 732. For example, the spring force of the valve spring 726 may be selected so that a reduced pressure less than or equal to the therapy pressure urges the valve spring 726 toward the passage 730 so that the valve 724 is in a closed position, as shown in FIG. 9A and FIG. 10A. The spring force of the valve spring 726 may also be selected so that a reduced pressure that exceeds the therapy pressure urges the valve member 728 away from the passage 730 so that the valve 724 is in an open position, as shown in FIG. 11A.

Figure 11A:
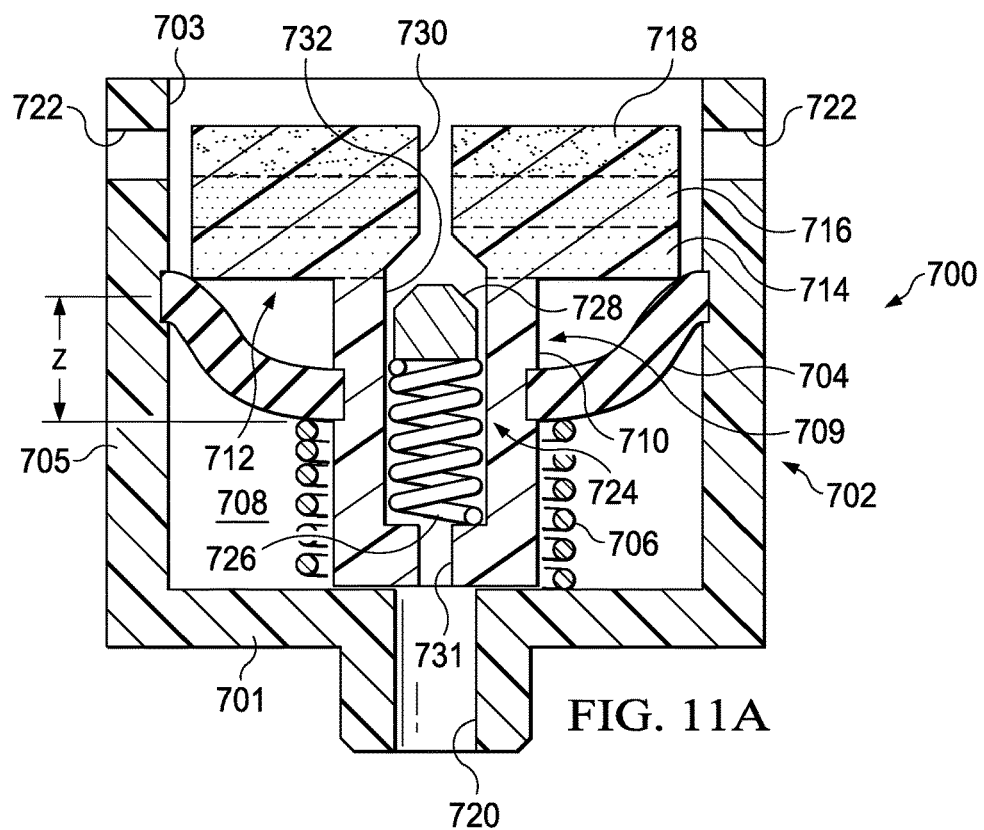
FIG. 11A is a schematic sectional view illustrating additional details that may be associated with another example state of the feedback interface of FIG. 9A.
Figure 11B:
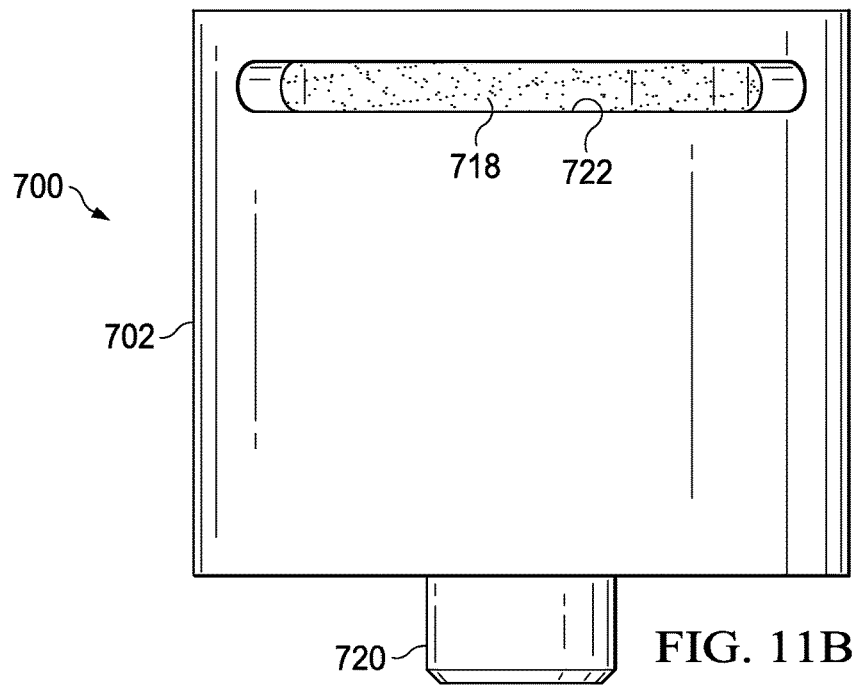
FIG. 11B is a side view of the feedback interface of FIG. 11A.

If the valve 724 is in an open position, as in FIG. 11A, fluid communication may occur between the ambient environment and the chamber 708. For example, fluid may flow through the passage 730 around the valve member 728 and into the cavity 732. Fluid may flow from the cavity 732 through the passage 731 into the chamber 708. Fluid may also flow from the chamber 708 through the port 720. In this manner, an overpressure condition may be relieved by an inflow of ambient pressure into the chamber 708. In some embodiments, the pressure indicator 700 may include a filter disposed over the passage 730. The filter may be a bacteria filter, a dust filter, or a moisture filter, for example. In some embodiments, pressure indicator 700 may also provide audible feedback for an overpressure condition, since fluid flowing through the passage 730 may produce a whistle or other audible vibration.

Figure 12A:
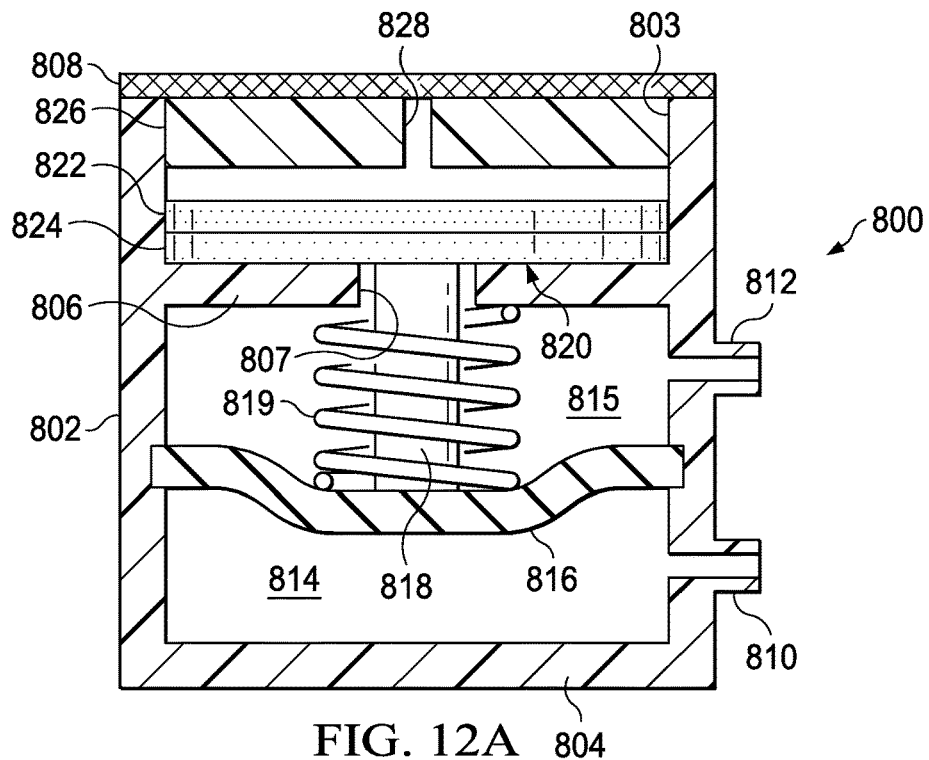
FIG. 12A is a schematic sectional view of another feedback interface that may be used with some embodiments of the reduced-pressure therapy system of FIG. 4A or FIG. 4C.

FIG. 12A is a schematic sectional view of a pressure indicator 800, which can be used with some embodiments of the reduced-pressure system 400 of FIG. 4A or the reduced-pressure system 1100 of FIG. 4C. The pressure indicator 800 is another example embodiment of a feedback interface that can be used to provide visual feedback of pressure in the illustrative embodiment of the reduced-pressure system 400 or the reduced-pressure system 1100. In some embodiments, for example, the pressure indicator 800 may be disposed at location 426 of the reduced-pressure system 400 to provide visual feedback for a blockage condition. The pressure indicator 800 may include a housing 802 having an end wall 804 and an open end 803. The open end 803 may be opposite the end wall 804. In some embodiments, the housing 802 may be cylindrical. In other embodiments, the housing 802 may be other shapes, such as cuboid or pyramidal, for example. A partition 806 having an opening 807 may be disposed in the housing 802. In some embodiments, the partition 806 may be positioned between the end wall 804 and the open end 803. The partition 806 may have peripheral portions coupled to the housing 802. In some embodiments, the partition 806 may permit fluid flow in the housing 802 through the opening 807.

The housing 802 may have two adjoining chambers separated by a diaphragm, such as a first chamber 814 and a second chamber 815 separated by a diaphragm 816. The diaphragm 816 may have peripheral portions coupled to the housing 802 and may be substantially impermeable to gas and liquid transmission. In some embodiments, the diaphragm 816 may fluidly separate the first chamber 814 and the second chamber 815. In some embodiments, the diaphragm 816 may be a fluid barrier that prevents fluid flow between the first chamber 814 and the second chamber 815 within the housing 802.

The first chamber 814 may adjoin the end wall 804, and the second chamber 815 may be adjacent to the open end 803. In some embodiments, the partition 806 may be disposed in the second chamber 815. In some embodiments, the partition 806 may be disposed between the diaphragm 816 and the open end 803. A port 810 may be fluidly coupled to the first chamber 814, and a port 812 may be fluidly coupled to the second chamber 815. The port 810 may provide a fluid path to the first chamber 814, and the port 812 may provide a fluid path to the second chamber 815.

The diaphragm 816 may be formed of a material having an elasticity to allow for elastic deformation of the diaphragm 816. In some embodiments, the diaphragm 816 may be formed of a silicone, for example. In some embodiments, the diaphragm 816 may have a hardness between about 30 Shore A and about 50 Shore A.

A stem 818 may be coupled to the diaphragm 816 and extend away from the diaphragm 816 through the second chamber 815. The stem 818 may be cylindrical. In some embodiments, the stem 818 may have a dimension, such as a diameter, for example, that is less than a dimension of the opening 807. An upper end of the stem 818 may pass through the opening 807. In some embodiments, the stem 818 may have a first end coupled to the diaphragm 816 and a second end disposed between the partition 806 and the open end 803.

A cap 820 may be coupled to the second end of the stem 818 that is opposite the diaphragm 816. In some embodiments, the cap 820 may be disposed between the partition 806 and the open end 803. The cap 820 may be cylindrical. In some embodiments, the cap 820 may have a dimension, such as a diameter, for example, that is larger than the opening 807. If the dimension of the cap 820 is larger than the dimension of the opening 807, the cap 820 may not pass through the opening 807. A center portion of the diaphragm 816, the stem 818, and the cap 820 may be rigidly coupled to one another so that movement of one causes movement of the others in a same direction.

The cap 820 may have indicator rings, such as a first ring 822 and a second ring 824. In some embodiments, the first ring 822 and the second ring 824 may be configured as layers in the cap 820, such that the second ring 824 is coupled to the end of the stem 818 and the first ring 822 is coupled to the second ring 824, for example. In other embodiments, the first ring 822 and the second ring 824 may be markings on the surface of the cap 820. In some embodiments, the first ring 822 and the second ring 824 of the cap 820 may have different colors. For example, in some embodiments, the first ring 822 may be green, and the second ring 824 may be red. In other embodiments, the first ring 822 may have another color, such as red, yellow, blue, or black, for example. Similarly, in other embodiments, the second ring 824 may be green, yellow, blue, or black, for example.

The pressure indicator 800 may also have a biasing member, such as a spring 819, for example, disposed in the second chamber 815. The spring 819 may have a first end engaged to the diaphragm 816 and a second end engaged to the partition 806. In some embodiments, the spring 819 may be compressed between the partition 806 and the diaphragm 816. In some embodiments, the stem 818 may be circumscribed by the spring 819.

The pressure indicator 800 may also include a whistle 826 having a passage 828 coupled to the open end 803 of the housing 802. In some embodiments, a lower surface of the whistle 826 may be separated from an upper surface of the partition 806. In these illustrative embodiments, the cap 820 may be configured to move between the partition 806 and the whistle 826. A filter 808 may be coupled to the open end 803 of the housing 802 and cover the passage 828 of the whistle 826. The filter 808 may be a bacteria filter, a dust filter, or a moisture filter, for example.

Figure 12B:
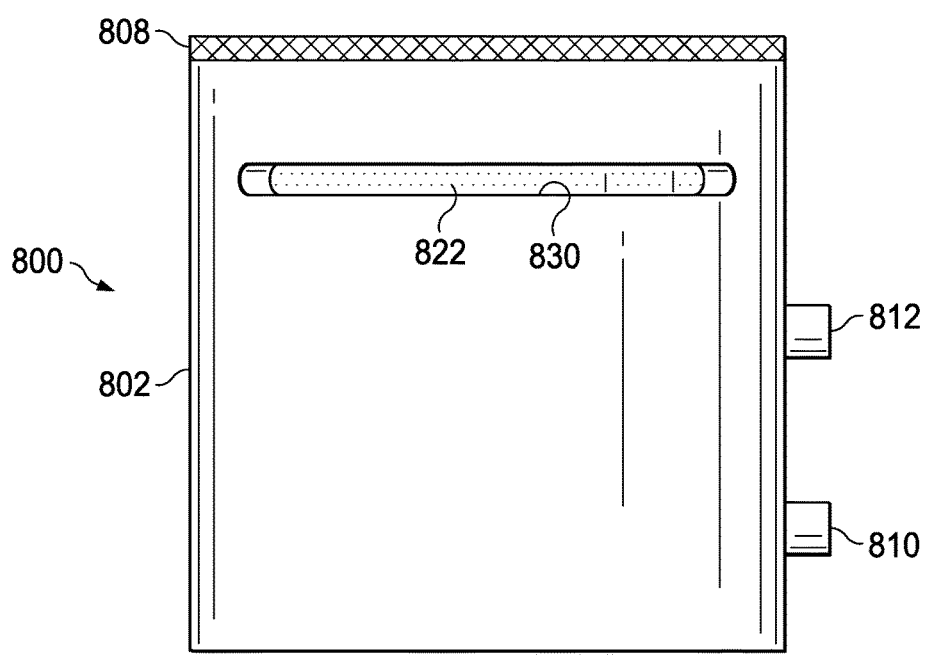
FIG. 12B is a side view of the feedback interface of FIG. 12A.

FIG. 12B is a schematic side view illustrating additional details that may be associated with some embodiments of the pressure indicator 800. For example, the housing 802 may further include a window 830 passing through a side wall of the housing 802 proximate to the open end 803. In some embodiments, at least a portion of the cap 820 may be visible through the window 830. In some embodiments, the first ring 822 of the cap 820 may be visible through the window 830. In other embodiments, the second ring 824 of the cap 820 may be visible through the window 830. In still other embodiments, the first ring 822 and the second ring 824 of the cap 820 may be visible through the window 830. In the illustrative embodiment of FIG. 12B, the first ring 822 of the cap 820 is visible through the window 830.

In operation, the pressure indicator 800 may be fluidly coupled to a reduced-pressure therapy system, such as the reduced-pressure system 400 or the reduced-pressure system 1100. In some embodiments, the port 812 may be coupled to a reduced-pressure source and the port 810 may be fluidly coupled to a tissue site receiving reduced-pressure therapy. For example, the port 812 may be fluidly coupled to the monitor port 319, and the port 810 may be fluidly coupled to the monitor port 323. During normal operation of the reduced-pressure system 400 or the reduced-pressure system 1100, the second chamber 815 may be supplied with the supply pressure, and the first chamber 814 may be supplied with the control pressure. The control pressure in the first chamber 814 and the supply pressure in the second chamber 815 may exert a force on the diaphragm 816. For example, if the supply pressure is greater than the control pressure, then the force may urge the diaphragm 816 toward the end wall 804. If the supply pressure is less than the control pressure, the force may urge the diaphragm 816 toward the partition 806. The spring 819 may exert a counteracting force, also referred to as a spring force, that may be proportional to a spring constant of the spring 819 and a distance the spring 819 is displaced. The combined forces may be referred to as a net force acting on the diaphragm 816.

If the control pressure and the supply pressure are comparable, the pressure differential across the diaphragm 816 may be negligible. The spring 819 may be calibrated to be at an equilibrium position in this state, as shown in FIG. 12A. In some embodiments, the diaphragm 816 may be slightly displaced if the spring 819 is in the equilibrium position, also as shown in FIG. 12A. The cap 820 may have an ambient pressure acting on the cap 820 through the passage 828. The ambient pressure may urge the cap 820 into contact with the partition 806. In some embodiments, the cap 820 may be fluidly sealed to the partition 806 so that no fluid transfer occurs through the opening 807 of the partition 806. Placing the cap 820 into contact with the partition 806 may also position the first ring 822 of the cap 820 adjacent the window 830 so that the first ring 822 may be visible through the window 830. In some embodiments, the first ring 822 is green and may signal that the operating state of the reduced-pressure system 400 or the reduced-pressure system 1100 is an application of reduced pressure within a therapeutic range.

Figure 13A:
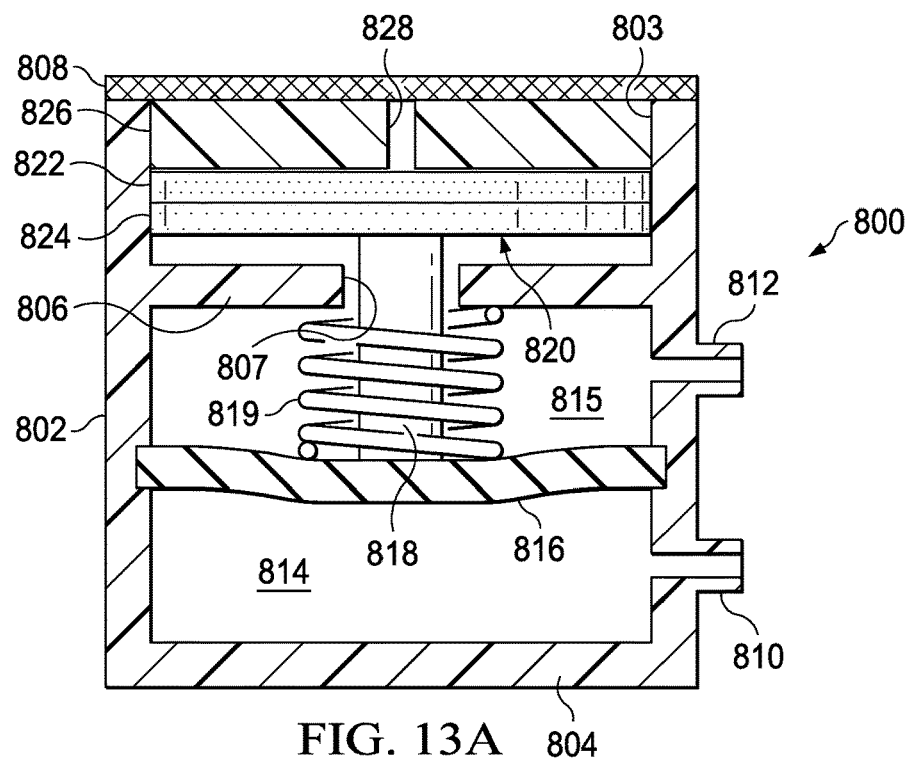
FIG. 13A is a schematic sectional view illustrating additional details that may be associated with an example state of the feedback interface of FIG. 12A.
Figure 13B:
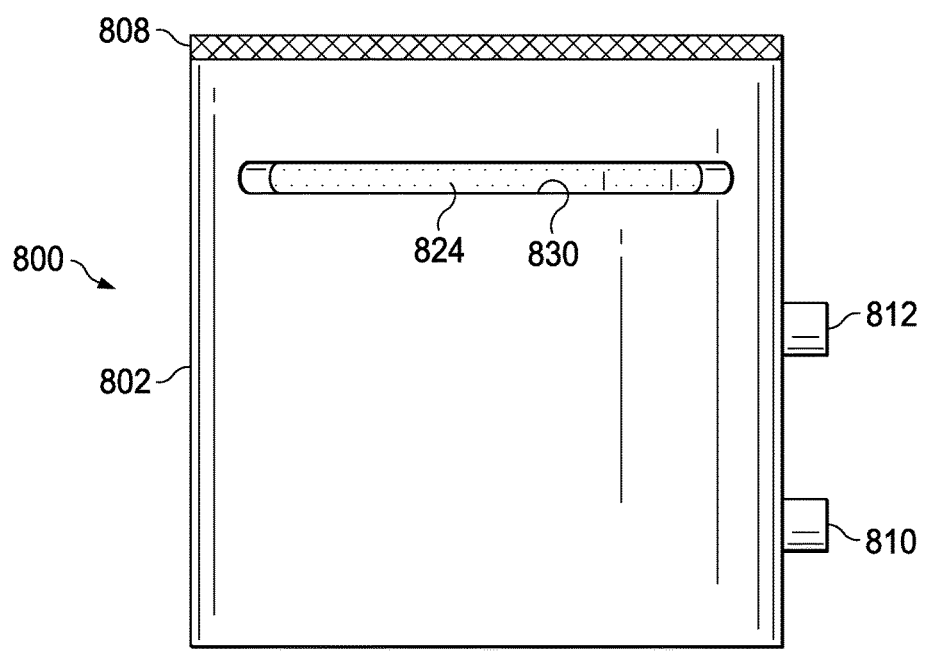
FIG. 13B is a side view of the feedback interface of FIG. 13A.

FIG. 13A is a schematic sectional view illustrating additional details that may be associated with some embodiments of the pressure indicator 800. FIG. 13B is a schematic side view of the pressure indicator 800 of FIG. 13A. In operation, the diaphragm 816 may move toward the partition 806 if the supply pressure in the second chamber 815 is less than the control pressure in the first chamber 814. A difference in the pressure supplied to the second chamber 815 and the first chamber 814 may occur if there is a blockage in the reduced-pressure system 400 or the reduced-pressure system 1100, for example. If there is a blockage between the reduced-pressure source 402 and the dressing 404, the reduced pressure supplied by the reduced-pressure source 402 may not be fluidly communicated to the dressing 404. As a result, the control pressure in the first chamber 814 may be a lower reduced pressure than the reduced pressure in the second chamber 815.

In response to the difference in pressures in the first chamber 814 and the second chamber 815, the diaphragm 816 may move toward the partition 806. In response, the stem 818, coupled to the diaphragm 816 may also move toward the partition 806. The movement of the stem 818 may cause the cap 820 to move away from the partition 806, allowing fluid flow through the opening 807 of the partition 806. In response, ambient air pressure may flow through the filter 808, through the passage 828, around the cap 820 and into the second chamber 815. Fluid may flow through the port 812, which may dislodge the blockage. In some embodiments, the flow of ambient air pressure through the passage 828 may operate the whistle 826, causing the whistle 826 to emit an audible tone. In some embodiments, if the cap 820 moves away from the partition 806, the second ring 824 may be positioned adjacent to the window 830, allowing the second ring 824 to be visible through the window 830. In some embodiments, the second ring 824 may be colored red and may signal to an operator that the operating state is a blockage condition or a canister full condition. Thus, as shown in FIG. 13A and FIG. 13B, the pressure indicator 800 can provide a visual signal for a blockage condition, and may also provide an audible signal.

Movement of the diaphragm 816 toward the partition 806 may compress the spring 819. In response, the spring 819 may generate a counteracting force urging the diaphragm 816 toward the end wall 804. The counteracting force may be proportional to a spring constant of the spring 819 and the distance the spring 819 is compressed. If ambient air pressure flows into the second chamber 815, the pressure in the second chamber 815 may increase. If pressure in the second chamber 815 increases sufficiently, the counteracting force of the spring 819 may overcome the force of the pressure in the first chamber 814 and the second chamber 815 to move the diaphragm 816 toward the end wall 804. In response, the stem 818 and the cap 820 may also move toward the end wall 804. The cap 820 may contact the partition 806, blocking the opening 807 and preventing further fluid flow into the second chamber 815 from the ambient environment.

Figure 14:
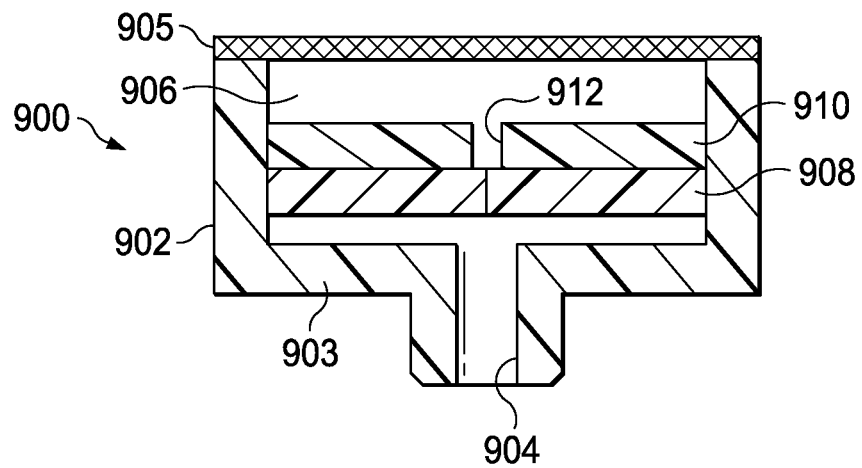
FIG. 14 is a schematic sectional view of another feedback interface that may be used with some embodiments of the reduced-pressure therapy system of FIG. 4A or FIG. 4C.

FIG. 14 is a schematic sectional view of a pressure indicator 900, which may be used with some embodiments of the reduced-pressure system 400 or the reduced-pressure system 1100. The pressure indicator 900 is another example embodiment of a feedback interface that can provide visual feedback of pressure in the illustrative embodiment of the reduced-pressure system 400 or the reduced-pressure system 1100. In some embodiments, for example, the pressure indicator 900 may disposed in one or more of location 416, location 420, or location 424. The pressure indicator 900 may include a housing 902, a valve 908, and a whistle 910. The housing 902 may be cylindrical and have an end wall 903 and a filter 905. The end wall 903 may form a first end of the housing 902, and the filter 905 may form a second end of the housing 902. In some embodiments, the filter 905 may be opposite the end wall 903. The housing 902 may have a chamber 906 disposed between the end wall 903 and the filter 905. The housing 902 may further include a port 904 coupled to the end wall 903. In some embodiments, the port 904 may be configured to be fluidly coupled to additional devices or components of a reduced-pressure system. The port 904 may provide a fluid path into the chamber 906. The filter 905 may provide a fluid path to the ambient environment, permitting the flow of ambient pressure into the chamber 906.

The valve 908 may be disposed in the chamber 906 and have peripheral portions coupled to the housing 902. In some embodiments, the valve 908 may be positioned between the port 904 and the filter 905. In some embodiments, the valve 908 may be separated from the port 904 and the filter 905. In other embodiments, the valve 908 may adjoin the port 904. The valve 908 may be configured to selectively prevent fluid flow between the filter 905 and the port 904. In some embodiments, the valve 908 may permit fluid flow through the valve 908 in response to a predetermined pressure differential across the valve 908. In some embodiments, the predetermined pressure differential across the valve 908 may be referred to as a cracking pressure. In some embodiments, the valve 908 may be a duckbill valve configured to crack at a predetermined pressure to permit fluid communication across the valve 908.

The whistle 910 may be disposed within the chamber 906. In some embodiments, the whistle 910 is positioned between the valve 908 and the filter 905. In some embodiments, the whistle 910 adjoins the valve 908. The whistle 910 may have peripheral portions coupled to the housing 902. In some embodiments, the coupling between the whistle 910 and the housing 902 may prevent fluid flow across the whistle 910. In some embodiments, the whistle 910 may include a passage 912 extending through the whistle 910. The passage 912 may provide a fluid path through the whistle 910. The passage 912 may be configured to emit an audible tone in response to fluid movement through the passage 912.

In operation, the port 904 may be fluidly coupled to a component of a reduced-pressure system, such as to a dressing, container, or reduced-pressure source, for example, so that reduced pressure in the reduced-pressure system may be fluidly communicated to the chamber 906 through the port 904. The reduced pressure may be present in the chamber 906 between the valve 908 and the port 904. Similarly, ambient pressure may be fluidly communicated to the chamber 906 through the filter 905. The ambient pressure may be present in the chamber 906 between the whistle 910 and the filter 905. In some embodiments, if the reduced pressure in the chamber 906 is less than or equal to a prescribed therapy pressure, the valve 908 may remain closed, preventing fluid communication across the valve 908.

Figure 15:
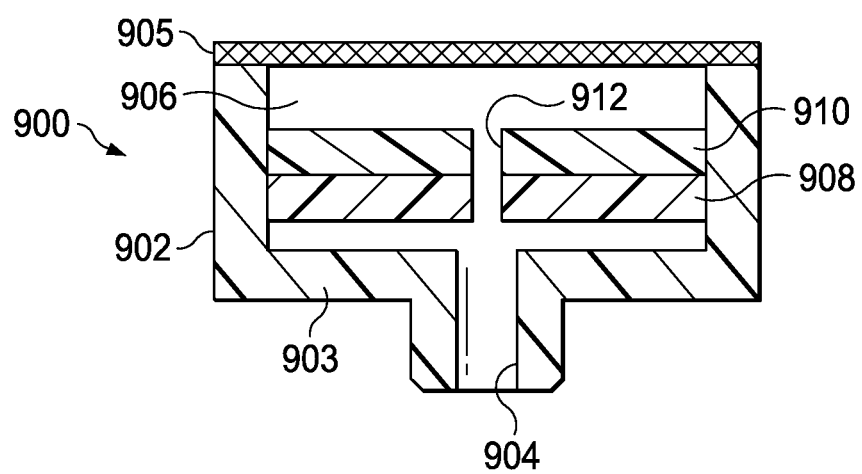
FIG. 15 is a schematic sectional view illustrating additional details that may be associated with an example state of the feedback interface of FIG. 14.

FIG. 15 is a schematic sectional view illustrating additional details that may be associated with some embodiments of the pressure indicator 900. If the reduced pressure in the chamber 906 between the valve 908 and the port 904 exceeds a desired therapy pressure, the valve 908 may open, as shown in FIG. 15. In some embodiments, the valve 908 may be calibrated to open only if the reduced pressure in the chamber 906 exceeds a desired therapy pressure by an acceptable tolerance. For example, the therapy pressure may be about −120 mm Hg gauge pressure, but −130 mm Hg may be acceptable. Thus, the valve 908 may be calibrated to open if the reduced pressure in the chamber 906 between the valve 908 and the port 904 exceeds −130 mm Hg. In some embodiments, if the valve 908 opens, fluid flow may occur through the passage 912 of the whistle 910. If fluid flows through the passage 912 of the whistle 910, an audible tone may be emitted. The audible tone may be interpreted by an operator as a signal of an overpressure condition operating state.

Figure 16:
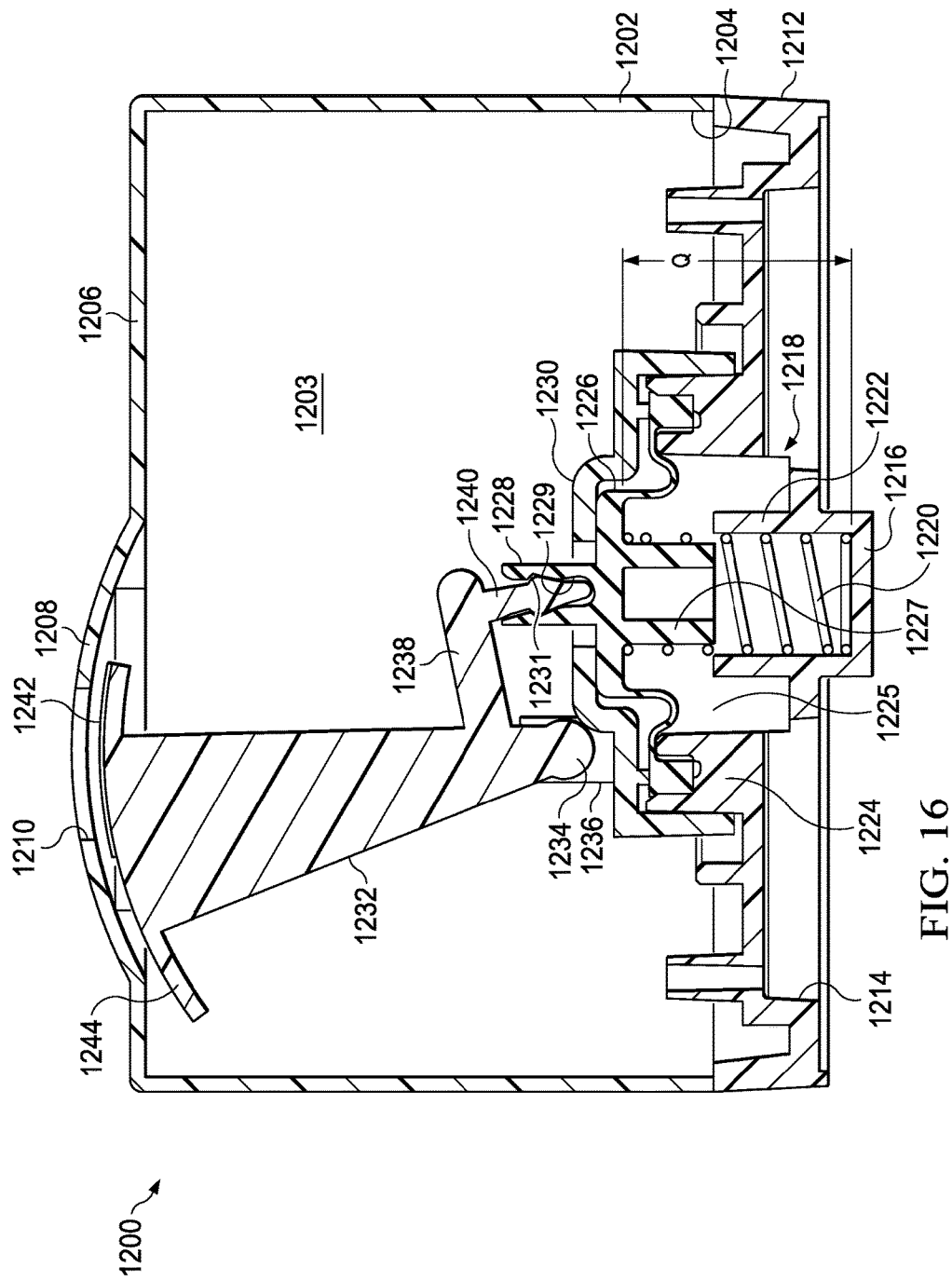
FIG. 16 is a schematic sectional view of another feedback interface that may be used with some embodiments of the reduced-pressure therapy system of FIG. 4A or FIG. 4C.

FIG. 16 is a schematic sectional view, illustrating details of a pressure indicator 1200 that may be used with some embodiments of the reduced-pressure system 400 or the reduced-pressure system 1100. The pressure indicator 1200 is another example embodiment of a feedback interface that can be used to provide visual feedback of pressure in the illustrative embodiment of the reduced-pressure system 400 or the reduced-pressure system 1100. In some embodiments, the pressure indicator 1200 may be disposed at of any one or more of location 416, location 418, location 424, or location 428.

In some embodiments, the pressure indicator 1200 may include a housing formed by a side wall 1202 that is generally tubular. In other embodiments, the housing may not be tubular and the side wall 1202 may include more than one wall coupled to each other to form a side of the pressure indicator 1200. The housing may be open adjacent to a first end of the side wall 1202, and an end wall 1206 may be coupled to a second end of the side wall 1202 that is opposite the first end. In some embodiments, the end wall 1206 may be perpendicular to the side wall 1202 and close the housing of the pressure indicator 1200. The end wall 1206 may have a dome 1208 protruding from the end wall 1206. The dome 1208 may include a window 1210 formed proximate to an apex of the dome 1208.

In some embodiments, the pressure indicator 1200 may also include a base 1212. The base 1212 may be configured to couple to the side wall 1202 to form a chamber 1203 bounded by the side wall 1202, the end wall 1206, and the base 1212. The chamber 1203 may be open to the ambient environment through the window 1210.

In some embodiments, the base 1212 may be countersunk to form a connection chamber 1214. For example, a surface of the base 1212 facing away from the chamber 1203 may have an interior portion countersunk to form the connection chamber 1214. Countersinking the base 1212 may also form a peripheral wall adjacent peripheral portions of the base 1212.

In some embodiments, the base 1212 may include a spring mount. The spring mount may be disposed in the connection chamber 1214 proximate to a center of the base 1212. The spring mount may have a side wall 1222 and an end wall 1216. The side wall 1222 may have a tubular shape extending from the end wall 1216 toward the chamber 1203. In some embodiments, using an outer surface of the base 1212 as a reference, the side wall 1222 may have a portion extending toward the chamber 1203 and a portion extending away from the chamber 1203. In some embodiments, the end wall 1216 may be coupled to an end of the side wall 1222 opposite the chamber 1203 so that the spring mount forms a cavity having an open end proximate to the chamber 1203.

In some embodiments, a spring 1220 may be disposed in the cavity of the spring mount. The spring 1220 may have a first end positioned adjacent to the end wall 1216, and a second end protruding beyond the side wall 1222. The spring 1220 may have a length Q in a relaxed position as shown in FIG. 16. If displaced, the spring 1220 may exert a force proportional to an amount the spring 1220 is displaced from the relaxed position Q.

The base 1212 may also have an annular wall 1224 extending from the connection chamber 1214 toward the chamber 1203. In some embodiments, the annular wall 1224 may extend into the chamber 1203 further than the side wall 1222. In some embodiments, the annular wall 1224 may be positioned radially outward from the side wall 1222 of the spring mount. In some embodiments, at least one communication channel 1218 may be formed between the annular wall 1224 and the side wall 1222. In some embodiments, the communication channel 1218 may be fluidly coupled to the connection chamber 1214.

A diaphragm 1226 may be coupled to the end of the annular wall 1224. In some embodiments, the diaphragm 1226 is disposed in the chamber 1203 proximate to the end of the side wall 1222 of the spring mount. In some embodiments, the diaphragm 1226 and the base 1212 may form a pressure chamber 1225. The pressure chamber 1225 may be disposed between the annular wall 1224 and the diaphragm 1226. In some embodiments, the pressure chamber 1225 may be fluidly isolated from the chamber 1203 and in fluid communication with the communication channel 1218.

In some embodiments, the end of the spring 1220 may be proximate to the diaphragm 1226. In some embodiments, the diaphragm 1226 may have a spring coupler 1227. In some embodiments, the spring coupler 1227 may be disposed proximate to a center of the diaphragm 1226. The spring coupler 1227 may be an annular wall disposed on a side of the diaphragm 1226 adjacent to the spring 1220. In some embodiments, the spring coupler 1227 may have an outer diameter less than an inner diameter of the spring 1220. In some embodiments, the spring coupler 1227 may be inserted into the spring 1220 to operatively couple the spring 1220 to the diaphragm 1226.

In some embodiments, the diaphragm 1226 may include a mechanical coupling 1228. The mechanical coupling 1228 may be located proximate to a center of the diaphragm 1226. In some embodiments, the mechanical coupling 1228 may project from the diaphragm 1226 opposite the spring coupler 1227. The mechanical coupling 1228 may be an annular wall forming a cavity 1229 having a restriction 1231 proximate to an end of the annular wall opposite the diaphragm 1226. In some embodiments, the diaphragm 1231 may be formed from a silicone material. In some embodiments, the diaphragm 1231 may have a hardness rating between about 100 Shore A and about 50 Shore A.

A retainer 1230 may be coupled to the base 1212 adjacent to the diaphragm 1226. In some embodiments, the retainer 1230 may be coupled to ends of the annular wall 1224 and on a side of the diaphragm 1226 opposite the spring mount. The retainer 1230 may have an opening proximate to a center of the retainer 1230. In some embodiments, the mechanical coupling 1228 of the diaphragm 1226 may extend through the opening of the retainer 1230. The retainer 1230 may include a fulcrum 1236 disposed outward from the opening of the retainer 1230. In some embodiments, the fulcrum 1236 may be a post, column, or other body extending into the chamber 1203 from a surface of the retainer 1230.

The pressure indicator 1200 may further include a lever indicator 1232. The lever indicator 1232 may be a lever arm coupled to the fulcrum 1236 and extending through the chamber 1203 from the retainer 1230 to a location proximate to the end wall 1206. In some embodiments, an end of the lever indicator 1232 may be proximate to the dome 1208. The lever indicator 1232 may include a pivot 1234 on an end of the lever indicator 1232 coupled to the fulcrum 1236 of the retainer 1230. In some embodiments, the pivot 1234 may be an axle having a first end coupled to the end of the lever indicator 1232 and a second end coupled to the fulcrum 1236 so that the end of the lever indicator 1232 may be fixed to the fulcrum 1236. In some embodiments, the end of the lever indicator 1232 coupled to the fulcrum 1236 may be referred to as a fixed end, and the opposite end may be referred to as a free end. In some embodiments, the lever indicator 1232 may rotate around the pivot 1234.

In some embodiments, the lever indicator 1232 may also include an arm 1238 protruding from a side of the lever indicator 1232. In some embodiments, the arm 1238 may protrude towards a center of the pressure indicator 1200 so that an end of the arm 1238 may be proximate to the mechanical coupling 1228 of the diaphragm 1226. In some embodiments, the arm 1238 may have a linkage 1240 extending from the arm 1238 to link the arm 1238 with the mechanical coupling 1228. The linkage 1240 may be sized to fit within the cavity 1229 and be retained to the mechanical coupling 1228 by the restriction 1231. The restriction 1231 may be flexible to permit a body having a diameter greater than the restriction 1231 to be inserted through the restriction 1231. In some embodiments, the linkage 1240 may include a detent configured to engage the restriction 1231. The linkage 1240 and the mechanical coupling 1228 operatively couple the diaphragm 1226 and the lever indicator 1232.

The free end of the lever indicator 1232 may have a first indication 1242 and a second indication 1244. In some embodiments, at least one of the first indication 1242 and the second indication 1244 may be visible through the window 1210.

In some embodiments, the connection chamber 1214 may be coupled to a portion of the reduced-pressure system 400 or the reduced-pressure system 1100. A pressure may be supplied to the pressure chamber 1225 through the communication channel 1218 and the connection chamber 1214. The pressure supplied to the pressure chamber 1225 may act on the diaphragm 1226 in combination with an ambient pressure on an opposite side of the diaphragm 1226. If the pressure supplied to the pressure chamber 1225 is less than the ambient pressure, then a differential force move the diaphragm 1226 toward the base 1212. The spring 1220 may have a spring constant such that the differential force overcomes the spring force of the spring 1220 if the pressure in the pressure chamber 1225 is about the therapy pressure. As shown in the illustrated embodiment of FIG. 16, if the reduced pressure in the pressure chamber 1225 is less than the therapy pressure, the differential force may not overcome the spring force of the spring 1220, allowing the spring 1220 to remain in the relaxed position Q, and the first indication 1242 may be visible through the window 1210. In some embodiments, the first indication 1242 may be a color, a phrase, or another visual cue that insufficient reduced pressure is being supplied.

Figure 17:
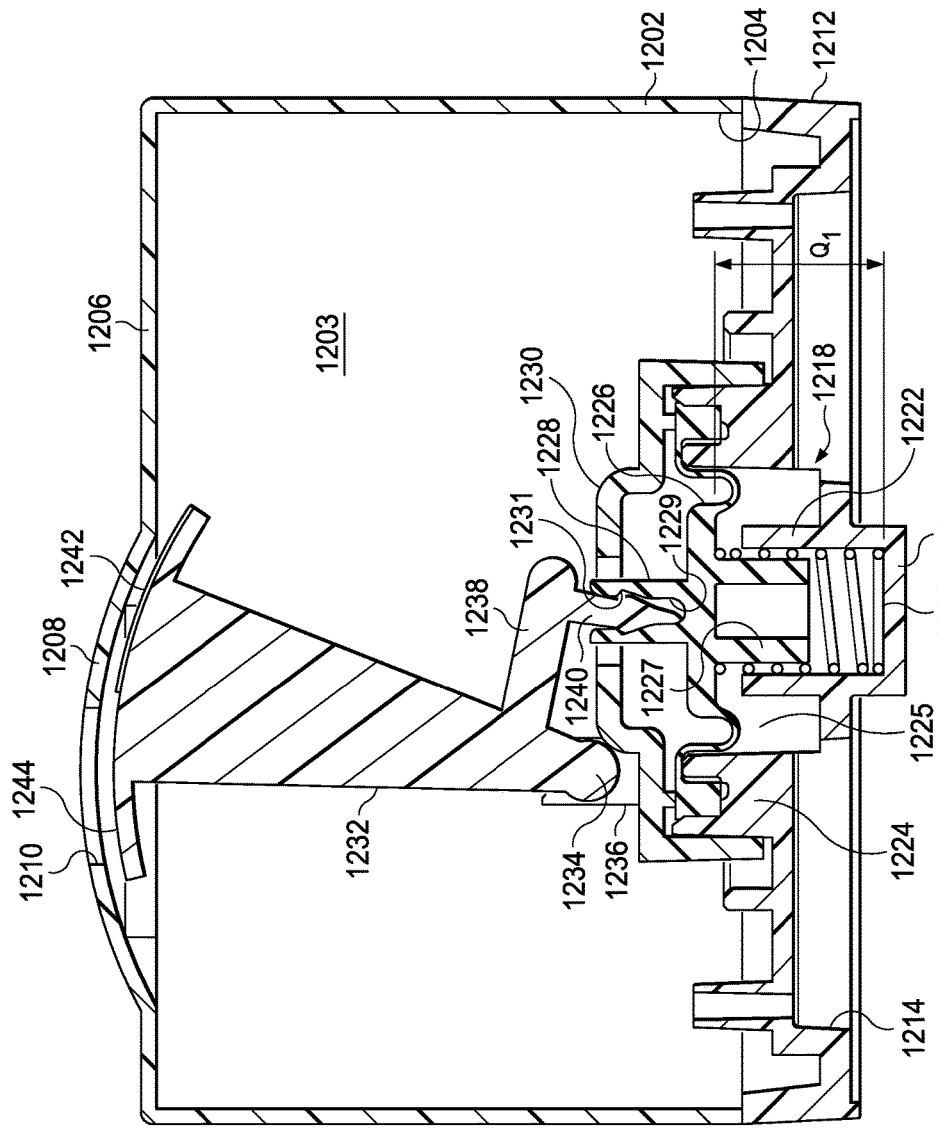
FIG. 17 is a schematic sectional view illustrating additional details that may be associated with an example state of the feedback interface of FIG. 14.

FIG. 17 is a schematic sectional view of the pressure indicator 1200 in a second position. In the second position of FIG. 17, a pressure supplied to the pressure chamber 1225 is about the therapy pressure. In response, the differential force may overcome the spring force of the spring 1220, compressing the spring 1220 to a compressed position $Q_1$, urging the diaphragm 1226 toward the base 1212. In response, the mechanical coupling 1228 may move toward the base 1212. The linkage 1240 may also move toward the base 1212 in response to movement of the mechanical coupling 1228. Movement of the linkage 1240 may pull an end of the arm 1238 toward the base 1212, which may cause the lever indicator 1232 to at least partially rotate about the pivot 1234. Rotation of the lever indicator 1232 about the pivot 1234 may move the second indication 1244 proximate to the window 1210, allowing the second indication 1244 to be visible through the window 1210. In some embodiments, the second indication 1244 may be a color, a phrase, or another visual cue that the therapy pressure is being supplied to the pressure chamber 1225.

Figure 18:
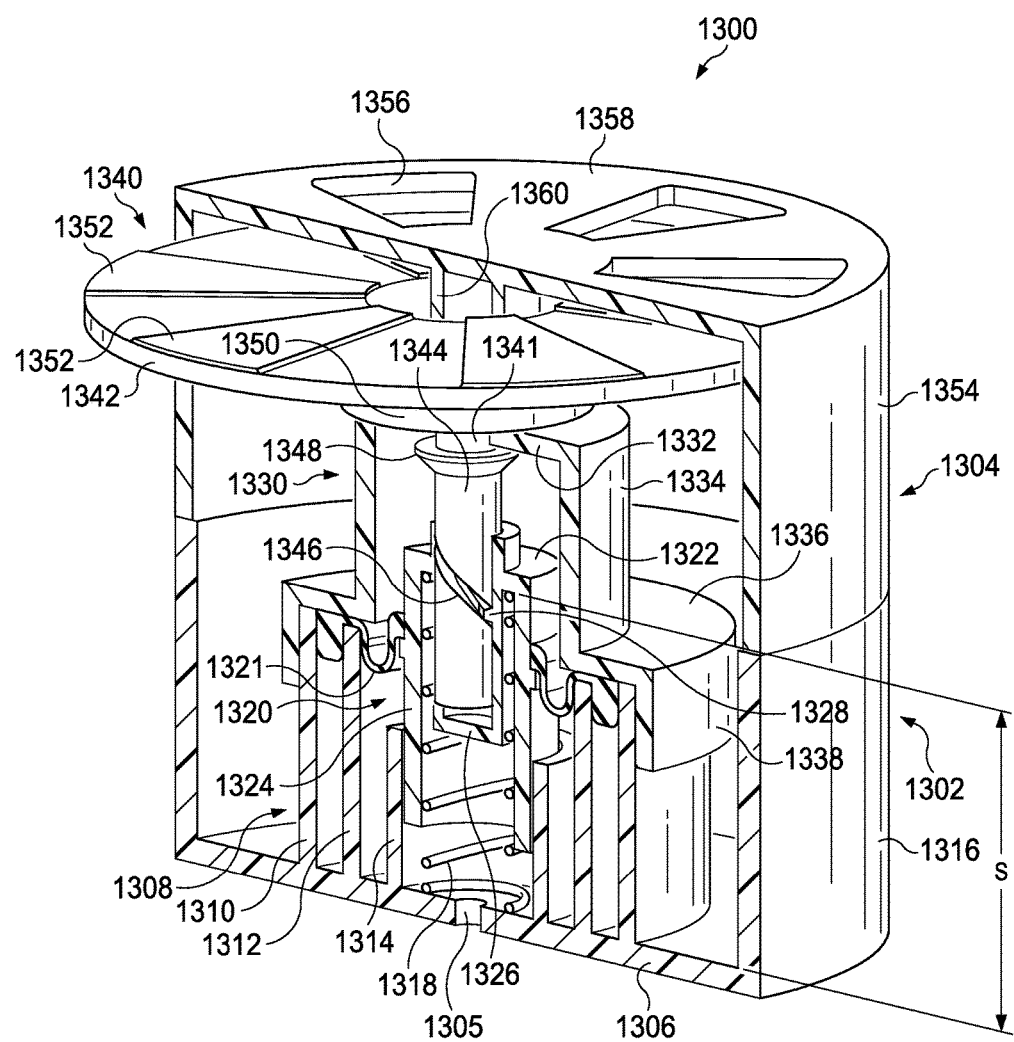
FIG. 18 is a sectional perspective view of another feedback interface that may be used with some embodiments of the reduced-pressure therapy system of FIG. 4A or FIG. 4C.

FIG. 18 is a schematic perspective view, illustrating additional details of a pressure indicator 1300 that may be used with some embodiments of the reduced-pressure system 400 or the reduced-pressure system 1100. The pressure indicator 1300 may be another example embodiment of a feedback interface that can be used to provide visual feedback of pressure in the illustrative embodiment of the reduced-pressure system 400 or the reduced-pressure system 1100. In some embodiments, the pressure indicator 1300 may be disposed at any one or more of location 416, location 418, location 424, or location 428.

In some embodiments, the pressure indicator 1300 may include a cover 1304 and a base 1302. The cover 1304 may include a side wall 1354 and an end wall 1358. In some embodiments, the end wall 1358 may have a circular shape. The end wall 1358 may include one or more windows 1356. The windows 1356 may be openings through the end wall 1358 that permit visual and/or fluid communication through the end wall 1358. In some embodiments, the windows 1356 may be separated circumferentially around the end wall 1358 proximate to a circumferential edge of the end wall 1358. In some embodiments, the spacing may be equidistant between adjacent windows 1356. In some embodiments, the end wall 1358 may include a radial limiter 1360. The radial limiter 1360 may be a projection extending from the end wall 1358. In some embodiments the radial limiter 1360 may have a tubular shape. The side wall 1354 may be a tubular wall and may be coupled to peripheral portions of the end wall 1358. The side wall 1354 may extend from the peripheral portions of the end wall 1358 a same direction as the radial limiter 1360.

The base 1302 may be coupled to the cover 1304 and may include a bottom wall 1306 having a disc shape and a side wall 1316 coupled to the bottom wall 1306. In some embodiments, the bottom wall 1306 may have a circular shape. In some embodiments, the bottom wall 1306 may have an opening 1305. The opening 1305 may be formed proximate to a center of the bottom wall 1306.

In some embodiments, the side wall 1316 may have a tubular shape and a first end coupled to peripheral portions of the bottom wall 1306. In other embodiments, the side wall 1316 may not be tubular in shape; instead, the base 1302 may have more than one adjoining side wall 1316. An end of the base 1302 opposite the bottom wall 1306 may be open. In some embodiments, the side wall 1316 may be coupled to the side wall 1354 of the cover 1304 to close the pressure indicator 1300.

In some embodiments, the pressure indicator 1300 may also include a pedestal 1308. The pedestal 1308 may be coupled to the bottom wall 1306 and extend parallel to the side wall 1316. In some embodiments, the pedestal 1308 may include multiple concentric annular walls, for example, an outer annular wall 1310, an intermediate annular wall 1312, and an interior annular wall 1314. The outer annular wall 1310, the intermediate annular wall 1312, and the interior annular wall 1314 may be separated by respective annuluses.

The interior annular wall 1314 may be disposed proximate to the opening 1305. In some embodiments, the interior annular wall 1314 may be coaxial with the opening 1305. In other embodiments, the interior annular wall 1314 may circumscribe the opening 1305. In some embodiments, the interior annular wall 1314 may have an inner diameter greater than a diameter of the opening 1305. In some embodiments, the interior annular wall 1314 may have a first end coupled to the bottom wall 1306 and a second end extending parallel to the side wall 1316.

The intermediate annular wall 1312 may be disposed proximate to the interior annular wall 1314. In some embodiments, the intermediate annular wall 1312 may be coaxial with the opening 1305. The intermediate annular wall 1312 may form a hollow cylinder having an inner diameter larger than an outer diameter of a hollow cylinder formed by the interior annular wall 1314 to form an annulus between the interior annular wall 1314 and the intermediate annular wall 1312. In some embodiments, the intermediate annular wall 1312 may be parallel to the side wall 1316 and may have a first end coupled to the bottom wall 1306. In some embodiments, the intermediate annular wall 1312 may be longer than the interior annular wall 1314.

The outer annular wall 1310 may be disposed proximate to the intermediate annular wall 1312. In some embodiments, the outer annular wall 1310 may be coaxial with the opening 1305. The outer annular wall 1310 may form a hollow cylinder having an inner diameter larger than an outer diameter of the hollow cylinder formed by the intermediate annular wall 1312 to form an annulus between the intermediate annular wall 1312 and the outer annular wall 1310. In some embodiments, the outer annular wall 1310 may be parallel to the side wall 1316 and have a first end coupled to the bottom wall 1306. In some embodiments, the outer annular wall 1310 may be longer than the interior annular wall 1314 and substantially equal to a length of the intermediate annular wall 1312.

In some embodiments, a spring 1318 may be disposed in the pressure indicator 1300. In some embodiments, the spring 1318 may have a first end positioned adjacent to the bottom wall 1306. In some embodiments, the first end of the spring 1318 may be proximate to the opening 1305. In some embodiments, the spring 1318 may be coaxial with the opening 1305 and disposed radially inward from the interior annular wall 1314. If the spring 1318 is in a relaxed position, the spring 1318 may have a length S between the first end and the second end of the spring 1318. In some embodiments, the spring 1318 may be longer than the interior annular wall 1314, the intermediate annular wall 1312, and the outer annular wall 1310.

In some embodiments, an actuator assembly 1320 be disposed on the pedestal 1308 opposite the bottom wall 1306. The actuator assembly 1320 may include a diaphragm 1321, a wall 1322, a side wall 1324, and an axle retainer 1326. In some embodiments, the diaphragm 1321 may be an annular body having peripheral portions coupled to the pedestal 1308. In some embodiments, the diaphragm 1321 may have an annular wall adapted to engage in an interference fit within the annulus between the outer annular wall 1310 and the intermediate annular wall 1312. In other embodiments, the diaphragm 1321 may be in contact with and supported by the intermediate annular wall 1312 and the outer annular wall 1310. In some embodiments, the diaphragm 1321 may be formed from a silicone material. In some embodiments, the diaphragm 1321 may have a hardness rating between about 100 Shore A and about 50 Shore A.

The side wall 1324 may be an annular wall. In some embodiments, the side wall 1324 may be disposed in an opening in the diaphragm 1321 formed by its annular shape. In some embodiments, the side wall 1324 may have an inner diameter greater than the outer diameter of the spring 1318 and an outer diameter less than the inner diameter of the interior annular wall 1314. In this manner, the side wall 1324 may circumscribe at least a portion of the spring 1318 and have at least a portion circumscribed by the interior annular wall 1314. In some embodiments, the side wall 1324 may have a first end proximate to the bottom wall 1306 and a second end opposite the first end.

The wall 1322 may be an annular member having an opening proximate to a center of the wall 1322. In some embodiments, the wall 1322 may have peripheral portions coupled to the second end of the side wall 1324. In some embodiments, the wall 1322 may be operatively coupled to the end of the spring 1318 that is opposite the bottom wall 1306. In some embodiments, the spring 1318 may support the wall 1322 above the bottom wall 1306.

The axle retainer 1326 may be a tubular body having a closed end and an open end opposite the closed end that is coupled to the wall 1322. In some embodiments, the axle retainer 1326 may be coupled to the wall 1322 proximate to the opening of the wall 1322. In some embodiments, the open end of the axle retainer 1326 may be coaxial with the opening in the wall 1322. In some embodiments, the axle retainer 1326 may be inserted into the spring 1318. In some embodiments, the axle retainer 1326 may include a ridge 1328 protruding from an interior surface of a side wall of the axle retainer 1326. In some embodiments, the ridge 1328 may extend parallel to the side wall 1316 from the wall 1322 to the closed end of the axle retainer 1326. In some embodiments, the ridge 1328 may have a spiral shape. In other embodiments, the ridge 1328 may have a helical shape.

The pressure indicator 1300 may also include a retainer 1330. The retainer 1330 may include an end wall 1332, a side wall 1334, an annular wall 1336, and a side wall 1338. The end wall 1332 may be a disc-shaped body having an opening proximate to a center of the disc-shaped body. The side wall 1334 may be an annular or tubular wall having a first end coupled to peripheral portions of the end wall 1332. The side wall 1334 may extend from the end wall 1332 toward the bottom wall 1306. The second end of the side wall 1334 may be coupled to interior portions of the annular wall 1336. The annular wall 1336 may have an inner diameter that is substantially equal to the outer diameter of the side wall 1334 and extend radially outward to form both upward and downward facing shoulders. The side wall 1338 may be coupled to peripheral portions of the annular wall 1336 and extend toward the bottom wall 1306. In some embodiments, the side wall 1338 may have an inner diameter greater than the diameter of the outer annular wall 1310 of the pedestal 1308. In some embodiments, the downward facing shoulder of the annular wall 1336 may rest on and be coupled to the diaphragm 1321 adjacent to the intermediate annular wall 1312, thereby securing the diaphragm 1321 to the pedestal 1308.

In some embodiments, a rotating indicator 1340 may be coupled to the retainer 1330. The rotating indicator 1340 may include a disc 1342, an axle 1344, and a bearing 1348 supporting the axle 1344 in the retainer 1330. The axle 1344 may be a cylindrical body having a first end disposed in the axle retainer 1326 and a second end proximate to the opening of the end wall 1332. In some embodiments, the axle 1344 includes a groove 1346. In some embodiments, the groove 1346 may extend a portion of a length of the axle 1344. In other embodiments, the groove 1346 may extend an entire length of the axle 1344. The groove 1346 may be sized to receive the ridge 1328. In some embodiments, the groove 1346 may be a spiral cut groove or helix. Generally, the groove 1346 may be sized and shaped to receive a mating size and shape of the ridge 1328.

In some embodiments, the bearing 1348 may be coupled to the second end of the axle 1344 proximate to the opening of the wall 1322. In some embodiments, the bearing 1348 may be a cylindrical body having an outer diameter that is larger than an outer diameter of the axle 1344. The bearing 1348 may have a groove 1341 formed in a side wall portion of the bearing 1348. The groove 1341 may be sized to receive a portion of the wall 1322 adjacent to the opening of the wall 1322. In some embodiments, the groove 1341 of the bearing 1348 may operate as a plain bearing. In other embodiments, the groove 1341 may be a roller bearing, or a fluid bearing, for example.

In some embodiments, the disc 1342 may be coupled to the bearing 1348 opposite the axle 1344. In some embodiments, the disc 1342 may be a disc-shaped body. In other embodiments, the disc 1342 may include a circular end wall, a tubular side wall coupled to peripheral portions of the end wall, and an annular wall coupled to the tubular side wall and extending radially outward. For example, the disc 1342 may be adapted to receive the radial limiter 1360 proximate to a center of the disc 1342. In other embodiments, the radial limiter 1360 may not be included. In some embodiments, the disc 1342 may have a surface proximate to the end wall 1358 of the cover 1304. In some embodiments, the disc 1342 may have one or more indicators 1352 coupled to the surface of the disc proximate to the end wall 1358. The indicators 1352 may be spaced circumferentially around the disc 1342 proximate to a circumferential edge of the disc 1342. In some embodiments, the indicators 1352 may be equidistantly spaced around the circumference of the disc 1342. In some embodiments, the indicators 1352 may be aligned with the windows 1356 so that if an indicator 1352 is aligned with a window 1356, each of the indicators 1352 may be aligned with a respective window 1356.

Figure 19:
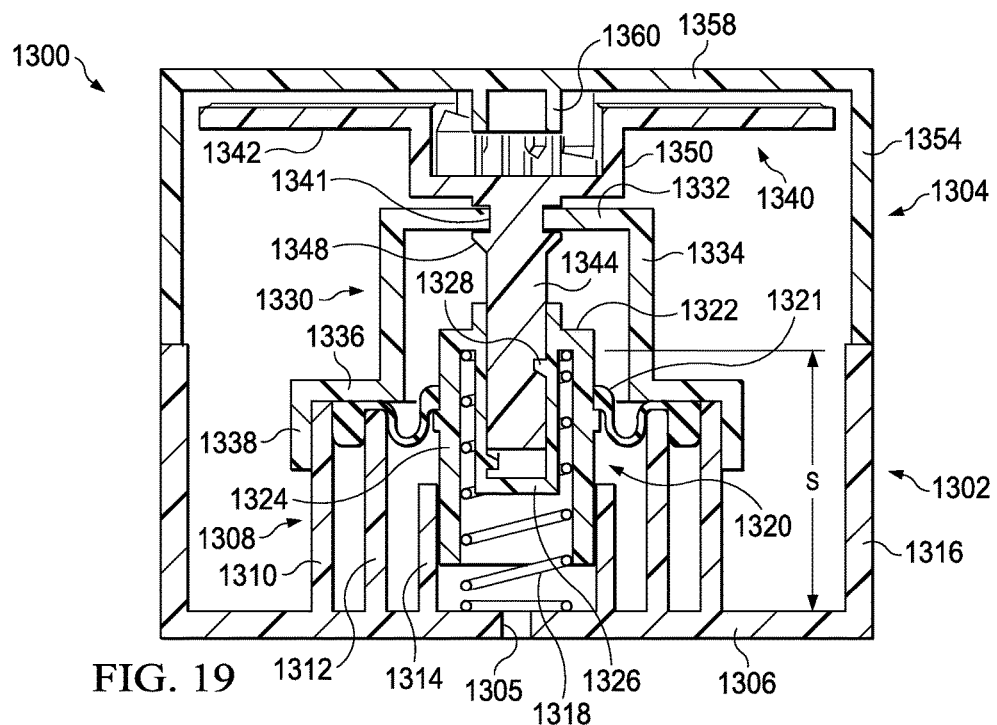
FIG. 19 is a schematic sectional view illustrating additional details that may be associated with an example state of the feedback interface of FIG. 18.

FIG. 19 is a schematic perspective view, illustrating additional details of a pressure indicator 1300 that may be used with some embodiments of the reduced-pressure system 400 or the reduced-pressure system 1100. In some embodiments, a reduced pressure may be coupled to the pressure indicator 1300 through the opening 1305 in the bottom wall 1306. Reduced pressure supplied to the pressure indicator 1300 through the opening 1305 may exert a force on the diaphragm 1321 urging the diaphragm 1321 toward the bottom wall 1306. Similarly, ambient pressure supplied through the windows 1356 may exert a force on the diaphragm 1321. The combined forces may be considered a differential force acting on the diaphragm 1321. The differential force may urge the diaphragm 1321 toward the bottom wall 1306 if the pressure supplied through the opening 1305 is less than the ambient pressure. As shown in FIG. 19, the differential force is less than the force of the spring 1318, and the diaphragm 1321 may not move in response.

Figure 20:
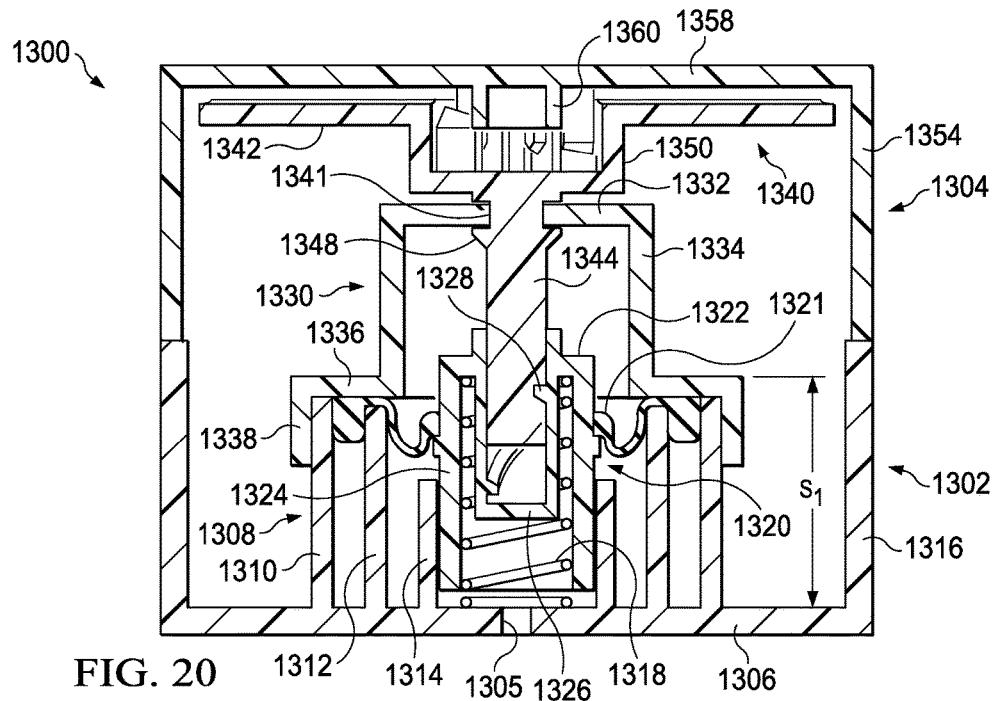
FIG. 20 is a schematic sectional view illustrating additional details that may be associated with an example state of the feedback interface of FIG. 18.

FIG. 20 is a schematic perspective view, illustrating additional details of a pressure indicator 1300 that may be used with some embodiments of the reduced-pressure system 400 or the reduced-pressure system 1100. If the reduced pressure supplied through the opening 1305 is about the therapy pressure, the differential force may overcome the force of the spring 1318, urging the diaphragm 1321 toward the bottom wall 1306. In response, the remainder of the actuator assembly 1320 coupled to the diaphragm 1321 may also be urged toward the bottom wall 1306 so that the axle retainer 1326 and the wall 1322 move toward the bottom wall 1306, compressing the spring 1318 from the relaxed position. The retainer 1330 may prevent the rotating indicator 1340 from moving toward the bottom wall 1306 through the bearing 1348 and the end wall 1332. As the axle retainer 1326 moves toward the bottom wall 1306 and the axle 1344 does not, the ridge 1328 may be moved through the groove 1346, causing the axle 1344 to rotate. In response, the disc 1342 may rotate and align the indicators 1352 with the windows 1356, providing an indication that the supplied pressure is about the therapy pressure. If the supply of reduced pressure through the opening 1305 is removed, the differential force may move toward zero, and the spring 1318 may exert a force proportional to the distance the spring 1318 is compressed from the relaxed position S to a compressed position $S_1$, that causes the axle 1344 to rotate back to the position illustrated in FIG. 19.

Feedback interfaces in the reduced-pressure system 400 or the reduced-pressure system 1100 may be configured to address particular concerns. For example, if an operator is concerned about overpressure condition operating states, the operator may use the pressure indicator 600, the pressure indicator 700, or the pressure indicator 900 at location 416, location 420, location 424, and location 428. If an operator is concerned about leak condition operating states, the operator may use the pressure indicator 600, the pressure indicator 700, or the pressure indicator 900 at location 416, location 420, location 424, and location 428. If an operator is concerned about blockage condition or canister full condition operating states, the operator may use the pressure indicator 800 at location 426. If an operator is concerned about an application of therapy pressure operating state, the operator may use the pressure indicator 500 at location 416, location 418, location 420, location 424, location 426, location 428, or location 430. Each feedback interface may operate independently of the others and may be selected by an operator based at least in part on a cost, a desired feedback, and a region of operation.

In some embodiments, the regulator 200 may include monitor ports similar to the monitor port 319 and the monitor port 323 of the regulator 300. Similarly, the regulator 300 may include tee-fittings similar to the tee-fitting 215 and the tee-fitting 217 of the regulator 200. The monitor ports and the tee-fittings may be similarly coupled to the respective regulators and operate in a similar way.

In some embodiments, a secondary regulator may be positioned in-line between a reduced-pressure source and the regulator 300 to purge blockages. A secondary regulator may include a release mechanism allowing the secondary regulator to flood the charging chamber 308 with a higher pressure in an attempt to eliminate blockages. Feedback can be provided to an operator that a blockage is cleared as described above. Additionally, the system may have a relief valve to ensure that once a blockage is cleared pressure at a tissue site may not rise above a predetermined safe limit.

The devices and systems described herein may provide variable negative pressure settings to an operator, feedback to an operator on leak conditions, feedback to an operator on blockage conditions, feedback to an operator on canister full conditions, may be low cost, may be disposable, may be for single patient use or reusable, and may be highly configurable.

It should be apparent from the foregoing that systems, methods, and apparatuses having significant advantages has been described. For example, a variety of feedback interfaces and methods have been described to provide feedback on the status of a reduced-pressure system, as well as actions that may be needed to continue therapy without significant interruption. Some example embodiments may provide feedback that reduced-pressure is being applied to a tissue site, and some example embodiments may also integrate an over-pressure valve with a pressure indicator. Additionally or alternatively, some embodiments may provide feedback for leak conditions, blockage conditions, and canister full conditions. The illustrative embodiments described herein also exemplify how such feedback may be implemented in a low-cost system powered by wall-suction with not need for an internal or external power supply.

while shown in only a few forms, the systems, methods, and apparatuses illustrated are susceptible to various changes, modifications, and uses encompassed within the claims that follow.

We claim:
1. A reduced-pressure system comprising:
a dressing;
a regulator comprising:
  a supply chamber adapted to be fluidly coupled to the dressing,
  a control chamber adapted to be fluidly coupled to the dressing,
  a charging chamber fluidly coupled to the supply chamber through a port, and
  a regulator valve coupled to the control chamber and operable to reciprocate at least partially within the control chamber to control fluid communication through the port based on a differential between a control pressure in the control chamber and a therapy pressure; and
a feedback interface fluidly coupled to the regulator and adapted to signal an operating state of the reduced-pressure therapy system in response to a pressure received through the fluid coupling.

2. The reduced-pressure system of claim 1, wherein the feedback interface is fluidly coupled between a container and the regulator.

3. The reduced-pressure system of claim 1, wherein the feedback interface is fluidly coupled between a container and the dressing.

4. The reduced-pressure system of claim 1, wherein the feedback interface is fluidly coupled between the control chamber and the dressing.

5. The reduced-pressure system of claim 1, wherein the feedback interface is fluidly coupled between the supply chamber and the dressing.

6. The reduced-pressure system of claim 1, wherein the feedback interface is fluidly coupled between the regulator and the dressing.

7. The reduced-pressure system of claim 1, wherein the feedback interface is fluidly coupled between the control chamber and the supply chamber.

8. The reduced-pressure system of claim 1, wherein the feedback interface is fluidly coupled between a reduced-pressure source and the regulator.

9. The reduced-pressure system of claim 1, wherein the feedback interface is fluidly coupled between a reduced-pressure source and the charging chamber.

10. The reduced-pressure system of claim 1, wherein the feedback interface comprises a side wall configured to collapse if reduced pressure exceeds the therapy pressure.

11. The reduced-pressure system of claim 1, wherein the feedback interface comprises a whistle.

12. The reduced-pressure system of claim 1, wherein the feedback interface comprises a mechanical pressure gauge.

13. The reduced-pressure system of claim 1, wherein the feedback interface comprises a visual feedback interface.

14. The reduced-pressure system of claim 1, wherein the feedback interface comprises a visual feedback interface and an overpressure valve.

15. The reduced-pressure system of claim 7, wherein:
the feedback interface comprises a window, a first indicator ring, and a second indicator ring;
the first indicator ring is configured to be visible through the window at a first pressure; and
the second indicator ring is configured to be visible through the window at a second pressure.

16. The reduced-pressure system of claim 1, wherein the feedback interface comprises an overpressure valve having a whistle.

17. The reduced-pressure system of claim 1, wherein the feedback interface comprises a plurality of feedback interfaces selected from a group consisting of a visual feedback interface, an audible feedback interface, and a tactile feedback interface.

18. The reduced-pressure system of claim 1, wherein the feedback interface comprises:
a housing comprising a chamber disposed between an end wall and an open end, and a window proximate to the open end;
a diaphragm disposed in the chamber, the diaphragm having a peripheral portion coupled to the housing;
a stem coupled to the diaphragm and having a portion passing through the diaphragm;
a cap coupled to an end of the stem proximate to the open end of the housing, the cap having a plurality of indicator rings; and a biasing member coupled between the diaphragm and the end wall, wherein the biasing member is adapted to exert a force urging the diaphragm toward the open end.

19. The reduced-pressure system of claim 18, wherein the stem has a cavity and the feedback interface further comprises:
a valve member disposed in the cavity;
a spring disposed in the cavity between the valve member and an end of the spring; and
a whistle coupled to the cap.

20. The reduced-pressure system of claim 1, comprising at least two feedback interfaces, wherein a first feedback interface is fluidly coupled between the supply chamber and the control chamber and a second feedback interface is fluidly coupled between the first feedback interface and the supply chamber.

21. The reduced-pressure system of claim 1, comprising at least two feedback interfaces, wherein a first feedback interface is fluidly coupled between the supply chamber and the control chamber and a second feedback interface is fluidly coupled between the first feedback interface and the control chamber.

22. The reduced-pressure system of claim 1, wherein the feedback interface comprises:
a housing having an end wall and an open end opposite the end wall;
a diaphragm disposed within the housing and forming a first chamber and a second chamber, the first chamber adapted to be fluidly coupled to the control chamber and the second chamber adapted to be fluidly coupled to the supply chamber;
a partition disposed in the housing between the diaphragm and the open end, the partition having an opening;
a stem extending through the opening of the partition, the stem having a first end coupled to the diaphragm;
a spring coupled between the diaphragm and the partition, the spring circumscribing the stem and adapted to urge the diaphragm toward the end wall;
a cap coupled to the stem opposite the diaphragm, the cap having a first portion with a first color and a second portion with a second color; and
a whistle coupled to the open end of the housing and adapted to emit an audible tone;
wherein an increase in reduced pressure in the second chamber relative to the first chamber urges the diaphragm toward the partition, exposing the second color through the window and permitting fluid communication through the whistle into the second chamber.

23. The reduced-pressure system of claim 1, wherein the feedback interface comprises:
a housing having a chamber disposed between an end wall and an open end;
a valve positioned within the chamber and adapted to open in response to a differential pressure across the valve; and
a whistle positioned adjacent to the valve and adapted to emit an audible tone in response to opening of the valve.

24. The reduced-pressure system of claim 23, wherein the valve is a duck-bill valve.

25. The reduced-pressure system of claim 1, wherein the feedback interface comprises:
a housing having a window on a first end;
a diaphragm disposed in the housing to form a pressure chamber on a second end of the housing;

a lever having a fixed end coupled to the housing and a free end proximate to the window;
an arm having a first end coupled to the lever and a second end coupled to the diaphragm, wherein the arm is configured to rotate the lever in response to movement of the diaphragm;
an indicator coupled to the free end of the lever; and
a biasing member coupled between the diaphragm and a second end of the housing, wherein the biasing member is adapted to exert a force urging the diaphragm toward the first end.

26. The reduced-pressure system of claim 1, wherein the feedback interface comprises:
a housing having at least one window on a first end;
a diaphragm disposed in the housing to form a pressure chamber on a second end of the housing;
a disc having at least one indicator, the disc operatively coupled to the diaphragm and configured to rotate in response to movement of the diaphragm; and
a biasing member coupled between the diaphragm and a second end of the housing, wherein the biasing member is adapted to exert a force urging the diaphragm toward the first end.

27. The reduced-pressure system of claim 1, further comprising a wall-suction source fluidly coupled to the charging chamber.

28. The reduced-pressure therapy system of claim 1, wherein the operating state comprises at least one of an application of a reduced pressure, a leak condition, a blockage condition, a canister full condition, and an overpressure condition.

29. A method for regulating pressure in a reduced-pressure therapy system, the method comprising:
reducing a charging pressure in a charging chamber below a therapy pressure;
regulating fluid communication between a supply chamber and the charging chamber based on a differential between a control pressure in a control chamber and the therapy pressure;
fluidly coupling a feedback interface between at least two of the control chamber, the charging chamber, a dressing, and a reduced-pressure source; and
signaling an operating state of the reduced-pressure therapy system with the feedback interface in response to a pressure received through the fluid coupling.

30. The method of claim 29, wherein fluidly coupling the feedback interface comprises fluidly coupling the feedback interface between a container and the supply chamber.

31. The method of claim 29, wherein fluidly coupling the feedback interface comprises fluidly coupling the feedback interface between a container and the dressing.

32. The method of claim 29, wherein fluidly coupling the feedback interface comprises fluidly coupling the feedback interface between the control chamber and the dressing.

33. The method of claim 29, wherein fluidly coupling the feedback interface comprises fluidly coupling the feedback interface between the supply chamber and the dressing.

34. The method of claim 29, wherein fluidly coupling the feedback interface comprises fluidly coupling the feedback interface between the control chamber and the supply chamber.

35. The method of claim 29, wherein fluidly coupling the feedback interface comprises fluidly coupling the feedback interface between a reduced-pressure source and the charging chamber.

36. The method of claim 29, wherein fluidly coupling the feedback interface comprises fluidly coupling at least one of a visual feedback interface, an audible feedback interface, and a tactile feedback interface.

37. The method of claim 29, wherein the operating state is at least one of an application of reduced pressure, a leak condition, a blockage condition, a canister full condition, and an overpressure condition.

38. The method of claim 29, wherein signaling an operating state of the reduced-pressure therapy system comprises collapsing a side wall of the feedback interface if reduced pressure exceeds the therapy pressure.

39. The method of claim 29, wherein the feedback interface comprises a whistle and signaling an operating state of the reduced-pressure therapy system comprises operating the whistle.

40. The method of claim 29, wherein the feedback interface comprises a mechanical pressure gauge and signaling an operating state of the reduced-pressure therapy system comprises measuring and indicating a pressure with the mechanical pressure gauge.

41. The method of claim 29, wherein the feedback interface comprises a visual feedback interface and signaling an operating state of the reduced-pres sure therapy system comprises visually representing the operating state.

42. The method of claim 29, wherein the feedback interface comprises a visual feedback interface and an overpressure valve and signaling an operating state of the reduced-pressure therapy system comprises visually representing the operating state.

43. The method of claim 34, wherein the feedback interface comprises a window, a first indicator ring, and a second indicator ring, and signaling an operating state of the reduced-pressure therapy system comprises:
    displaying the first indicator ring through the window at a first pressure; and
    displaying the second indicator ring through the window at a second pressure.

44. The method of claim 29, wherein the feedback interface comprises an overpressure valve having a whistle and signaling an operating state of the reduced-pressure therapy system comprises operating the whistle if the pressure received through the fluid coupling exceeds the cracking pressure of the overpressure valve.

45. The method of claim 29, wherein the feedback interface comprises a plurality of feedback interfaces selected from a group consisting of a visual feedback interface, an audible feedback interface, and a tactile feedback interface.

46. The method of claim 29, wherein:
    the feedback interface comprises:
        a housing comprising a chamber disposed between an end wall and an open end, and a window proximate to the open end;
        a diaphragm disposed in the chamber, the diaphragm having a peripheral portion coupled to the housing;
        a stem coupled to the diaphragm and having a portion passing through the diaphragm;
        a cap coupled to an end of the stem proximate to the open end of the housing, the cap having a plurality of indicator rings; and
        a biasing member coupled between the diaphragm and the end wall, wherein the biasing member is adapted to exert a force urging the diaphragm toward the open end; and
    signaling an operating state of the reduced-pressure therapy system comprises.

47. The method of claim 46, wherein the stem has a cavity and the feedback interface further comprises:
    a valve member disposed in the cavity;
    a spring disposed in the cavity between the valve member and an end of the spring; and
    a whistle coupled to the cap.

48. The method of claim 29, comprising at least two feedback interfaces, wherein a first feedback interface is fluidly coupled between the supply chamber and the control chamber and a second feedback interface is fluidly coupled between the first feedback interface and the supply chamber.

49. The method of claim 29, comprising at least two feedback interfaces, wherein a first feedback interface is fluidly coupled between the supply chamber and the control chamber and a second feedback interface is fluidly coupled between the first feedback interface and the control chamber.

50. The method of claim 29, wherein the feedback interface comprises:
    a housing having an end wall and an open end opposite the end wall;
    a diaphragm disposed within the housing and forming a first chamber and a second chamber, the first chamber adapted to be fluidly coupled to the control chamber and the second chamber adapted to be fluidly coupled to the supply chamber;
    a partition disposed in the housing between the diaphragm and the open end, the partition having an opening;
    a stem extending through the opening of the partition, the stem having a first end coupled to the diaphragm;
    a spring coupled between the diaphragm and the partition, the spring circumscribing the stem and adapted to urge the diaphragm toward the end wall;
    a cap coupled to the stem opposite the diaphragm, the cap having a first portion with a first color and a second portion with a second color; and
    a whistle coupled to the open end of the housing and adapted to emit an audible tone;
    wherein an increase in reduced pressure in the second chamber relative to the first chamber urges the diaphragm toward the partition, exposing the second color through the window and permitting fluid communication through the whistle into the second chamber.

51. The method of claim 29, wherein the feedback interface comprises:
    a housing having a chamber disposed between an end wall and an open end;
    a valve positioned within the chamber and adapted to open in response to a differential pressure across the valve; and
    a whistle positioned adjacent to the valve and adapted to emit an audible tone in response to opening of the valve.

52. The method of claim 51, wherein the valve is a duck-bill valve.

53. The method of claim 29, wherein the feedback interface comprises:
    a housing having a window on a first end;
    a diaphragm disposed in the housing to form a pressure chamber on a second end of the housing;
    a lever having a fixed end coupled to the housing and a free end proximate to the window;
    an arm having a first end coupled to the lever and a second end coupled to the diaphragm, wherein the arm is configured to rotate the lever in response to movement of the diaphragm;

an indicator coupled to the free end of the lever; and
a biasing member coupled between the diaphragm and a second end of the housing, wherein the biasing member is adapted to exert a force urging the diaphragm toward the first end.

54. The method of claim 29, wherein the feedback interface comprises:
a housing having at least one window on a first end;
a diaphragm disposed in the housing to form a pressure chamber on a second end of the housing;
a disc having at least one indicator, the disc operatively coupled to the diaphragm and configured to rotate in response to movement of the diaphragm; and
a biasing member coupled between the diaphragm and a second end of the housing, wherein the biasing member is adapted to exert a force urging the diaphragm toward the first end.

55. The method of claim 29, further comprising a wall-suction source fluidly coupled to the charging chamber.

56. A reduced-pressure system comprising:
a dressing;
a regulator comprising:
a supply chamber adapted to be fluidly coupled to the dressing,
a charging chamber fluidly coupled to the supply chamber through a port, and
a regulator valve coupled to the charging chamber and operable to reciprocate to control fluid communication through the port based on a differential between an ambient pressure and a therapy pressure; and
a feedback interface fluidly coupled to the regulator and adapted to signal an operating state of the reduced-pressure therapy system in response to a pressure received through the fluid coupling.

57. The reduced-pressure system of claim 56, wherein the feedback interface is fluidly coupled between a container and the regulator.

58. The reduced-pressure system of claim 56, wherein the feedback interface is fluidly coupled between a container and the dressing.

59. The reduced-pressure system of claim 56, wherein the feedback interface is fluidly coupled to the dressing.

60. The reduced-pressure system of claim 56, wherein the feedback interface is fluidly coupled between the supply chamber and the dressing.

61. The reduced-pressure system of claim 56, wherein the feedback interface is fluidly coupled between a reduced-pressure source and the regulator.

62. The reduced-pressure system of claim 56, wherein the feedback interface is fluidly coupled between a reduced-pressure source and the charging chamber.

63. The reduced-pressure system of claim 56, wherein the feedback interface comprises a side wall configured to collapse if reduced pressure exceeds the therapy pressure.

64. The reduced-pressure system of claim 56, wherein the feedback interface comprises a whistle.

65. The reduced-pressure system of claim 56, wherein the feedback interface comprises a mechanical pressure gauge.

66. The reduced-pressure system of claim 56, wherein the feedback interface comprises a visual feedback interface.

67. The reduced-pressure system of claim 56, wherein the feedback interface comprises a visual feedback interface and an overpressure valve.

68. The reduced-pressure system of claim 66, wherein:
the feedback interface comprises a window, a first indicator ring, and a second indicator ring;
the first indicator ring is configured to be visible through the window at a first pressure; and
the second indicator ring is configured to be visible through the window at a second pressure.

69. The reduced-pressure system of claim 56, wherein the feedback interface comprises an overpressure valve having a whistle.

70. The reduced-pressure system of claim 56, wherein the feedback interface comprises a plurality of feedback interfaces selected from a group consisting of a visual feedback interface, an audible feedback interface, and a tactile feedback interface.

71. The reduced-pressure system of claim 56, wherein the feedback interface comprises:
a housing comprising a chamber disposed between an end wall and an open end, and a window proximate to the open end;
a diaphragm disposed in the chamber, the diaphragm having a peripheral portion coupled to the housing;
a stem coupled to the diaphragm and having a portion passing through the diaphragm;
a cap coupled to an end of the stem proximate to the open end of the housing, the cap having a plurality of indicator rings; and
a biasing member coupled between the diaphragm and the end wall, wherein the biasing member is adapted to exert a force urging the diaphragm toward the open end.

72. The reduced-pressure system of claim 71, wherein the stem has a cavity and the feedback interface further comprises:
a valve member disposed in the cavity;
a spring disposed in the cavity between the valve member and an end of the spring; and
a whistle coupled to the cap.

73. The reduced-pressure system of claim 56, wherein the feedback interface comprises:
a housing having a chamber disposed between an end wall and an open end;
a valve positioned within the chamber and adapted to open in response to a differential pressure across the valve; and
a whistle positioned adjacent to the valve and adapted to emit an audible tone in response to opening of the valve.

74. The reduced-pressure system of claim 73, wherein the valve is a duck-bill valve.

75. The reduced-pressure system of claim 56, wherein the feedback interface comprises:
a housing having a window on a first end;
a diaphragm disposed in the housing to form a pressure chamber on a second end of the housing;
a lever having a fixed end coupled to the housing and a free end proximate to the window;
an arm having a first end coupled to the lever and a second end coupled to the diaphragm, wherein the arm is configured to rotate the lever in response to movement of the diaphragm;
an indicator coupled to the free end of the lever; and
a biasing member coupled between the diaphragm and a second end of the housing, wherein the biasing member is adapted to exert a force urging the diaphragm toward the first end.

76. The reduced-pressure system of claim 56, wherein the feedback interface comprises:
- a housing having at least one window on a first end;
- a diaphragm disposed in the housing to form a pressure chamber on a second end of the housing;
- a disc having at least one indicator, the disc operatively coupled to the diaphragm and configured to rotate in response to movement of the diaphragm; and
- a biasing member coupled between the diaphragm and a second end of the housing, wherein the biasing member is adapted to exert a force urging the diaphragm toward the first end.

77. The reduced-pressure system of claim 56, further comprising a wall-suction source fluidly coupled to the charging chamber.

78. The reduced-pressure system of claim 56, wherein the operating state comprises at least one of an application of a reduced pressure, a leak condition, a blockage condition, a canister full condition, and an overpressure condition.

\* \* \* \* \*